(12) United States Patent  
Gupta et al.

(10) Patent No.: US 9,316,631 B1  
(45) Date of Patent: Apr. 19, 2016

(54) ER-STRESS INDUCING COMPOUNDS AND METHODS OF USE THEREOF

(71) Applicant: Whitehead Institute for Biomedical Research, Cambridge, MA (US)

(72) Inventors: Piyush Gupta, Boston, MA (US); Yuxiong Feng, Brookline, MA (US)

(*) Notice: Subject to any disclaimer, the term of this patent is extended or adjusted under 35 U.S.C. 154(b) by 0 days.

(21) Appl. No.: 14/057,473

(22) Filed: Oct. 18, 2013

Related U.S. Application Data

(60) Provisional application No. 61/716,112, filed on Oct. 19, 2012.

(51) Int. Cl.
| | | |
|---|---|---|
| *A61K 31/415* | (2006.01) | |
| *A61K 31/35* | (2006.01) | |
| *A61K 31/41* | (2006.01) | |
| *G01N 33/50* | (2006.01) | |
| *G01N 33/574* | (2006.01) | |
| *A61K 31/4025* | (2006.01) | |
| *A61K 31/40* | (2006.01) | |

(52) U.S. Cl.
CPC ............ *G01N 33/5011* (2013.01); *A61K 31/40* (2013.01); *A61K 31/4025* (2013.01); *G01N 33/57496* (2013.01)

(58) Field of Classification Search
CPC .. G01N 33/68; G01N 33/5011; A61K 31/357
USPC .......................................... 514/359, 389, 457
See application file for complete search history.

(56) References Cited

PUBLICATIONS

Kitamura et al., "Real-Time Monitoring of ER Stress in Living Cells and Animals Using ESTRAP Assay", Methods in Enzymology, vol. 490, pp. 93-106 (2011).*
Abrams et al., CrebA regulates secretory activity in the *Drosophila* salivary gland and epidermis. Development. Jun. 2005;132(12):2743-58. Epub May 18, 2005.
Aridor et al., Cargo selection by the COPII budding machinery during export from the ER. J Cell Biol. Apr. 6, 1998;141(1):61-70.
Bao et al., Glioma stem cells promote radioresistance by preferential activation of the DNA damage response. Nature. Dec. 7, 2006;444(7120):756-60. Epub Oct. 18, 2006.
Bartkowiak et al., Discovery of a novel unfolded protein response phenotype of cancer stem/progenitor cells from the bone marrow of breast cancer patients. J Proteome Res. Jun. 4, 2010;9(6):3158-68. doi: 10.1021/pr100039d.
Bergmeier et al., Extracellular matrix proteins in hemostasis and thrombosis. Cold Spring Harb Perspect Biol. Feb. 1, 2012;4(2). pii: a005132. doi: 10.1101/cshperspect.a005132.

(Continued)

*Primary Examiner* — Kevin E Weddington
(74) *Attorney, Agent, or Firm* — Wolf, Greenfield & Sacks, P.C.

(57) ABSTRACT

The invention relates to methods for identifying ER-stress inducing compounds that target cancer stem cells. In some aspects, the invention relates to treatment methods that use ER-stress inducing compounds that specifically target cancer stem cells for inhibiting the growth and/or survival of cancer stem cells in a subject in need thereof. Other aspects of the invention relate to the use of cancer stem cell biomarkers in the selection of a treatment for inhibiting the growth and/or survival of cancer stem cells in a subject in need thereof.

16 Claims, 42 Drawing Sheets

CMP302

CMP308

DEV4

(56) References Cited

PUBLICATIONS

Bhattacharyya et al., Two mammalian Sec16 homologues have nonredundant functions in endoplasmic reticulum (ER) export and transitional ER organization. Mol Biol Cell. Mar. 2007;18(3):839-49. Epub Dec. 27, 2006.

Bi et al., ER stress-regulated translation increases tolerance to extreme hypoxia and promotes tumor growth. EMBO J. Oct. 5, 2005;24(19):3470-81. Epub Sep. 8, 2005.

Chen, Regulation of protein synthesis by the heme-regulated eIF2alpha kinase: relevance to anemias. Blood. Apr. 1, 2007;109(7):2693-9.

Clemens et al., The double-stranded RNA-dependent protein kinase PKR: structure and function. J Interferon Cytokine Res. Sep. 1997;17(9):503-24.

Del Castillo et al., Autocrine production of TGF-beta confers resistance to apoptosis after an epithelial-mesenchymal transition process in hepatocytes: Role of EGF receptor ligands. Exp Cell Res. Sep. 10, 2006;312(15):2860-71. Epub Jun. 7, 2006.

Diehn et al., Cancer stem cells and radiotherapy: new insights into tumor radioresistance. J Natl Cancer Inst. Dec. 20, 2006;98(24):1755-7.

Dontu et al., In vitro propagation and transcriptional profiling of human mammary stem/progenitor cells. Genes Dev. May 15, 2003;17(10):1253-70.

Fox et al., The CrebA/Creb3-like transcription factors are major and direct regulators of secretory capacity. J Cell Biol. Nov. 1, 2010;191(3):479-92. doi: 10.1083/jcb.201004062.

Franco et al., Snail1 suppresses TGF-beta-induced apoptosis and is sufficient to trigger EMT in hepatocytes. J Cell Sci. Oct. 15, 2010;123(Pt 20):3467-77. doi: 10.1242/jcs.068692.

Germain et al., Identification of a selective small molecule inhibitor of breast cancer stem cells. Bioorg Med Chem Lett. May 15, 2012;22(10):3571-4. doi: 10.1016/j.bmcl.2012.01.035. Epub Jan, 25, 2012.

Gimeno et al., COPII coat subunit interactions: Sec24p and Sec23p bind to adjacent regions of Sec16p. Mol Biol Cell. Nov. 1996;7(11):1815-23.

Gomez et al., Human X-box binding protein-1 confers both estrogen independence and antiestrogen resistance in breast cancer cell lines. FASEB J. Dec. 2007;21(14):4013-27. Epub Jul. 27, 2007.

Guo et al., Slug and Sox9 cooperatively determine the mammary stem cell state. Cell. Mar. 2, 2012;148(5):1015-28. doi: 10.1016/j.cell.2012.02.008.

Gupta et al., Identification of selective inhibitors of cancer stem cells by high-throughput screening. Cell. Aug. 21, 2009;138(4):645-59. doi: 10.1016/j.cell.2009.06.034. Epub Aug. 13, 2009.

Gupta et al., The melanocyte differentiation program predisposes to metastasis after neoplastic transformation. Nat Genet. Oct. 2005;37(10):1047-54. Epub Sep. 4, 2005.

Györffy et al., An online survival analysis tool to rapidly assess the effect of 22,277 genes on breast cancer prognosis using microarray data of 1,809 patients. Breast Cancer Res Treat. Oct. 2010;123(3):725-31. doi: 10.1007/s10549-009-0674-9. Epub Dec. 18, 2009.

Harding et al., An integrated stress response regulates amino acid metabolism and resistance to oxidative stress. Mol Cell. Mar. 2003;11(3):619-33.

Harding et al., Protein translation and folding are coupled by an endoplasmic-reticulum-resident kinase. Nature. Jan. 21, 1999;397(6716):271-4. Erratum in: Nature Mar. 4, 1999;398(6722):90.

Hetz, The unfolded protein response: controlling cell fate decisions under ER stress and beyond. Nat Rev Mol Cell Biol. Jan. 18, 2012;13(2):89-102. doi: 10.1038/nrm3270.

Hollestelle et al., Distinct gene mutation profiles among luminal-type and basal-type breast cancer cell lines. Breast Cancer Res Treat. May 2010;121(1):53-64. doi: 10.1007/s10549-009-04608. Epub Jul. 11, 2009.

Ince et al., Transformation of different human breast epithelial cell types leads to distinct tumor phenotypes. Cancer Cell. Aug. 2007;12(2):160-70.

Iwakoshi et al., Plasma cell differentiation and the unfolded protein response intersect at the transcription factor XBP-1. Nat Immunol. Apr. 2003;4(4):321-9. Epub Mar. 3, 2003.

Kaufman, Orchestrating the unfolded protein response in health and disease. J Clin Invest. Nov. 2002;110(10):1389-98.

Keller et al., Defining the cellular precursors to human breast cancer. Proc Natl Acad Sci U S A. Feb. 21, 2012;109(8):2772-7. doi: 10.1073/pnas.1017626108. Epub Sep. 21, 2011.

Keller et al., Mapping the cellular and molecular heterogeneity of normal and malignant breast tissues and cultured cell lines. Breast Cancer Res. 2010;12(5):R87. doi: 10.1186/bcr2755. Epub Oct 21, 2010.

Korpal et al., Direct targeting of Sec23a by miR-200s influences cancer cell secretome and promotes metastatic colonization. Nat Med. Aug. 7, 2011;17(9):1101-8. doi: 10.1038/nm.2401.

Lee et al., GRP78 as potential predictor for breast cancer response to adjuvant taxane therapy. Int J Cancer. Feb. 1, 2011;128(3):726-31. doi: 10.1002/ijc.25370.

Liu et al., Hypoxic reactive oxygen species regulate the integrated stress response and cell survival. J Biol Chem. 2008 Nov. 7, 2008;283(45):31153-62. doi: 10.1074/jbc.M805056200. Epub Sep. 3, 2008.

Luo et al., Highly parallel identification of essential genes in cancer cells. Proc Natl Acad Sci U S A. Dec. 23, 2008;105(51):20380-5. doi: 10.1073/pnas.0810485105. Epub Dec. 17, 2008.

Mani et al., The epithelial-mesenchymal transition generates cells with properties of stem cells. Cell. May 16, 2008;133(4):704-15. doi: 10.1016/j.cell.2008.03.027.

McMillan et al., The cellular response to unfolded proteins: intercompartmental signaling. Curr Opin Biotechnol. Oct. 1994;5(5):540-5.

Mozos et al., The expression of the endoplasmic reticulum stress sensor BiP/GRP78 predicts response to chemotherapy and determines the efficacy of proteasome inhibitors in diffuse large b-cell lymphoma. Am J Pathol. Nov. 2011;179(5):2601-10. doi: 10.1016/j.ajpath.2011.07.031. Epub Sep. 9, 2011.

Mulvey et al., Resistance of mRNA translation to acute endoplasmic reticulum stress-inducing agents in herpes simplex virus type 1-infected cells requires multiple virus-encoded functions. J Virol. Aug. 2006;80(15):7354-63.

Neven et al.,. A gene signature of loss of oestrogen receptor (ER) function and oxidative stress links ER-positive breast tumours with an absent progesterone receptor and a poor prognosis. Breast Cancer Res. 2008;10(5):109. doi: 10.1186/bcr2135. Epub Sep. 4, 2008.

Pagliarini et al., A genetic screen in *Drosophila* for metastatic behavior. Science. Nov. 14, 2003;302(5648):1227-31. Epub Oct. 9, 2003.

Prat et al., Phenotypic and molecular characterization of the claudin-low intrinsic subtype of breast cancer. Breast Cancer Res. 2010;12(5):R68. doi: 10.1186/bcr2635. Epub Sep. 2, 2010.

Qin et al., The mammalian Scribble polarity protein regulates epithelial cell adhesion and migration through E-cadherin. J Cell Biol. Dec. 19, 2005;171(6):1061-71. Epub Dec. 12, 2005.

Ranganathan et al., Functional coupling of p38-induced up-regulation of BiP and activation of RNA-dependent protein kinase-like endoplasmic reticulum kinase to drug resistance of dormant carcinoma cells. Cancer Res. Feb. 1, 2006;66(3):1702-11. Erratum in: Cancer Res. Mar. 15, 2006;66(6):3345.

Reimold et al., Plasma cell differentiation requires the transcription factor XBP-1. Nature. Jul. 19, 2001;412(6844):300-7.

Ron et al., Signal integration in the endoplasmic reticulum unfolded protein response. Nat Rev Mol Cell Biol. Jul. 2007;8(7):519-29.

Ron, Translational control in the endoplasmic reticulum stress response. J Clin Invest. Nov. 2002;110(10):1383-8.

Rzymski et al., Role of ATF4 in regulation of autophagy and resistance to drugs and hypoxia. Cell Cycle. Dec. 2009;8(23):3838-47. Epub Dec. 15, 2009.

Sanai et al., Neural stem cells and the origin of gliomas. N Engl J Med. Aug. 25, 2005;353(8):811-22.

(56) References Cited

OTHER PUBLICATIONS

Schedin et al., Mammary gland ECM remodeling, stiffness, and mechanosignaling in normal development and tumor progression. Cold Spring Harb Perspect Biol. Jan. 1, 2011;3(1):a003228. doi: 10.1101/cshperspect.a003228.

Schröder et al., The mammalian unfolded protein response. Annu Rev Biochem. 2005;74:739-89.

Shi et al., Identification and characterization of pancreatic eukaryotic initiation factor 2 alpha-subunit kinase, PEK, involved in translational control. Mol Cell Biol. Dec. 1998;18(12):7499-509.

Sidrauski et al., The unfolded protein response: an intracellular signalling pathway with many surprising features. Trends Cell Biol. Jun. 1998;8(6):245-9.

Subramanian et al., Gene set enrichment analysis: a knowledge-based approach for interpreting genome-wide expression profiles. Proc Natl Acad Sci U S A. Oct. 25, 2005;102(43):15545-50. Epub Sep. 30, 2005.

Taube et al., Core epithelial-to-mesenchymal transition interactome gene-expression signature is associated with claudin-low and metaplastic breast cancer subtypes. Proc Natl Acad Sci U S A. Aug. 31, 2010;107(35):15449-54. doi: 10.1073/pnas.1004900107. Epub Aug. 16, 2010. Erratum in: Proc Natl Acad Sci U S A. Nov. 2, 2010;107(44):19132.

Tsai et al., The Unfolded Protein Response, Degradation from Endoplasmic Reticulum and Cancer. Genes Cancer. Jul. 1, 2010;1(7):764-778.

Valdés et al., The epithelial mesenchymal transition confers resistance to the apoptotic effects of transforming growth factor Beta in fetal rat hepatocytes. Mol Cancer Res. Nov. 2002;1(1):68-78.

Van Nes et al., Co-expression of SNAIL and TWIST determines prognosis in estrogen receptor-positive early breast cancer patients. Breast Cancer Res Treat. May 2012;133(1):49-59. doi: 10.1007/s10549-011-1684-y. Epub Jul. 28, 2011.

Vellanki et al., OASIS/CREB3L1 induces expression of genes involved in extracellular matrix production but not classical endoplasmic reticulum stress response genes in pancreatic beta-cells. Endocrinology. Sep. 2010;151(9):4146-57. doi:10.1210/en.2010-0137. Epub Jul. 28, 2010.

Walter et al., The unfolded protein response: from stress pathway to homeostatic regulation. Science. Nov. 25, 2011;334(6059):1081-6. doi: 10.1126/science.1209038.

Woodward et al., WNT/beta-catenin mediates radiation resistance of mouse mammary progenitor cells. Proc Natl Acad Sci U S A. Jan. 9, 2007;104(2):618-23. Epub Jan. 3, 2007. Erratum in: Proc Natl Acad Sci U S A. Apr. 24, 2007;104(17):7307.

Wouters et al., Hypoxia signalling through mTOR and the unfolded protein response in cancer. Nat Rev Cancer. Nov. 2008;8(11):851-64. doi: 10.1038/nrc2501. Epub Oct. 10, 2008.

Zhang et al., The Perk eukaryotic initiation factor 2 alpha kinase is required for the development of the skeletal system, postnatal growth, and the function and viability of the pancreas. Mol Cell Biol. Jun. 2002;22(11):3864-74.

Zinszner et al., CHOP is implicated in programmed cell death in response to impaired function of the endoplasmic reticulum. Genes Dev. Apr. 1, 1998;12(7):982-95.

* cited by examiner

CMP302

CMP308

DEV4

| | Gene Set Enriched | p-value |
|---|---|---|
| 1 | CARBOHYDRATE_TRANSPORT | 0.014 |
| 2 | COLLAGEN | 0.017 |
| 3 | EXTRACELLULAR_MATRIX_PART | 0.019 |
| 4 | PROTEIN_HETERODIMERIZATION_ACTIVITY | 0.03 |
| 5 | AMINO_ACID_DERIVATIVE_METABOLIC_PROCESS | 0.035 |
| 6 | EXTRINSIC_TO_MEMBRANE | 0.041 |
| 7 | AMINE_CATABOLIC_PROCESS | 0.042 |
| 8 | NEG_REGULATION_OF_POL_II_PROMOTER | 0.042 |
| 9 | NITROGEN_COMPOUND_CATABOLIC_PROCESS | 0.044 |
| 10 | HORMONE_ACTIVITY | 0.044 |
| 11 | EXTRACELLULAR_MATRIX | 0.044 |
| 12 | SECRETED_CYTOKINES_CHEMOKINES | 0.046 |
| 13 | PROTEINACEOUS_EXTRACELLULAR_MATRIX | 0.046 |

FIG. 2E

| | Gene Set Definition | p-value |
|---|---|---|
| 1 | REGULATION_OF_CDK_ACTIVITY | 0 |
| 2 | MITOSIS | 0 |
| 3 | REGULATION_OF_MITOSIS | 0.001 |
| 4 | M_PHASE_OF_MITOTIC_CELL_CYCLE | 0.001 |
| 5 | M_PHASE | 0.001 |
| 6 | REGULATION_OF_PROTEIN_KINASE_ACTIVITY | 0.002 |
| 7 | REGULATION_OF_KINASE_ACTIVITY | 0.002 |
| 8 | ENDOPLASMIC_RETICULUM | 0.002 |
| 9 | CELL_CYCLE_PHASE | 0.003 |
| 10 | REGULATION_OF_TRANSFERASE_ACTIVITY | 0.004 |
| 11 | CELL_CYCLE_PROCESS | 0.006 |
| 12 | MITOTIC_CELL_CYCLE | 0.007 |
| 13 | REGULATION_OF_CELL_CYCLE | 0.007 |
| 14 | SMALL_GTPASE_REGULATOR_ACTIVITY | 0.011 |
| 15 | GUANYL_NUC_EXCHANGE_FACTOR_ACTIVITY | 0.012 |
| 16 | GOLGI_APPARATUS | 0.013 |
| 17 | RNA_BINDING | 0.016 |

| | Gene Set Definition | p-value |
|---|---|---|
| 18 | MEMBRANE_LIPID_BIOSYNTHETIC_PROCESS | 0.017 |
| 19 | CELL_CYCLE_GO_0007049 | 0.018 |
| 20 | REGULATION_OF_CATALYTIC_ACTIVITY | 0.021 |
| 21 | GLYCEROPHOSPHOLIPID_METABOLIC_PROCESS | 0.022 |
| 22 | REGULATION_OF_MOLECULAR_FUNCTION | 0.024 |
| 23 | MEMBRANE_FRACTION | 0.024 |
| 24 | UDP_GLYCOSYLTRANSFERASE_ACTIVITY | 0.026 |
| 25 | GTPASE_REGULATOR_ACTIVITY | 0.03 |
| 26 | ENDOPLASMIC_RETICULUM_PART | 0.032 |
| 27 | ENDOPLASMIC_RETICULUM_MEMBRANE | 0.037 |
| 28 | TRANSFERRING_HEXOSYL_GROUPS | 0.043 |
| 29 | CYTOPLASMIC_VESICLE_PART | 0.044 |
| 30 | NUCLEAR_ENVELOPE_ER_NETWORK | 0.045 |
| 31 | PHOSPHOLIPID_METABOLIC_PROCESS | 0.045 |
| 32 | LIPID_BIOSYNTHETIC_PROCESS | 0.048 |
| 33 | CYTOPLASMIC_VESICLE_MEMBRANE | 0.049 |

FIG. 2F

SEQUENCE LISTING

<160> NUMBER OF SEQ ID NOS: 3

<210> SEQ ID NO 1
<211> LENGTH: 67
<212> TYPE: DNA
<213> ORGANISM: Artificial Sequence
<220> FEATURE:
<223> OTHER INFORMATION: Synthetic oligonucleotide

```
<400> SEQUENCE: 1
aatgatacgg cgaccaccga gaaagtattt cgatttcttg gctttatata tcttgtggaa      60
ctgacga                                                               67

<210> SEQ ID NO 2
<211> LENGTH: 66
<212> TYPE: DNA
<213> ORGANISM: Artificial Sequence
<220> FEATURE:
<223> OTHER INFORMATION: Synthetic oligonucleotide

<400> SEQUENCE: 2
caagcagaag acggcatacg agctcttccg atcttgtgga tgaatactgc catttgtctc      60
gaggtc                                                                66

<210> SEQ ID NO 3
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 3
gagaaagtat ttcgatttct tggctttata tatcttgtgg a                         41
```

ER-STRESS INDUCING COMPOUNDS AND METHODS OF USE THEREOF

RELATED APPLICATIONS

This application claims priority under 35 U.S.C. §119(e) from U.S. Provisional Application Ser. No. 61/716,112 having a filing date of Oct. 19, 2012 and entitled "ER-STRESS INDUCING COMPOUNDS AND METHODS OF USE THEREOF," the contents of which are incorporated herein in their entirety by reference.

FIELD OF THE INVENTION

The invention relates to methods for identifying compounds that target cancer stem cells. In some aspects, the invention relates to treatment methods that use compounds that specifically target cancer stem cells for inhibiting the growth and/or survival of cancer stem cells in a subject in need thereof. Other aspects of the invention relate to the use of cancer stem cell biomarkers in the selection of a treatment for inhibiting the growth and/or survival of cancer stem cells in a subject in need thereof.

BACKGROUND OF INVENTION

The differentiation states of cancer cells influence their malignant properties. Carcinoma cells lie along a continuum of less- and more-differentiated states. At one end of this continuum reside cancer cells that retain cell-to-cell adhesion contacts and express most epithelial markers. At the other end reside stem-like cells that have lost many epithelial markers; such cells frequently upregulate mesenchymal markers (e.g., VIM, SMA, FN1), and are said to have undergone an epithelial-to-mesenchymal transition (EMT).

Less differentiated cancers generally tend to be more malignant. This basic notion is reflected in the concept of tumor grade, which is a quantitative measure of cancer cell dedifferentiation. Low-grade tumors have differentiated cancer cells; they also have a better prognosis than high-grade tumors. This critical insight serves as the foundation of tumor pathology and prognosis. Differentiation-state distinctions do not only occur between tumors, but also between the cells of a single tumor.

When taken from the same tumor, cancer cells in distinct states can have very different functional properties. For instance, in comparison to other cells in the same tumor, cancer stem-like cells (CSCs) efficiently seed new tumors, invade host tissues, and survive without cell-to-cell or cell-to-matrix attachments. In breast epithelium, experimental induction of EMT is sufficient to generate normal and cancerous stem-like cells. This indicates that carcinoma cells can acquire most metastatic traits by modulating their differentiation state.

In clinical settings, metastatic ability alone is insufficient for tumor dissemination; cancer cells must also evade therapy. Two general patterns of resistance are commonly observed: acquired resistance occurs when cancers respond initially to therapy but then develop resistance over time; intrinsic resistance occurs when cancers fail to respond initially to therapy. Remarkably, in addition to having the metastatic traits described above, CSCs also exhibit intrinsic resistance to most therapies. Several mechanisms have been proposed for how CSCs and cancer cells following EMT evade therapy, including activation of PI3K, NFκB and EGFR signaling. However, basis for intrinsic therapeutic resistance and invasiveness of certain CSCs remains minimally understood.

SUMMARY OF INVENTION

Aspects of the invention disclosed herein are based on the discovery that ER-stress induction serves as a method to target and eradicate malignant cancer cell subpopulations. Some aspects of the invention are based on the discovery that cancer stem cells (CSCs) and cells that have undergone epithelial-to-mesenchymal transition (EMT) (also referred to as EMT cells) are sensitized to ER stress. According to some aspects of the invention it has been discovered that ER-stress inducing compounds are useful for treating tumors by selectively killing CSCs. In some embodiments, ER-stress inducing compounds disclosed herein are effective in shrinking tumors that contain either a significant representation of CSCs or highly secretory cancer cells. In some cases, available therapies or surgery can effectively de-bulk tumors; in these settings, ER-stress inducing compounds disclosed herein may be useful for purging individual cancer cells that have disseminated to secondary organs, but have not yet begun to form metastases; such dormant cancer cells may express CSC markers and have activated UPR signaling.

Further aspects of the invention disclosed herein are based on the development of methods for identifying ER-stress inducing compounds, e.g., small molecules stressors of endoplasmic reticulum function. According to some aspects of the invention methods are provided that may be used to quantify CSC proportions in tumors or other cell populations by assessing unfolded protein response (UPR) signaling pathways. According to other aspects of the invention, methods are provided for identifying patient subpopulations likely to respond to ER stress-inducing compounds therapies. According to some aspects of the invention methods are provided for assaying biomarkers that provide an indication of the responsiveness of tumors or cells to ER-inducing compounds.

Aspects of the invention relate to methods of inhibiting expansion of a tumor cell population (e.g., a population of cells from a carcinoma). In some embodiments, the methods comprise determining that the tumor cell population comprises cancer stem cells that are sensitive to endoplasmic reticulum (ER) stress; and contacting the tumor cell population with an ER-stress inducing compound. In some embodiments, the methods comprise obtaining a tumor cell population from a tumor (e.g., a carcinoma, e.g., a breast carcinoma) of a subject. In some embodiments, the ER-stress inducing compound is a compound that selectively kills cancer cells that are resistant to a traditional chemotherapeutic compound. In some embodiments, the traditional chemotherapeutic compound is a spindle poison, optionally which is paclitaxel, or a DNA replication inhibitor, optionally which is doxorubicin. In some embodiments, the cancer stem cells that are sensitive to ER stress exhibit one or more characteristics of a cell that has undergone an epithelial-to-mesenchymal transition (EMT). In some embodiments, the ER-stress inducing compound is a compound of Formula (I):

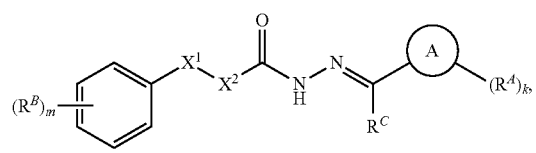

(I)

or a pharmaceutically acceptable salt thereof,
wherein:
Ring A is a substituted or unsubstituted aryl ring, or substituted or unsubstituted heteroaryl ring;
each instance of $R^A$ is independently hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{A1}$, —$N(R^{A1})_2$, —$SR^{A1}$, —CN, —SCN, —C(=$NR^{A1}$)

$R^{A1}$, —C(=NR$^{A1}$)OR$^{A1}$, —C(=NR$^{A1}$)N(R$^{A1}$)$_2$, —C(=O)R$^{A1}$, —C(=O)OR$^{A1}$, —C(=O)N(R$^{A1}$)$_2$, —NO$_2$, —NR$^{A1}$C(=O)R$^{A1}$, —NR$^{A1}$C(=O)OR$^{A1}$, —NR$^{A1}$C(=O)N(R$^{A1}$)$_2$, —OC(=O)R$^{A1}$, —OC(=O)OR$^{A1}$, —OC(=O)N(R$^{A1}$)$_2$, or a nitrogen protecting group when attached to a nitrogen atom, or optionally two R$^A$ groups are joined to form a substituted or unsubstituted carbocyclic, substituted or unsubstituted heterocyclic, substituted or unsubstituted aryl, or substituted or unsubstituted heteroaryl ring;

each instance of R$^{A1}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or optionally two R$^{A1}$ groups are joined to form a substituted or unsubstituted heterocyclic ring;

k is 0, 1, 2, 3, 4, or 5;

each instance of R$^B$ is independently hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^{B1}$, —N(R$^{B1}$)$_2$, —SR$^{B1}$, —CN, —SCN, —C(=NR$^{B1}$)R$^{B1}$, C(=NR$^{B1}$)OR$^{B1}$, —C(=NR$^{B1}$)N(R$^{B1}$)$_2$, —C(=O)R$^{B1}$, —C(=O)OR$^{B1}$, —C(=O)N(R$^{B1}$)$_2$, —NO$_2$, —NR$^{B1}$C(=O)R$^{B1}$, —NR$^{B1}$C(=O)OR$^{B1}$, —NR$^{B1}$C(=O)N(R$^{B1}$)$_2$, —OC(=O)R$^{B1}$, —OC(=O)OR$^{B1}$, or —OC(=O)N(R$^{B1}$)$_2$, or optionally two R$^B$ groups are joined to form a substituted or unsubstituted carbocyclic, substituted or unsubstituted heterocyclic, substituted or unsubstituted aryl, or substituted or unsubstituted heteroaryl ring;

each instance of R$^{B1}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or optionally two R$^{B1}$ groups are joined to form a substituted or unsubstituted heterocyclic ring;

m is 0, 1, 2, 3, 4, or 5;

R$^C$ is hydrogen or C$_{1-6}$ alkyl;

X$^1$ and X$^2$ are each independently —O—, —S—, —NR$^D$—, —C(R$^E$)$_2$—, or —C(=C(R$^E$)$_2$)—;

R$^D$ is is hydrogen, C$_{1-6}$ alkyl, or a nitrogen protecting group, or optionally R$^D$ and one R$^B$ group are joined to form a substituted or unsubstituted heterocyclic ring; and each instance of R$^E$ is independently hydrogen, halogen, or C$_{1-6}$ alkyl, or optionally two R$^E$ groups are joined to form a substituted or unsubstituted carbocyclic ring, or optionally one R$^E$ group and one R$^B$ group are joined to form a substituted or unsubstituted carbocyclic ring, substituted or unsubstituted heterocyclic ring, substituted or unsubstituted aryl ring, or substituted or unsubstituted heteroaryl ring. In some embodiments, Ring A is substituted or unsubstituted, 5-membered, monocyclic heteroaryl. In some embodiments, R$^B$ is halogen, C$_{1-6}$ alkyl, —OR$^{B1}$, or —CN, or two R$^B$ groups are joined to form a substituted or unsubstituted heterocyclic ring, or substituted or unsubstituted aryl ring. In some embodiments, X$^1$ and X$^2$ are each —CHR$^E$—; and two R$^E$ groups are joined to form a substituted or unsubstituted carbocyclic ring. In some embodiments, X$^1$ is —O—, —S—, or —NR$^D$—; and X$^2$ is —CH$_2$— or —CHR$^E$—. In some embodiments, X$^1$ is —O—, —S—, or —NR$^D$—; X$^2$ is —CHR$^E$— or —C(=CHR$^E$)—; and R$^E$ and one R$^B$ group are joined to form a substituted or unsubstituted heterocyclic ring, or substituted or unsubstituted heteroaryl ring. In some embodiments, the ER-stress inducing compound is of the formula:

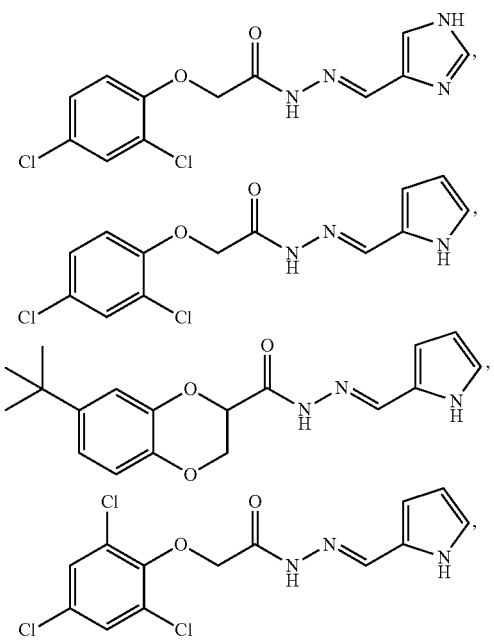

or a pharmaceutically acceptable salt thereof. In some embodiments, the ER-stress inducing compound is selected from: DTT, A23187, thapsigargin and tunicamycin. In some embodiments, the ER-stress inducing compound is selectively toxic to cells that have undergone an EMT, or identified in a screen for compounds that are selectively toxic to cells that have undergone an EMT.

According to other aspects of the invention methods of characterizing a test compound are provided. In some embodiments, the methods comprise (a) contacting epithelial-derived mesenchymal stem-like cells with a test compound; (b) determining that the extent of growth or proliferation of the epithelial-derived mesenchymal stem-like cells that have been contacted with the test compound is lower than the extent of growth or proliferation of epithelial-derived mesenchymal stem-like cells that have not been contacted with the test compound; and (c) selecting the test compound as a candidate ER-stress inducing compound based on the results of step (b).

According to other aspects of the invention methods of characterizing a test compound are provided. In some embodiments, the methods comprise (a) contacting epithelial-derived mesenchymal stem-like cells with a test compound; (b) determining that the extent of survival of the epithelial-derived mesenchymal stem-like cells that have been contacted with the test compound is lower than the extent of survival of epithelial-derived mesenchymal stem-like cells that have not been contacted with the test compound; and (c) selecting the test compound as a candidate ER-stress inducing compound based on the results of step (b).

In some embodiments, the method comprise obtaining the epithelial-derived mesenchymal stem-like cells from a subject. In some embodiments, the method comprise obtaining the epithelial-derived mesenchymal stem-like cells from a subject. In some embodiments, the methods comprise determining whether modulation of expression of a gene within the gene set listed in FIG. 3E, increases the extent of survival of epithelial-derived mesenchymal stem-like cells that have been contacted with the test compound, wherein an increase in the extent of survival identifies the test compound as an ER-stress inducing compound. In some embodiments, the methods comprise determining whether inhibition of expression of plasminogen activator inhibitor 1 (PAI1) or fibronectin (FN1) increases the extent of survival of epithelial-derived mesenchymal stem-like cells that have been contacted with the test compound, wherein an increase in the extent of survival identifies the test compound as an ER-stress inducing compound. In some embodiments, the methods comprise determining whether modulation of expression of a gene within the gene set listed in FIG. 3F, decreases the extent of survival of epithelial-derived mesenchymal stem-like cells that have been contacted with the test compound, wherein a decrease in the extent of survival identifies the test compound as an ER-stress inducing compound. In some embodiments, the methods comprise determining whether contact with the test compound results in an increase in unfolded protein response (UPR) signaling in the epithelial-derived mesenchymal stem-like cells, wherein an increase in the extent of UPR signaling identifies the test compound as an ER-stress inducing compound. In certain embodiments, UPR signaling is assessed by determining the extent of XBP1-mediated splicing, wherein an increase in the extent of XBP1-mediated splicing as a result of contact with the test compound indicates an increase in UPR signaling. In certain embodiments, UPR signaling is assessed by determining the extent of eIF2α phosphorylation, wherein an increase in the extent of eIF2α phosphorylation as a result of contact with the test compound indicates an increase in UPR signaling. In certain embodiments, UPR signaling is assessed by determining the extent of ATF6 activation, wherein an increase in the extent of ATF6 activation as a result of contact with the test compound indicates an increase in UPR signaling. In certain embodiments, UPR signaling is assessed by determining the extent of CHOP, Bip, calnexin or GRP94 expression, wherein an increase in the extent of CHOP, Bip, calnexin or GRP94 expression as a result of contact with the test compound indicates an increase in UPR signaling. In certain embodiments, UPR signaling is assessed by determining the extent of phosphorylation of protein kinase RNA-like endoplasmic reticulum kinase (PERK), wherein an decrease in the extent of phosphorylation of PERK as a result of contact with the test compound indicates an increase in UPR signaling. In some embodiments, the methods comprise determining whether contact with the test compound results in an increase in UPR signaling in the epithelial-derived mesenchymal stem-like cells at a lower dose than in epithelial cells, wherein a comparable increase in UPR signaling occurring at a lower dose in epithelial-derived mesenchymal stem-like cells than in epithelial cells indicates an increase in UPR signaling that is selective for epithelial-derived mesenchymal stem-like cells.

In certain embodiments, epithelial-derived mesenchymal stem-like cells secrete increased quantities of extracellular proteins compared with epithelial cells. In certain embodiments, epithelial-derived mesenchymal stem-like cells express CREB3L1 at a higher level compared with epithelial cells. In certain embodiments, epithelial-derived mesenchymal stem-like cells express, at a higher level compared with epithelial cells, one or more genes selected from: SARA1, Sec24D, Sec23A, KDELR3, Sec13L1, Sec61A1, Sec61A2, COPZ2, Sec14L1, Sec14L2, COPB2, TRAM2, COPG, ARCN1, Sec31L1, TRAM1, SRPRB, SRP54, Sec24A and KDELR1. In certain embodiments, epithelial-derived mesenchymal stem-like cells are epithelial cells that have undergone an epithelial-to-mesenchymal transition (EMT). In certain embodiments, EMT is stimulated by exposure to TGF-beta ligand; an EMT stimulated by overexpression of Twist, Snail or Goosecoid; or an EMT stimulated by inhibition of E-cadherin.

In some embodiments, epithelial-derived mesenchymal stem-like cells of the invention are epithelial cells that have adhered to a substratum following growth in suspension for a period of at least 12 hours. In certain embodiments, epithelial-derived mesenchymal stem-like cells express CD44 at relatively high levels and express CD24 at relatively low levels compared with the levels of expression of CD44 and CD24 in epithelial cells. In certain embodiments, epithelial-derived mesenchymal stem-like cells express fibronectin at relatively high levels compared with the level of expression of fibronectin in epithelial cells. In certain embodiments, epithelial-derived mesenchymal stem-like cells express cytokeratin 8/18 at relatively low levels compared with the level of expression of cytokeratin 8/18 in epithelial cells. In certain embodiments, epithelial-derived mesenchymal stem-like cells express E-cadherin at relatively low levels compared with the level of expression of E-cadherin in epithelial cells.

According to other aspects of the invention, methods of characterizing cancer cells of a carcinoma are provided. In some embodiments, the methods comprise conducting an assay to determine the extent of unfolded protein response (UPR) signaling in the cancer cells. In some embodiments of the methods, the extent of UPR signaling in the cancer cells is indicative of the extent of susceptibility of the cancer cells to ER-stress induced cell death. According to other aspects of the invention, methods of detecting cancer stem cells in a carcinoma are provided that comprise conducting an assay to determine the extent of UPR signaling in cells of a carcinoma; and detecting cancer stem cells in the carcinoma based on the extent of UPR signaling, wherein cancer stem cells exhibit higher levels of UPR signaling than non-cancer stem cells in the tumor. According to other aspects of the invention, methods of evaluating the prognosis of a subject having a carcinoma are provided that comprise conducting an assay to determine the extent of UPR signaling in cells of the tumor, wherein the extent of UPR signaling in the cells being higher that the extent of UPR signaling in normal epithelial cells indicates that the subject has a poor prognosis. In some embodiments, the methods comprise obtaining the carcinoma from a subject. In some embodiments, the results of the assay of UPR signaling indicate the extent of XBP1-mediated splicing in the cancer cells, and the extent of XBP1-mediated splicing is directly related to the extent of UPR signaling. In some embodiments, the results of the assay indicate the extent of eIF2α phosphorylation in the cancer cells, and the extent of eIF2α phosphorylation is directly related to the extent of UPR signaling. In some embodiments, the results of the assay indicate the extent of ATF6 activation in the cancer cells, and the extent of ATF6 activation is directly related to the extent of UPR signaling. In some embodiments, the results of the assay indicate the extent of CHOP, Bip, calnexin or GRP94 expression in the cancer cells, and the extent of CHOP, Bip, calnexin or GRP94 expression is directly related to the extent of UPR signaling. In some embodiments, the results of the assay indicate the extent of phosphorylation of protein kinase RNA-like endoplasmic reticulum kinase (PERK) in the cancer cells, and the extent of phosphorylation of PERK is inversely related to the extent of UPR signaling. In some embodiments, the results of the assay indicate the extent of phosphorylation of IRE1a and/or IRE1b in the cancer cells, and the extent of phosphorylation of IRE1a and/or IRE1b is related to the extent of UPR signaling.

According to other aspects of the invention, methods of selecting a treatment for a subject having a carcinoma are provided. In some embodiments, the methods comprise conducting an assay to determine the extent of UPR signaling in cells of the carcinoma, wherein, if the extent of UPR signaling in the cells of the tumor is higher than the extent of UPR signaling in cells from normal epithelium, then an ER-stress inducing compound is suitable for treating the subject, and if the extent of UPR signaling in the cells of the tumor is equal to or less than the extent of UPR signaling in cells from normal epithelium, then an ER-stress inducing compound is not suitable for treating the subject; and selecting a treatment for the subject based at least in part on the results of the assay. In some embodiments, the extent of UPR signaling in the cells of the tumor is higher than the extent of UPR signaling in cells from normal epithelium, and the method further comprises treating the subject with an ER-stress inducing compound based on the results of the assay. In some embodiments, the cells of the carcinoma are cancer stem cells. In some embodiments, the extent of UPR signaling is directly related to the secretory load on the cells.

In some embodiments, a proteasome inhibitor, Hsp90 inhibitor, Grp78 inhibitor, or ADP-ribosylation factor inhibitor may be used to stress ER function. In some embodiments, a treatment that stresses ER function involves administering to a subject a proteasome inhibitor, Hsp90 inhibitor, Grp78 inhibitor, or ADP-ribosylation factor inhibitor.

Accordingly, in some embodiments, methods are provided for selecting a treatment for a subject having a carcinoma, in which the methods involve conducting an assay to determine the extent of UPR signaling in cells of the carcinoma, in which, if the extent of UPR signaling in the cells of the carcinoma is higher than the extent of UPR signaling in cells from normal epithelium, then a proteasome inhibitor is suitable for treating the subject, and if the extent of UPR signaling in the cells of the carcinoma is equal to or less than the extent of UPR signaling in cells from normal epithelium, then a proteasome inhibitor is not suitable for treating the subject; and selecting a treatment for the subject based at least in part on the results of the assay. Thus, in some embodiments, the methods further involve administering one or more proteasome inhibitors to the subject for treating the carcinoma based at least in part on the results of the assay. In some embodiments, the proteasome inhibitor is Bortezomib, Nelfinavir, Atazanavir, or Carfilzomib.

In some embodiments, methods are provided for selecting a treatment for a subject having a carcinoma, in which the methods involve conducting an assay to determine the extent of UPR signaling in cells of the carcinoma, in which, if the extent of UPR signaling in the cells of the carcinoma is higher than the extent of UPR signaling in cells from normal epithelium, then a Hsp90 inhibitor is suitable for treating the subject, and if the extent of UPR signaling in the cells of the carcinoma is equal to or less than the extent of UPR signaling in cells from normal epithelium, then a Hsp90 inhibitor is not suitable for treating the subject; and selecting a treatment for the subject based at least in part on the results of the assay. Thus, in some embodiments, the methods further involve administering one or more Hsp90 inhibitors to the subject for treating the carcinoma based at least in part on the results of the assay. In some embodiments, the Hsp90 inhibitor is Geldanamycin, Radicicol, or 17AAG.

In some embodiments, methods are provided for selecting a treatment for a subject having a carcinoma, in which the methods involve conducting an assay to determine the extent of UPR signaling in cells of the carcinoma, in which, if the extent of UPR signaling in the cells of the carcinoma is higher than the extent of UPR signaling in cells from normal epithelium, then a Grp78 inhibitor is suitable for treating the subject, and if the extent of UPR signaling in the cells of the carcinoma is equal to or less than the extent of UPR signaling in cells from normal epithelium, then a Grp78 inhibitor is not suitable for treating the subject; and selecting a treatment for the subject based at least in part on the results of the assay. Thus, in some embodiments, the methods further involve administering one or more Grp78 inhibitors to the subject for treating the carcinoma based at least in part on the results of the assay. In some embodiments, an Grp78 inhibitor is Versipelostatin.

In some embodiments, methods are provided for selecting a treatment for a subject having a carcinoma, in which the methods involve conducting an assay to determine the extent of UPR signaling in cells of the carcinoma, in which, if the extent of UPR signaling in the cells of the carcinoma is higher than the extent of UPR signaling in cells from normal epithelium, then a ADP-ribosylation factor inhibitor is suitable for treating the subject, and if the extent of UPR signaling in the cells of the carcinoma is equal to or less than the extent of UPR signaling in cells from normal epithelium, then a ADP-ribosylation factor inhibitor is not suitable for treating the subject; and selecting a treatment for the subject based at least in part on the results of the assay. Thus, in some embodiments, the methods further involve administering one or more ADP-ribosylation factor inhibitors to the subject for treating the carcinoma based at least in part on the results of the assay. In some embodiments, an ADP-ribosylation factor inhibitor is Brefeldin A.

According to other aspects of the invention, methods of evaluating effectiveness of a treatment for a subject having a carcinoma are provided. In some embodiments, the methods comprise conducting an assay prior to the treatment to determine the extent of activation of a UPR pathway (e.g., a UPR pathway selected from: PERK, IRE1a, and ATF6); and conducting an assay after the treatment to determine the extent of activation of the UPR pathway, wherein the treatment is effective if the UPR pathway has a higher extent of activation after the treatment compared with its extent of activation prior to the treatment. In some embodiments, the treatment is administration of an ER-stress inducing compound.

According to other aspects of the invention, methods of determining the responsiveness of a carcinoma to a treatment that stresses ER function. In some embodiments, the methods comprise conducting an assay prior to the treatment to determine if one or more UPR signaling pathways is active in cells of the carcinoma; and if only a subset of UPR signaling pathways are active in the cells, utilizing the remaining UPR signaling pathways as biomarkers of the responsiveness of the carcinoma to the treatment. In some embodiments, if it is determined that PERK signaling is active prior to the treatment, then the methods further comprises assessing the activity of IRE1a, IRE1b and/or ATF6 signaling pathways as biomarkers of responsiveness. In some embodiments, if it is determined that IRE1a signaling is active prior to the treatment, then the methods further comprises assessing the activity of PERK, IRE1b and/or ATF6 signaling pathways as biomarkers of responsiveness. In some embodiments, if it is determined that IRE1b signaling is active prior to the treatment, then the methods further comprises assessing the activity of PERK, ATF6, and/or IRE1a signaling pathways as biomarkers of responsiveness. In some embodiments, if it is determined that ATF6 signaling is active prior to the treatment, then the methods further comprises assessing the activity of PERK, IRE1b and/or IRE1a signaling pathways as biomarkers of responsiveness. In some embodiments, if it is determined that IRE1a and PERK signaling is active prior to the treatment, then the methods further comprises assessing the activity of IRE1b and/or ATF6 signaling pathways as biomarkers of responsiveness. In some embodiments, if it is determined that IRE1b and/or ATF6 signaling is active prior to the treatment, then the methods further comprises assessing the activity of IRE1a and/or PERK signaling pathways as biomarkers of responsiveness. In some embodiments, the method further comprise subjecting the carcinoma to a treatment that stresses ER function.

According to other aspects of the invention, methods of quantifying cancer stem cells (CSCs) are provided. In some embodiments, the methods comprise obtaining cells from a carcinoma; and assessing the proportion of the cells from the carcinoma that have activated PERK-eIF2alpha-ATF4 signaling, wherein the proportion of the cells that have activated PERK-eIF2alpha-ATF4 is related to the proportion of cells in the carcinoma that are CSCs. In some embodiments, the step of assessing comprising determining the proportion of cells that express one or more downstream unfolded protein response proteins. In some embodiments, the unfolded protein response proteins are selected from BIP (HSPA5), calnexin and GRP94. In some embodiments, a relatively high proportion of CSCs in the carcinoma indicates a poor prognosis for a subject having the carcinoma. In some embodiments, a relatively high proportion of CSCs in the carcinoma indicates that the carcinoma is resistant to a standard chemotherapeutic, is an invasive carcinoma, and/or has relatively high probability of progressing to metastatic disease.

Figure 1A:
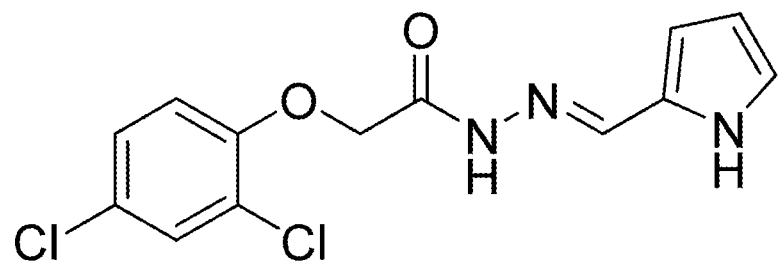
FIGS. 1A-J. Characterization of small molecules with selective toxicity towards IDMS cells.
Figure 1A:
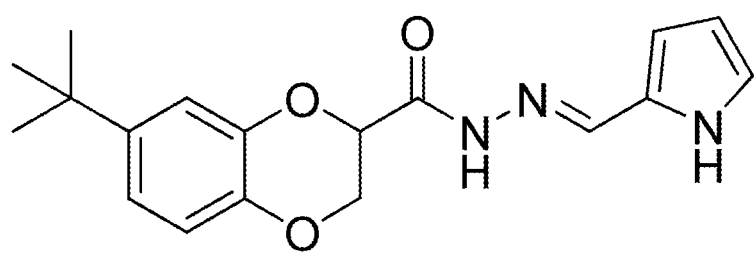
Figure 1A:
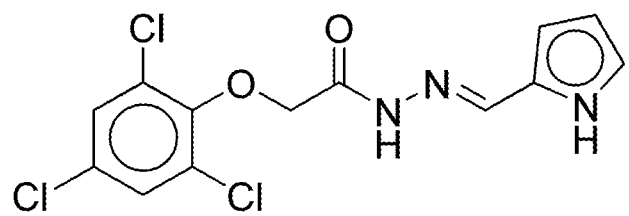

(A) Structure of three IDMS-selective small molecules, Cmp302, Cmp308 and Dev4.

(B) Dose response curves of HMLE_shGFP, HMLE_shEcad and HMLE_Twist cells treated with various concentrations of Cmp302, Cmp308 and Dev4, respectively for 3 days. Cell survival was determined using an ATP-based luminescence assay.

(C) The assays in (B) performed on HMLER cells.

(D) Representative fluorescence images of HMLE_shGFP_dsRed and HMLE_Twist_GFP cells were mixed in a 1:1 ratio and treated with 5 nM Paclitaxel, 2 μM Cmp302, 2 μM Cmp308 or DMSO control. Images after 5 days of treatment are shown. Scale bar: 50 μm (E) Quantification of HMLE_shGFP_dsRed and HMLE_shEcad_GFP cells that were mixed in a 1:1 ratio and treated with Doxorubicin or Dev4. Following a 5 day treatment, the percentages of dsRed-positive and GFP-positive cells were quantified by FACS.

(F) Representative fluorescence images of MDA-MB-157 cells cultured either under suspension conditions for 36 h and transferred onto adherent cell culture plates for 24 h, or maintained in standard adherent cell culture. Cells were stained using FITC-conjugated phalloidin to visualize F-actin fibers. Scale bar: 50 μm (G) Western blot analysis of epithelial (CK8/18, E-cadherin) and mesenchymal (Fibronectin) markers of cell lysates from HMLER_shCtrl, HMLER_Twist and MDA-MB-157 cells grown under either adherent or suspension conditions.

(H) Flow cytometric analysis with CD24 and CD44 antibodies of MDA-MB-157 cells cultured under either adherent or suspension conditions for 36 h.

(I) Dose-response curves of MDA-MB-157 cells cultured in adherent or suspension conditions and treated with 8 doses of paclitaxel, Cmp302 or Cmp308 for 3 days. Cell survival was determined using an ATP-based luminescence assay.

(J) MDA-MB-157 cells were treated with Cmp308, paclitaxel or DMSO solvent in suspension for 36 h and analyzed by flow cytometry for CD44 and CD24 expression. The percentage of $CD44^{hi}CD24^{lo}$ and $CD44^{lo}CD24^{hi}$ cells in were quantified and normalized relative to DMSO controls.

FIGS. 2A-F. Genome-wide shRNA screen to identify genetic interactions with Cmp302 in IDMS cells.

(A) Schematic of pooled shRNA screen design.

(B) Estimation of normalized shRNA read densities in shRNA-infected populations treated with either DMSO (N=4) or Cmp302 (N=2).

(C) Bivariate scatterplot of shRNA representations in the DMSO- and Cmp302-treated populations. Each point denotes a single shRNA and is colored according to whether its representation is enriched in the DMSO (red) or Cmp302 (green) treatment condition or not enriched between conditions (gray).

(D) Calculation of gene-level enrichment scores from the normalized shRNA read data. RIGER analysis with a Komogorov-Smirnov test statistic corresponding to a weighted sum of the first two ranked hairpins was used to compute gene-level scores (see experimental details).

(E) Gene sets whose inhibition resulted in resistance to Cmp302-induced death at a p<0.05 level of significance.

(F) Gene sets whose inhibition sensitized to Cmp302-induced death at a p<0.05 level of significance.

FIGS. 3A-E. IDMS cells are sensitized to chemical inducers of ER stress.

(A) Expression of UPR pathway components in HMLER_shGFP and HMLER_Twist cells that were treated with Dev2, Cmp302, Dev4 or DMSO solvent for 6 h. Western blot analysis for phospho-eIF2α, total eIF2α, CHOP and β-Tubulin. RT-PCR analysis of XBP1 and XBP1 splice variant and GAPDH transcripts.

(B) Dose-response curves of HMLE_shGFP, HMLE_shEcad and HMLE_Twist cells treated with various concentrations of Thapsigargin, DTT and A23187 for 3 days. Cell survival was determined using an ATP-based luminescence assay.

(C) Dose-response curves of HMLER_shGFP, HMLER_shEcad and HMLER_Twist cells treated with various concentrations of Thapsigargin, DTT and A23187 for 3 days. Cell survival was determined using an ATP-based luminescence assay.

(D) Western blot analysis of HMLER_shGFP and HMLER_Twist cells treated with vehicle (DMSO), DTT or A23187 for 4 h and probed for p-eIF2α, total eIF2α, CHOP and β-Tubulin (loading control). RT-PCR analysis of XBP1 and XBP1 splice variant and GAPDH transcripts.

(E) Western blot analysis of HMLER_shGFP and HMLER_Twist cells treated with vehicle (DMSO), Tunicamycin or Thapsigargin for 4 h and probed for p-eIF2α, total eIF2α, CHOP and β-Tubulin (loading control). RT-PCR analysis of XBP1 and XBP1 splice variant and GAPDH transcripts.

FIGS. 4A-H. IDMS cells are highly secretory (A) Gene Set Enrichment Analysis of genes differentially expressed between control cells and cells induced into an IDMS state with Gsc, shEcad, Snail, TGFb or Twist expression vectors. The analysis indicates a strong overexpression of ECM and Collagen genes in IDMS cells.

(B) Expression of twelve genes encoding ECM proteins in IDMS cells (Gsc, shEcad, Snail, TGFb, Twist) relative to control epithelial cells.

(C) Network analysis of genes upregulated in IDMS cells relative to controls identifies over-expression of a network of secreted collagens and related matrix proteins.

(D) Log 2 fold-change in the expression of 22 secretory pathway component genes in cells induced into an IDMS state with Gsc, shEcad, Snail, TGFb or Twist relative to controls. The genes tested were CreB3L1, Creb3L2, and 20 Creb3L1 targeted genes, including SARA1, Sec24D, Sec23A, KDELR3, Sec13L1, Sec61A1, Sec61A2, COPZ2, Sec14L1, Sec14L2, COPB2, TRAM2, COPG, ARCN1, Sec31L1, TRAM1, SRPRB, SRP54, Sec24A and KDELR1.

(E) Confocal microscopy and quantification of Sec16-GFP localization to ER exit sites in IDMS (HMLE-shEcad) and control (HMLE-Ctrl) cells. Scale bar: 10 µm (F) Autoradiograph showing $^{35}$S-methionine/cysteine-labeled secreted proteins in IDMS (HMLE_shEcad, HMLE_Twist) and control (HMLE_shGFP) cells. Secreted proteins were harvested at the indicated time points. Quantification of signal in each lane is provided in arbitrary units. The indicated proteins were identified by mass-spectrometry.

(G) Expression of genes encoding secreted ECM proteins in a panel of Luminal (N=23, blue) and Basal-B (N=9, red) breast cancer lines.

(H) Autoradiograph showing $^{35}$S-methionine/cysteine-labeled secreted proteins in Luminal and Basal-B breast cancer lines. Quantification of signal in each lane is provided in arbitrary units.

FIGS. 5A-E. ECM secretion sensitizes IDMS cells to ER stressors and promotes cell migration (A) Western blot analysis showing stable shRNA-mediated knockdown of FN1 and PAI1 in HMLE_shEcad cells.

(B) shRNA-inhibited cells from (A) were mixed with control (shLuc) GFP-labeled HMLE_shEcad cells. The cell mixtures were treated with 4 µM Cmp308, 2 µM Dev4 or DMSO for 6 days and the proportion of both GFP positive and negative cells in the whole population was analyzed by FACS.

(C) Expression of UPR pathway components in HMLE_shEcad_shLuc and HMLE_shEcad_shFN1+PAI1 cells that were treated with Dev4, Thapsigargin or DMSO solvent for 6 h. Western blot analysis is shown for phospho-eIF2α, total eIF2α and β-Tubulin. RT-PCR analysis is shown for unspliced XBP1, spliced XBP1 and GAPDH transcripts.

(D) Morphology of HMLE_shEcad_shLuc and HMLE_shEcad_shFN1+PAI1 cells in culture.

(E) Migratory ability of HMLE_shEcad_shLuc and HMLE_shEcad_shFN1+PAI1 cells was measured with an in vitro wound-healing assay. Representative images and quantification at 0 and 7 hours post-wounding is shown.

FIGS. 6A-G. PERK-eIF2α signaling is activated in IDMS cells and modulates stress-induced death (A) Western blot analysis of IDMS or control immortalized and tumorigenic breast cancer lines for UPR pathway components with β-tubulin as a loading control.

(B) Cell lysates from control (HMLE_shGFP) and IDMS (HMLE_shEcad, HMLE_Twist) cells treated with or without thapsigargin were collected. The lysates were then treated with or without lambda-phosphatase and PERK protein expression was analyzed by Western blotting.

(C) Western blot analysis of protein lysates from luminal (MCF7, T47D, BT474, ZR-75-30) and Basal-B breast cancer cell lines (SUM159, MDA-MB-231, MDA-MB-157, Hs578T, BT549) for UPR pathway components with β-tubulin as a loading control.

(D) Western blot analysis of lysates from IDMS (CD44$^{hi}$CD24$^{lo}$) and non-IDMS (CD44$^{lo}$CD24$^{hi}$) subpopulations harvested by flow cytometry from HMLER and SUM149 breast cancer lines. Immunoblotting was performed for total eIF2α, p-eIF2α, Bip and β-tubulin.

(E) Western blot analysis of lysates from Hs578T and SUM159 cells stably infected with a control (scrambled) shRNA or an shRNA that inhibits PERK expression Immunoblotting was performed for PERK, p-eIF2α and β-tubulin.

(F) Relative viability of HMLER_shGFP and HMLER_Twist cells treated with increasing doses of thapsigargin in the presence or absence of 10 µM salubrinal for 3 days. Cell viability was assayed with an ATP-based luminescence assay.

(G) Western blot analysis of HMLER_shGFP and HMLER_Twist cells treated with increasing doses of thapsigargin in the presence or absence of 10 µM salubrinal for 4 hours prior to lysate harvest. Blots were probed for CHOP and β-tubulin (loading control).

FIGS. 7A-E. Induction of ER stress inhibits IDMS cell malignancy and expression of UPR and secretory pathway genes correlates with poor patient prognosis (A) Representative brightfield images and quantification of tumorsphere formation of SUM159 cancer cells treated with 5 nM Paclitaxel, 1 µg/ml Tunicamycin, 10 nM Thapsigargin, or DMSO vehicle for 3 days followed by another 3 days of recovery in regular medium. Scale bar: 50 µm (B) Representative images of crystal violet staining of SUM159 cells following transwell migration assay. Transwell migration assay was performed on SUM159 cancer cells treated as in (A). Cells that have migrated for 5 h following seeding into 8 µm pore inserts were visualize and quantified. Scale bar: 50 µm (C) Schematic diagram of experimental strategy of in vivo extravasation and survival assay. GFP labeled SUM159 cells (IDMS cells) were treated with vehicle (DMSO), 1 µg/ml Tunicamycin, or 10 nM Thapsigargin for 3 days followed by another 4 days of recovery in regular medium. 1×10$^6$ cells were injected into NOD/SCID mice via tail vein and lung tissues were harvested either 4 hour or 48 hour following injection. Representative images of mouse lung tissue stained for GFP by immunohistochemical analysis to identify and localize cancer cells. Quantification of GFP-positive cancer cells within lung tissues (N=4 per condition). Scale bar: 200 µm (D) Dose-response curves of SUM159 cells pre-treated as in (C) and then treated with 8 doses of paclitaxel or doxorubicin for 3 days. Cell survival was determined using an ATP-based luminescence assay.

(E) Kaplan-Meir relapse-free survival curves of patients (N=2,347) stratified into high (red) and low (black) expression by the median of the indicated genes. Hazard ratio (HR) and logrank p values are shown.

Figure 8A:
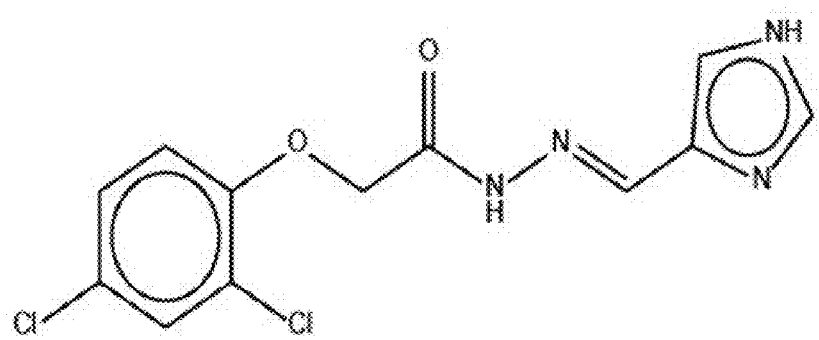
Figure 8B:
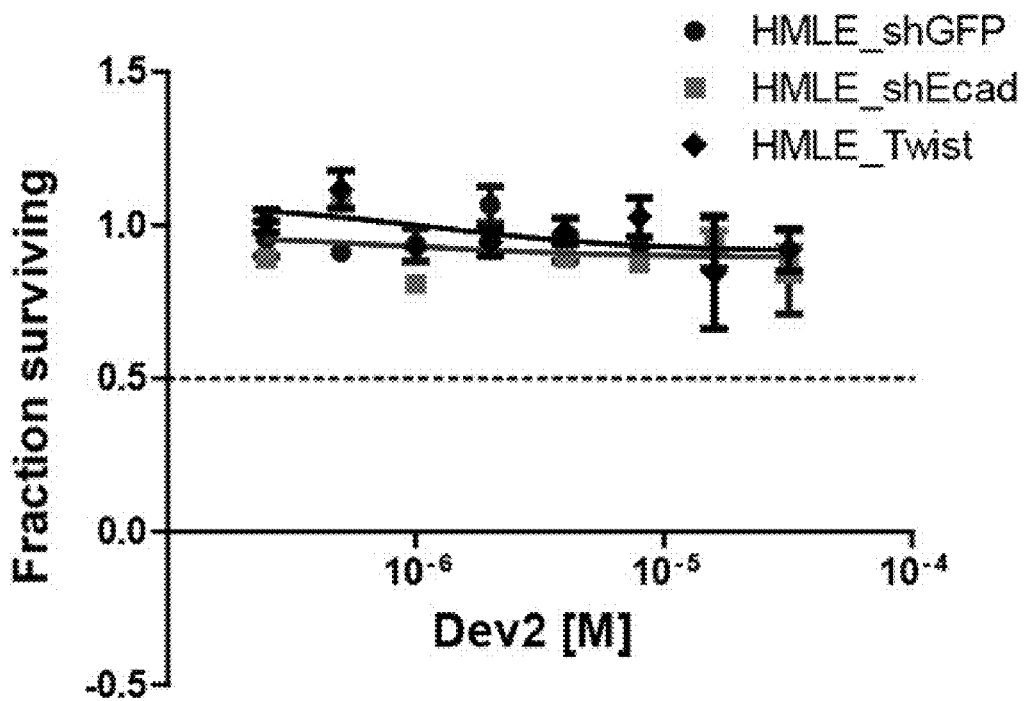
Figure 9A:
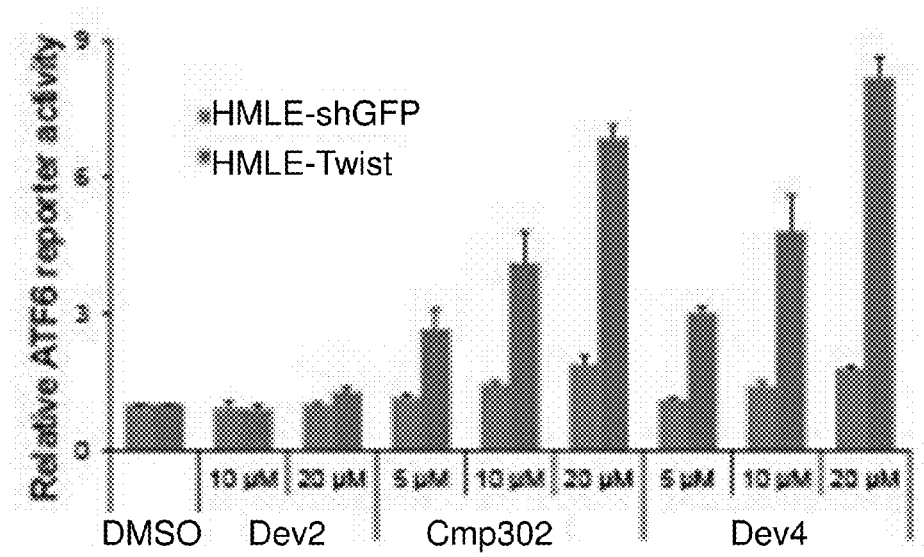
Figure 9B:
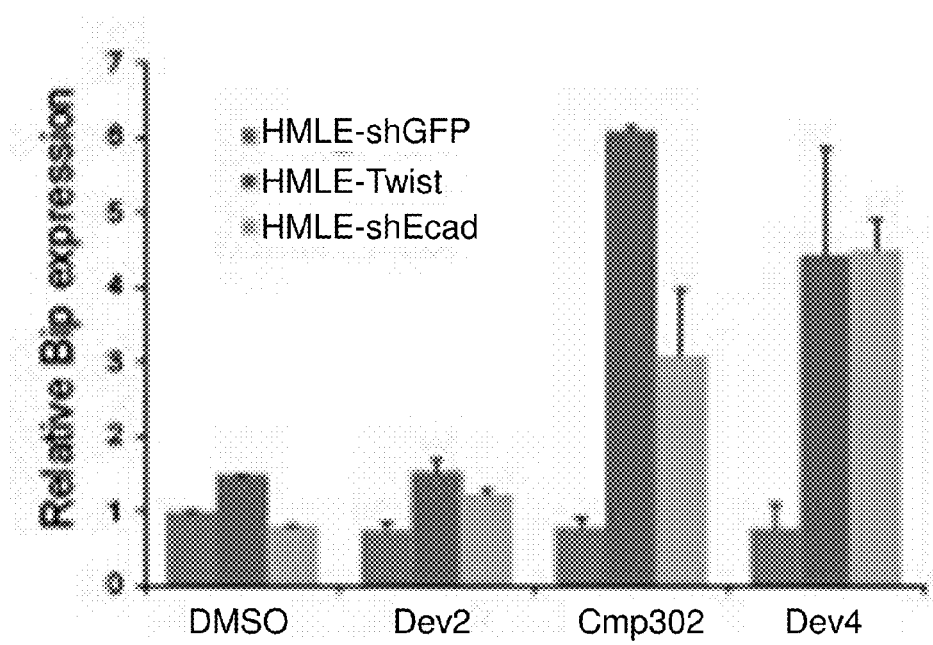
Figure 9C:
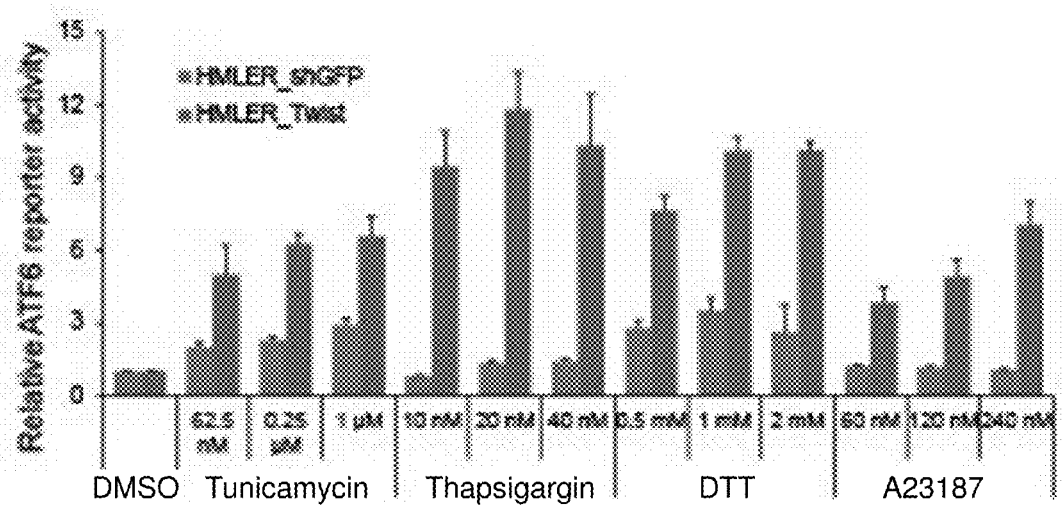
Figure 9D:
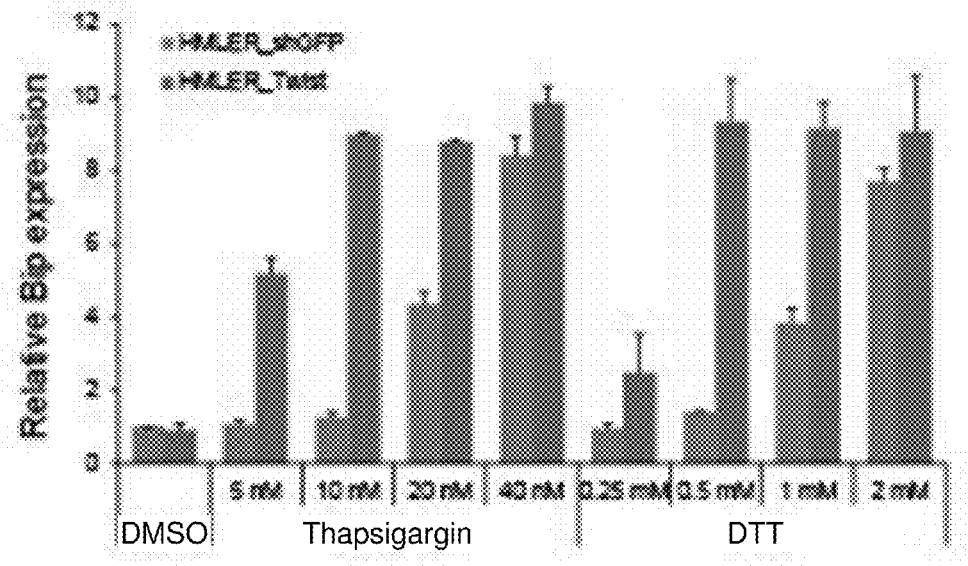
Figure 9E:
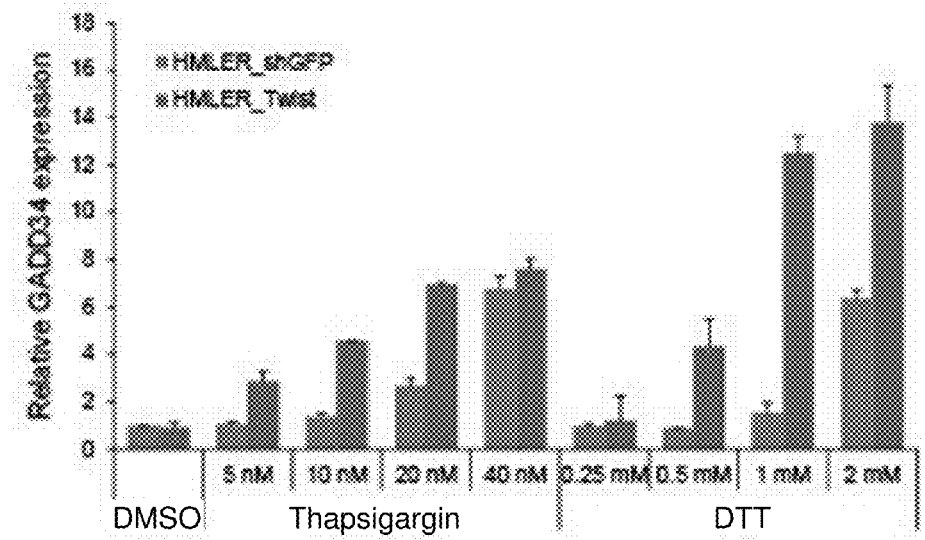
Figure 9F:
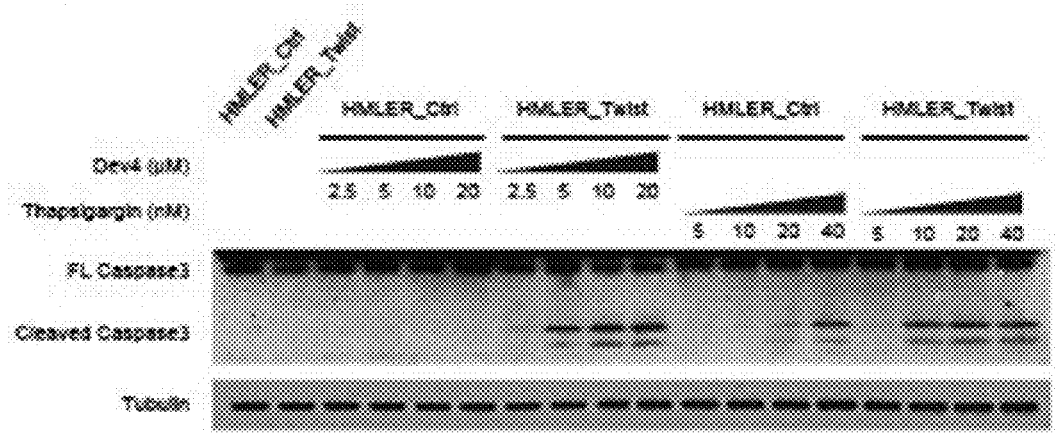

FIGS. 8A-B. Structure and activity of Dev2 compound (A) Molecular structure of Dev2

(B) Dose-response curves indicating viability of Dev2-treated cell lines

FIGS. 9A-F. UPR activation in IDMS cells (A) ATF6 activation of HMLER_shGFP and HMLER_Twist cells in response to IDMS-selective compounds were measured by ATF6 report assay. Reporter activity for each cell line was normalized relative to DMSO treatment.

(B) qPCR analysis for BIP expression in HMLE_shGFP, HMLE_Twist and HMLE_shEcad cells treated with IDMS-selective compounds. BIP expression was normalized relative to GAPDH for each sample.

(C) ATF6 activation of HMLER_shGFP and HMLER_Twist cells in response to Tunicamycin, Thapsigargin, DTT and A23187 were measured by ATF6 reporter assay. Reporter activity for each cell line was normalized relative to DMSO treatment.

(D) qPCR analysis for BIP expression in HMLER_shGFP and HMLER_Twist cells treated with Thapsigargin and DTT. BIP expression was normalized relative to GAPDH for each sample.

(E) qPCR analysis for expression of GADD34 in HMLER_shGFP and HMLER_Twist cells treated with Thapsigargin and DTT. GADD34 expression was normalized relative to GAPDH for each sample.

(F) Western blot analysis for expression of Caspase-3 in HMLER_shGFP and HMLER_Twist cells treated with Dev4 and Thapsigargin.

Figure 10:
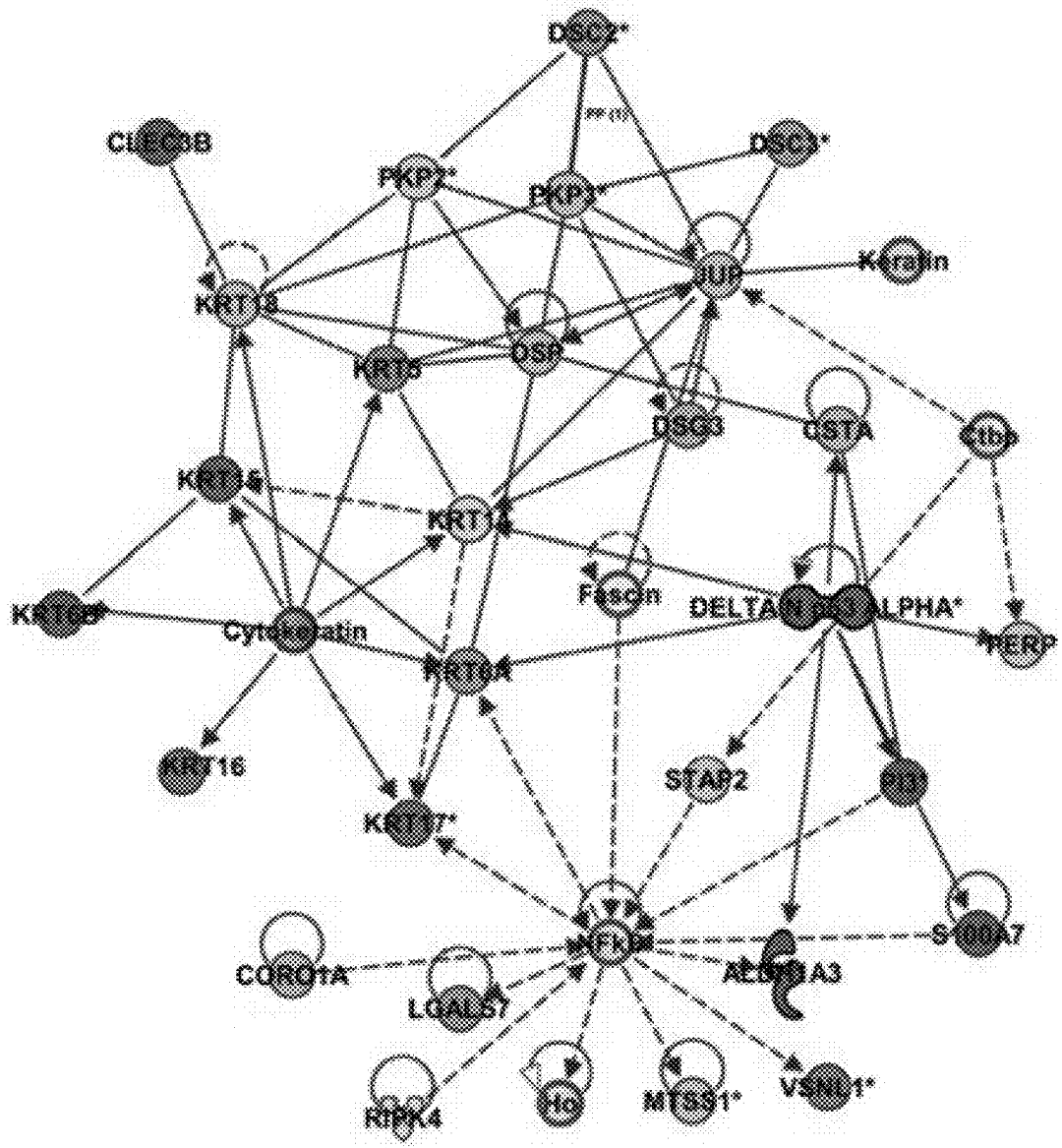

FIG. 10. Differential expression of keratin network genes in IDMS cells

Schematic diagram of keratin gene expression network upregulated in IDMS (HMLE_shEcad, HMLE_Twist, HMLE_Snail, HMLE_TGFb, HMLE_Gsc) compared to non-IDMS control cells (HMLE_shGFP, HMLE_pBp).

Figure 11A:
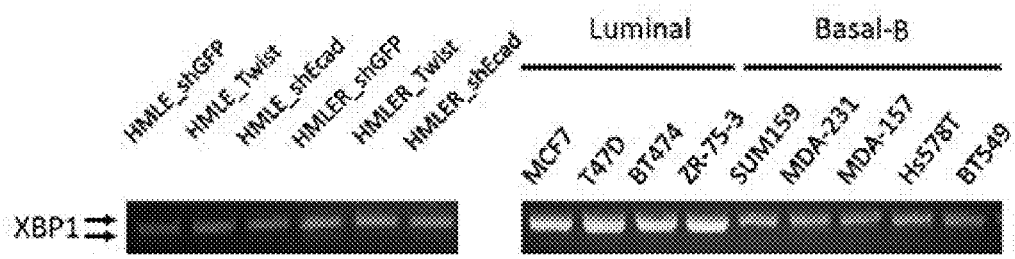
Figure 11B:
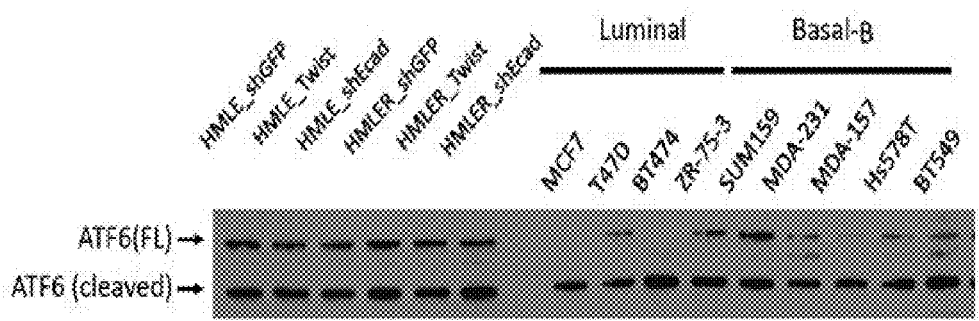

FIGS. 11A-B. Expression of XBP1 and ATF6 in control and IDMS cells (A) RT-PCR analysis of XBP1 expression in human breast cancer cell lines, including IDMS HMLE and HMLER cells (HMLE_Twist, HMLE_shEcad, HMER_Twist, HMLER_shEcad) and their non-IDMS controls (HMLE_shGFP, HMLER_shGFP) as well as Luminal and Basal-B breast cancer cell lines. XBP1 full length (upper arrow) and splice variant (lower arrow) is shown.

(B) Western blot analysis for full length (FL) and cleaved ATF6 expression in the same cell lines as in (A).

Figure 12A:
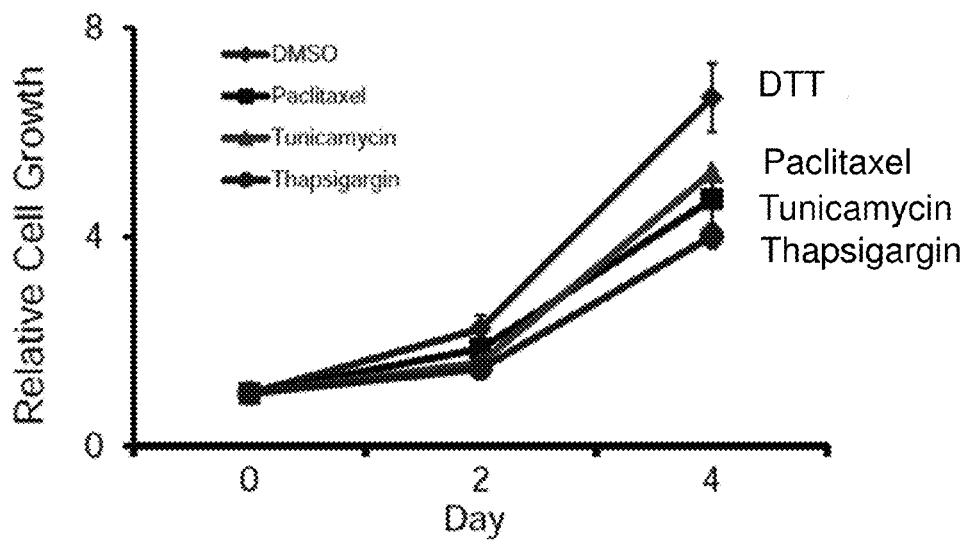
Figure 12B:
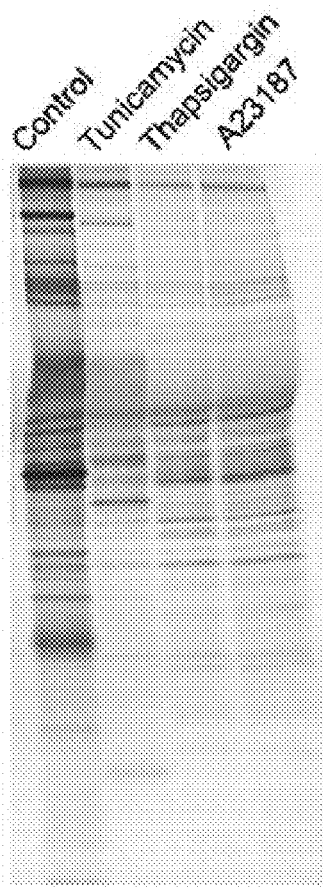

FIGS. 12A-B. Proliferative and secretory properties of compound-treated SUM159 cancer cells (A) SUM159 cells were pretreated with 5 nM Paclitaxel, 1 µg/ml Tunicamycin, 10 nM Thapsigargin, or DMSO vehicle for 3 days. Following a 3 day recovery period in the absence of chemical, proliferation rates were determined.

(B) Autoradiograph showing $^{35}$S-methionine/cysteine-labeled secreted proteins in SUM159 cells that were pretreated with 1 µg/ml Tunicamycin, 10 nM Thapsigargin, 0.1 µM A23187 or DMSO vehicle for 3 days and allowed to recover in the absence of chemical for 3 days prior to the $^{35}$S-methionine/cysteine labeling.

DETAILED DESCRIPTION OF INVENTION

Cancer stem cells (CSCs) have a central role in tumor progression and drug resistance. Some aspects of the invention relate to the identification small molecules with highly selective toxicity towards CSCs. In some embodiments, a strategy to discover functional processes that are differentially active in CSCs vs. non-CSCs is provided herein. In this regard, aspects of the invention relate to the recognition that cancer cells resist therapy, at least in part, by activating a central stress-adaptation program termed the unfolded protein response (UPR). The UPR—which is conserved across metazoa—is induced by nutrient deprivation, hypoxia, oxidative stress, viral infection and accumulation of misfolded proteins within the endoplasmic reticulum (ER). UPR induction prepares the ER in response to misfolded proteins, or in anticipation of an increased secretory load.

UPR signaling is initiated by at least three distinct receptors localized to the ER membrane—endoplasmic reticulum-to-nucleus signaling 1 (ERN1/IRE1α), protein kinase RNA-like endoplasmic reticulum kinase (PERK), and ATF6. While these receptors converge on multiple shared downstream signaling molecules, including BIP, CHOP and GADD34, they also have unique signaling effects: activated IRE1α induces splicing of XBP1 mRNA, resulting in the translation of a frame-shifted short form of the protein that functions as a transcription factor (XBP1(S)); activated PERK phosphorylates eIF2α, inducing an integrated stress response associated with global translational repression and selective translation of repair proteins (e.g., ATF4). In some embodiments, under conditions where ER stress cannot be resolved, continued engagement of the UPR promotes cell death. Moreover, in some embodiments, relatively high levels of CHOP protein expression are associated with an apoptotic switch.

ER-Stress Induction

Aspects of the invention disclosed herein are based on the discovery that ER-stress induction serves as a method to target and eradicate malignant cancer cell subpopulations. Some aspects of the invention are based on the discovery that CSCs and cells that have undergone epithelial-to-mesenchymal transition (EMT) are sensitized to ER stress. Hence, compounds that induce ER stress may be applied to selectively target and eradicate CSC and EMT cells. In some embodiments, methods are provided to selectively eradicate malignant cancer cell subpopulations by treating tumors with compounds that induce endoplasmic reticulum (ER) stress. In some embodiments, methods to eradicate drug-resistant cancer cells by inducing ER stress are provided. In other embodiments, ER-stress inducing compounds are provided that are selectively lethal towards cancer-cell subpopulations that are chemotherapy-resistant. In other embodiments, ER-stress inducing compounds are provided that are selectively lethal towards cancer-cell subpopulations that are paclitaxel- or doxorubicin-resistant. In some embodiments, ER-stress inducing compounds are provided that are selectively lethal towards cancer-cell subpopulations that are resistant to targeted anti-cancer therapies. In some embodiments, methods are provided that selectively eradicate cancer cells that have undergone EMT by inducing endoplasmic reticulum (ER) stress.

Further aspects of the invention disclosed herein are based on the development of methods for identifying ER-stress inducing compounds, e.g., small molecules stressors of endoplasmic reticulum function. In some embodiments, there is significant interest in the therapeutic potential of compounds that induce ER stress. Accordingly, provided herein is a large class of chemical compounds that induce ER stress, as well as a chemical screening strategy that can be utilized to identify such ER-stress inducing compounds. In some embodiments, methods provided herein are useful for compounds (e.g., small molecules) that selectively kill CSCs and/or EMT cells. In some embodiments, methods provided herein are useful for identifying large numbers of ER-stress inducing compounds, which may subsequently be optimized, e.g., by chemical derivatization, for potency and selective toxicity towards CSCs and/or EMT cells.

According to some aspects of the invention methods are provided that may be used to quantify CSC proportions in tumors or other cell populations by assessing unfolded protein response (UPR) signaling pathways. In some embodiments, methods are provided for identifying and quantifying CSCs within tumors by assessing the proportion of cells that have activated PERK-eIF2alpha-ATF4 signaling in cancer cells. In some embodiments, methods are provided for identifying and quantifying CSCs within tumors by assessing the proportion of cancer cells that express downstream unfolded protein response proteins including, for example, BIP (HSPA5), calnexin and GRP94.

According to other aspects of the invention methods are provided for identifying patient subpopulations likely to respond to ER stress-inducing compounds therapies. In some embodiments, highly secretory cells (e.g., cancerous, or non-cancerous cells) are sensitive to ER stress-inducing compounds because of an increased secretory load. In some embodiments, it has been found that reducing the secretory load in highly secretory cells, results in the cells being less sensitive to ER stress-inducing compounds. Hence, in some embodiments, methods are provided that are useful for identifying tumors that are likely to response to ER stress-inducing compounds. In some embodiments, tumors with highly secretory cancer cells are likely to respond to ER stress-inducing compounds. In some embodiments, where ER stress-inducing compounds are used therapeutically, stratifying patients on the degree to which the disease cells are secretory is useful for identifying either patients more likely to respond to the therapy, or patients less likely to respond.

According to some aspects of the invention methods for assaying the secretory capacity of a cell are provided. In some embodiments, the methods are useful to assay the secretory capacity of a cell from a patient. In some embodiments, the secretory capacity is assayed by evaluating the expression of secretory pathway component apparatus. In some embodiments, the secretory capacity is assayed by pulsing cells with labeled amino acids, and then examining the secretion of proteins with the labeled amino acids into the extracellular space. In some embodiments, the secretory capacity is assayed by visualizing the ER in cells; as it is often expanded in highly secretory cells.

According to some aspects of the invention methods are provided for assaying biomarkers that provide an indication of the responsiveness of tumors or cells to ER-inducing compounds. In some embodiments, ER-inducing compounds are useful as therapies in a variety of disease contexts including, though not limited to, cancer. In some embodiments, the clinical development of such therapies benefits from having immediate short-term biomarkers of responsiveness to the applied agent. In some embodiments, these biomarkers indicate that the therapeutic compound has reached a target cell, and that the target cell has responded in an desired way to the compound. Therefore, in some embodiments, the invention provides functional biomarkers that identify cells that have responded to ER-stress inducing compounds.

In some embodiments, the activity of IRE1a or ATF6 may be monitored as biomarkers of response to a treatment with an ER-stress inducing compound in cells that have activated PERK signaling prior to the treatment. The activities of IRE1a or ATF6 can be monitored using any one of a variety of approaches known in the art. These approaches include, for example, phosphorylation status (in the case of IRE1a, PERK), nuclear translocation of signaling proteins (in the case of ATF6 and XBP1, the latter of which is downstream of IRE1a), and phosphorylation or expression of other proteins in the corresponding signaling cascades (e.g., eIF2alpha, Nrf2 are phosphorylated, HSP5A (BIP), GRP94 and calnexin are increased in their expression). In some embodiments, the activity of PERK or ATF6 can be monitored as a biomarker of response in cells that have activated the IRE1a signaling prior to being exposed to an ER-stress inducing compound. In some embodiments, the activity of PERK or IRE1a can be monitored as a biomarker of response in cells that have activated ATF6 signaling prior to being exposed to an ER-stress inducing compound. In some embodiments, the activity of ATF6 can be monitored as a biomarker of response in cells that have activated IRE1a and PERK signaling prior to being exposed to an ER-stress inducing compound. It should be appreciated that in cells that activate (or express) any subset of UPR signaling proteins prior to being exposed to an ER-stress inducing compound, the activity (or expression) of other UPR signaling proteins can be monitored—singly or in combination—as biomarker(s) of responsiveness to the applied ER-stress inducing compound.

In some embodiments, the screening methods are provided that involve two components: first, chemical-genetic interactions are systematically discovered using genome-scale shRNA screens in the presence or absence of selective chemicals; next, computational analyses are applied to identify functional processes that interact with chemical treatment. Using this approach, novel connections between CSCs, ER biology, and stress signaling have been discovered.

ER-Stress Inducing Compounds

As used herein, the term "ER-stress inducing compounds" refers to compounds that directly or indirectly stress endoplasmic reticulum function in cells. In some embodiments, ER-stress inducing compounds are compounds that induce, increase or stimulate endoplasmic reticulum function in cells. In some embodiments, ER-stress inducing compounds are compounds that induce secretion of one or more proteins, e.g., one or more extracellular matrix proteins. In some embodiments, ER-stress inducing compounds are compounds that induce in cells one or more (e.g., at least three) downstream signaling pathways that collectively comprise the unfolded protein response (UPR) signaling pathway. In some embodiments, ER-stress inducing compounds activate three UPR pathways controlled by the ER transmembrane proteins IRE1a, PERK, and ATF6. However, in some embodiments, ER-stress inducing compounds selectively activate one or more UPR pathways controlled by the ER transmembrane proteins, e.g., one or more UPR pathways controlled by IRE1a, PERK, and ATF6. In some embodiments, it has been discovered that cancer cells subpopulations can selectively activate one UPR pathway. In some embodiments, cancer stem cells (CSCs), or cancer cells that have undergone EMT, constitutively activate the PERK branch of UPR signaling, but do not have constitutively active IRE1a or ATF6 signaling. In some embodiments, constitutive activation of one UPR pathway, PERK, sensitizes CSCs and EMT cancer cells to agents that induce ER stress. In some embodiments, when CSCs and EMT cells encounter ER stress, they rapidly activate other UPR pathways, e.g., IRE1a and ATF6 mediated pathways, and do so at lower doses of ER stressors than cancer cells that do not activate PERK signaling. In some embodiments, selective activation of one UPR pathway sensitizes cells to ER-stress inducing compounds and, in response to such compounds, cells activate other UPR pathways that were not active prior to treatment.

In certain embodiments, the ER-stress inducing compound is a compound of Formula (I):

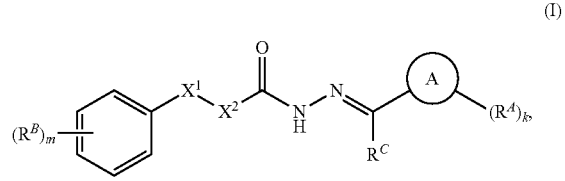

and pharmaceutically acceptable salts, solvates, hydrates, polymorphs, co-crystals, tautomers, stereoisomers, isotopically labeled derivatives, and prodrugs thereof;
wherein:
Ring A is a substituted or unsubstituted aryl ring, or substituted or unsubstituted heteroaryl ring;
each instance of $R^A$ is independently hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{A1}$, —$N(R^{A1})_2$, —$SR^{A1}$, —CN, —SCN, —$C(=NR^{A1})R^{A1}$, —$C(=NR^{A1})OR^{A1}$, —$C(=NR^{A1})N(R^{A1})_2$, —$C(=O)R^{A1}$, —$C(=O)OR^{A1}$, —$C(=O)N(R^{A1})_2$, —$NO_2$, —$NR^{A1}C(=O)R^{A1}$, —$NR^{A1}C(=O)OR^{A1}$, —$NR^{A1}C(=O)N(R^{A1})_2$, —$OC(=O)R^{A1}$, —$OC(=O)OR^{A1}$, —$OC(=O)N(R^{A1})_2$, or a nitrogen protecting group when attached to a nitrogen atom, or optionally two $R^A$ groups are joined to form a substituted or unsubstituted carbocyclic, substituted or unsubstituted heterocyclic, substituted or unsubstituted aryl, or substituted or unsubstituted heteroaryl ring;
each instance of $R^{A1}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or optionally two $R^{A1}$ groups are joined to form a substituted or unsubstituted heterocyclic ring;
k is 0, 1, 2, 3, 4, or 5;
each instance of $R^B$ is independently hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{B1}$, —$N(R^{B1})_2$, —$SR^{B1}$, —CN, —SCN, —$C(=NR^{B1})R^{B1}$, —$C(=NR^{B1})OR^{B1}$, —$C(=NR^{B1})N(R^{B1})_2$, —$C(=O)R^{B1}$, —$C(=O)OR^{B1}$, —$C(=O)N(R^{B1})_2$, —$NO_2$, —$NR^{B1}C(=O)R^{B1}$, —$NR^{B1}C(=O)OR^{B1}$, —$NR^{B1}C(=O)N(R^{B1})_2$, —$OC(=O)R^{B1}$, —$OC(=O)OR^{B1}$, or —$OC(=O)N(R^{B1})_2$, or optionally two $R^B$ groups are joined to form a substituted or unsubstituted carbocyclic, substituted or unsubstituted heterocyclic, substituted or unsubstituted aryl, or substituted or unsubstituted heteroaryl ring;
each instance of $R^{B1}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or optionally two $R^{B1}$ groups are joined to form a substituted or unsubstituted heterocyclic ring;
m is 0, 1, 2, 3, 4, or 5;

$R^C$ is hydrogen or $C_{1-6}$ alkyl;
$X^1$ and $X^2$ are each independently —O—, —S—, —$NR^D$—, —$C(R^E)_2$—, or —$C(=C(R^E)_2)$—;
$R^D$ is is hydrogen, $C_{1-6}$ alkyl, or a nitrogen protecting group, or optionally $R^D$ and one $R^B$ group are joined to form a substituted or unsubstituted heterocyclic ring; and
each instance of $R^E$ is independently hydrogen, halogen, or $C_{1-6}$ alkyl, or optionally two $R^E$ groups are joined to form a substituted or unsubstituted carbocyclic ring, or optionally one $R^E$ group and one $R^B$ group are joined to form a substituted or unsubstituted carbocyclic ring, substituted or unsubstituted heterocyclic ring, substituted or unsubstituted aryl ring, or substituted or unsubstituted heteroaryl ring.

In certain embodiments, the present invention provides compounds of Formula (I), and pharmaceutically acceptable salts thereof.

Compounds of Formula (I) can be synthesized used methods known in the art, including methods as described in Germain A R, et al., Bioorganic & Medicinal Chemistry Letters 22 (2012) 3571-3574, the contents of which are incorporated herein by reference in its entirety for all purposes.

Compounds of Formula (I) include a substituted or unsubstituted aryl ring, or substituted or unsubstituted heteroaryl ring as Ring A. In certain embodiments, Ring A is a substituted aryl ring. In certain embodiments, Ring A is an unsubstituted aryl ring. In certain embodiments, Ring A is a monocyclic aryl ring. In certain embodiments, Ring A is substituted phenyl. In certain embodiments, Ring A is of the formula:

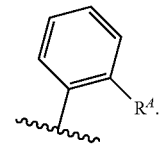

In certain embodiments, Ring A is of the formula:

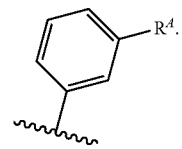

In certain embodiments, Ring A is of the formula:

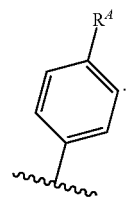

In certain embodiments, Ring A is of the formula:

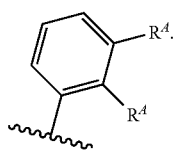

In certain embodiments, Ring A is of the formula:

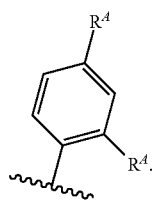

In certain embodiments, Ring A is of the formula:

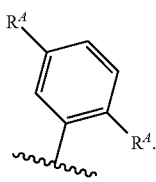

In certain embodiments, Ring A is of the formula:

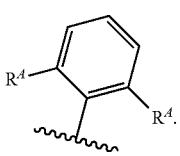

In certain embodiments, Ring A is of the formula:

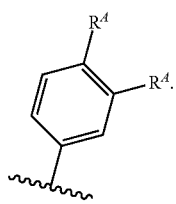

In certain embodiments, Ring A is of the formula:

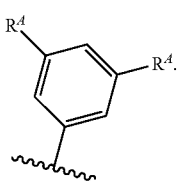

In certain embodiments, Ring A is unsubstituted phenyl. In certain embodiments, Ring A is a bicyclic aryl ring. In certain embodiments, Ring A is substituted naphthyl. In certain embodiments, Ring A is unsubstituted naphthyl. In certain embodiments, Ring A is a tricyclic aryl ring. In certain embodiments, Ring A is substituted anthracenyl. In certain embodiments, Ring A is unsubstituted anthracenyl. In certain embodiments, Ring A is an optionally substituted aryl ring fused with one or more optionally substituted carbocyclic, optionally substituted heterocyclic, optionally substituted aryl, or optionally substituted heteroaryl groups wherein the point of attachment is on the aryl ring.

Ring A of Formula (I) may also be an optionally substituted heteroaryl ring. In certain embodiments, Ring A is a substituted heteroaryl ring. In certain embodiments, Ring A is an unsubstituted heteroaryl ring. In certain embodiments, Ring A is a monocyclic heteroaryl ring. In certain embodiments, Ring A is a 6-membered monocyclic heteroaryl ring. In certain embodiments, Ring A is a 6-membered monocyclic heteroaryl ring, wherein only one of the six atoms in the ring of the heteroaryl is nitrogen. In certain embodiments, Ring A is of the formula:

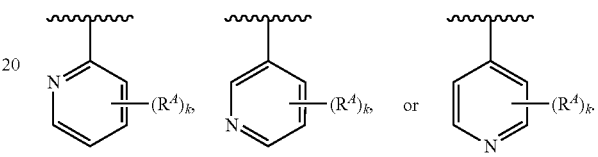

In certain embodiments, Ring A is a 6-membered monocyclic heteroaryl ring, wherein only two of the six atoms in the ring of the heteroaryl are nitrogen. In certain embodiments, Ring A is of the formula:

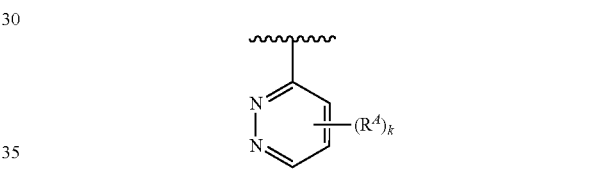

or

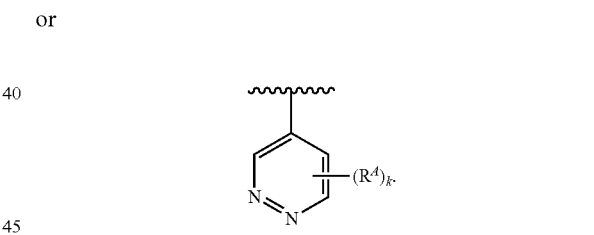

In certain embodiments, Ring A is of the formula:

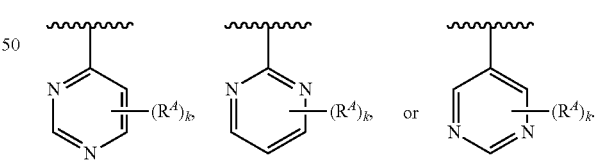

In certain embodiments, Ring A is of the formula:

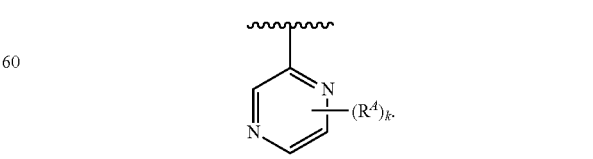

In certain embodiments, Ring A is a 6-membered monocyclic heteroaryl ring, wherein only three of the six atoms in the ring of the heteroaryl are nitrogen. In certain embodiments, Ring A is of the formula:

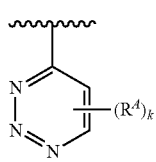

or

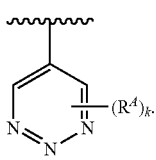

In certain embodiments, Ring A is of the formula:

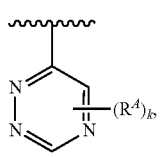 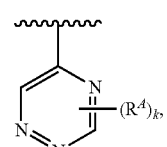

or

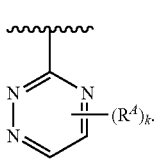

In certain embodiments, Ring A is of the formula:

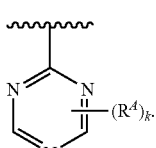

In certain embodiments, Ring A is a 5-membered monocyclic heteroaryl ring. In certain embodiments, Ring A is a 5-membered monocyclic heteroaryl ring, wherein only one of the five atoms in the ring of the heteroaryl is nitrogen, oxygen, or sulfur. In certain embodiments, Ring A is of the formula:

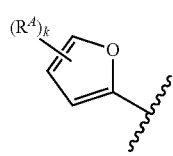

or

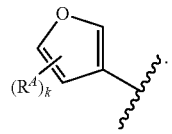

In certain embodiments, Ring A is of the formula:

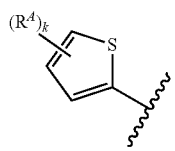

or

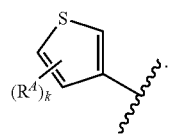

In certain embodiments, Ring A is of the formula:

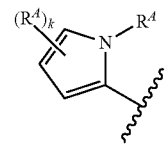

or

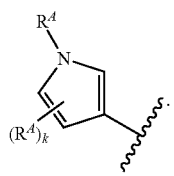

In certain embodiments, Ring A is of the formula:

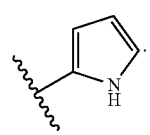 [SMILES: *c1ccc[nH]1]

In certain embodiments, Ring A is of the formula:

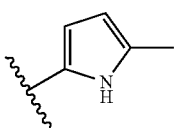

In certain embodiments, Ring A is a 5-membered monocyclic heteroaryl ring, wherein only two of the five atoms in the ring of the heteroaryl are independently nitrogen, oxygen, or sulfur. In certain embodiments, Ring A is of the formula:

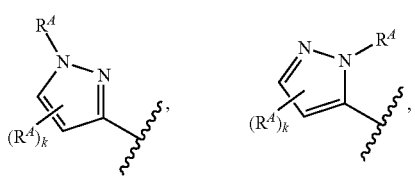

or

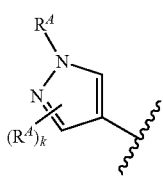

In certain embodiments, Ring A is of the formula:

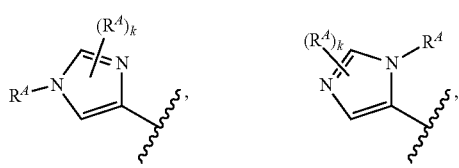

or

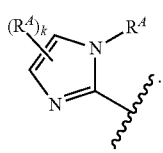

In certain embodiments, Ring A is of the formula:

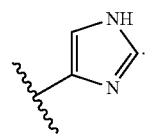

In certain embodiments, Ring A is of the formula:

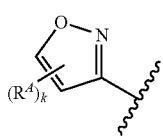

or

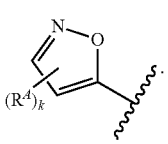

In certain embodiments, Ring A is of the formula:

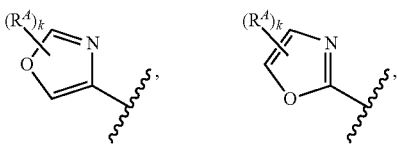

or

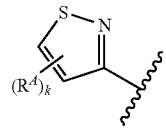

In certain embodiments, Ring A is of the formula:

(structures shown)

or (structure shown)

In certain embodiments, Ring A is of the formula:

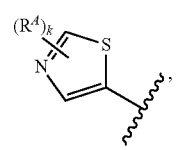

In certain embodiments, Ring A is a 5-membered monocyclic heteroaryl ring, wherein only three of the five atoms in the ring of the heteroaryl are independently nitrogen, oxygen, or sulfur. In certain embodiments, Ring A is of the formula:

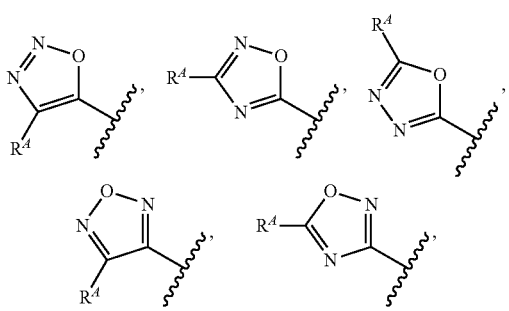

or

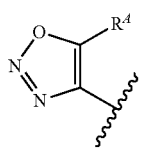

In certain embodiments, Ring A is of the formula:

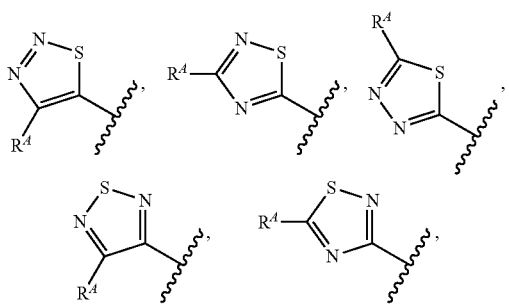

or

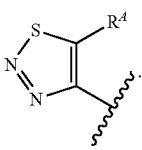

In certain embodiments, Ring A is of the formula

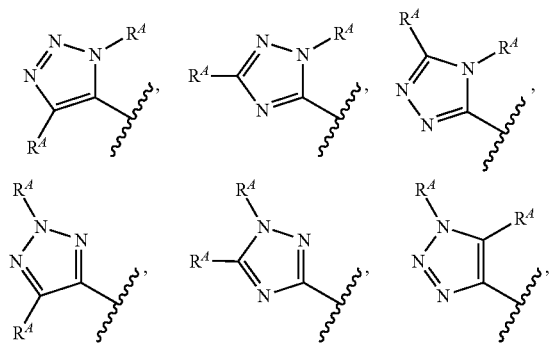

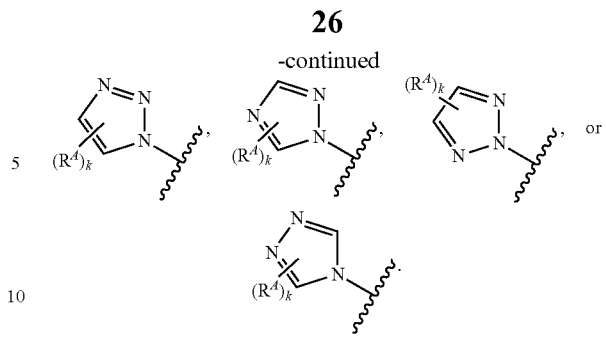

In certain embodiments, Ring A is a 5-membered monocyclic heteroaryl ring, wherein only four of the five atoms in the ring of the heteroaryl are nitrogen, oxygen, or sulfur. In certain embodiments, Ring A is of the formula:

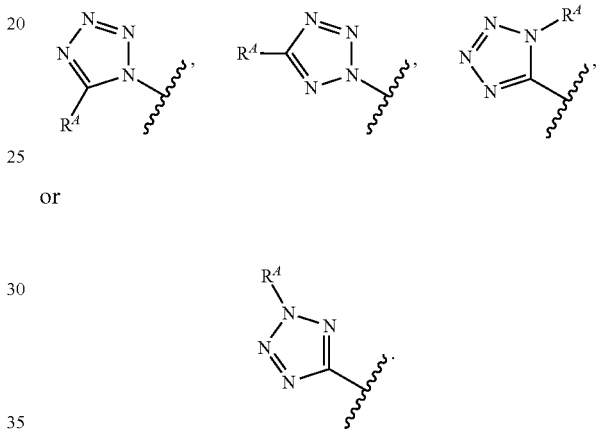

In certain embodiments, Ring A is bicyclic heteroaryl, wherein the point of attachment may be on any atom of the bicyclic heteroaryl ring system, as valency permits. In certain embodiments, Ring A is a monocyclic heteroaryl ring fused with phenyl. In certain embodiments, Ring A is a 5-membered monocyclic heteroaryl ring fused with phenyl. In certain embodiments, Ring A is a 6-membered monocyclic heteroaryl ring fused with phenyl. In certain embodiments, Ring A is a monocyclic heteroaryl ring fused with another monocyclic heteroaryl. In certain embodiments, Ring A is a 5-membered monocyclic heteroaryl ring fused with another 5-membered monocyclic heteroaryl. In certain embodiments, Ring A is a 5-membered monocyclic heteroaryl ring fused with a 6-membered monocyclic heteroaryl. In certain embodiments, Ring A is substituted or unsubstituted 2-indolyl. In certain embodiments, Ring A is a 6-membered monocyclic heteroaryl ring fused with another 6-membered monocyclic heteroaryl.

Ring A of compounds of Formula (I) may include one or more substituents $R^A$. In certain embodiments, at least one $R^A$ is H. In certain embodiments, at least one $R^A$ is halogen. In certain embodiments, at least one $R^A$ is F. In certain embodiments, at least one $R^A$ is Cl. In certain embodiments, at least one $R^A$ is Br. In certain embodiments, at least one $R^A$ is I (iodine). In certain embodiments, at least one $R^A$ is substituted acyl. In certain embodiments, at least one $R^A$ is unsubstituted acyl. In certain embodiments, at least one $R^A$ is substituted alkyl. In certain embodiments, at least one $R^A$ is unsubstituted alkyl. In certain embodiments, at least one $R^A$ is $C_{1-6}$ alkyl. In certain embodiments, at least one $R^A$ is methyl.

In certain embodiments, at least one $R^A$ is substituted methyl. In certain embodiments, at least one $R^A$ is —CH$_2$F. In certain embodiments, at least one $R^A$ is —CHF$_2$. In certain embodiments, at least one $R^A$ is —CF$_3$. In certain embodiments, at least one $R^A$ is Bn. In certain embodiments, at least one $R^A$ is ethyl. In certain embodiments, at least one $R^A$ is substituted ethyl. In certain embodiments, at least one $R^A$ is —(CH$_2$)$_2$Ph. In certain embodiments, at least one $R^A$ is propyl. In certain embodiments, at least one $R^A$ is butyl. In certain embodiments, at least one $R^A$ is pentyl. In certain embodiments, at least one $R^A$ is hexyl. In certain embodiments, at least one $R^A$ is substituted alkenyl. In certain embodiments, at least one $R^A$ is unsubstituted alkenyl. In certain embodiments, at least one $R^A$ is vinyl. In certain embodiments, at least one $R^A$ is substituted alkynyl. In certain embodiments, at least one $R^A$ is unsubstituted alkynyl. In certain embodiments, at least one $R^A$ is ethynyl. In certain embodiments, at least one $R^A$ is substituted carbocyclyl. In certain embodiments, at least one $R^A$ is unsubstituted carbocyclyl. In certain embodiments, at least one $R^A$ is cylcopropyl. In certain embodiments, at least one $R^A$ is cylcobutyl. In certain embodiments, at least one $R^A$ is cyclopentyl. In certain embodiments, at least one $R^A$ is cyclohexyl. In certain embodiments, at least one $R^A$ is cycloheptyl. In certain embodiments, at least one $R^A$ is substituted heterocyclyl. In certain embodiments, at least one $R^A$ is unsubstituted heterocyclyl. In certain embodiments, at least one $R^A$ is substituted aryl. In certain embodiments, at least one $R^A$ is unsubstituted aryl. In certain embodiments, at least one $R^A$ is substituted phenyl. In certain embodiments, at least one $R^A$ is unsubstituted phenyl. In certain embodiments, at least one $R^A$ is substituted naphthyl. In certain embodiments, at least one $R^A$ is unsubstituted naphthyl. In certain embodiments, at least one $R^A$ is substituted heteroaryl. In certain embodiments, at least one $R^A$ is unsubstituted heteroaryl. In certain embodiments, at least one $R^A$ is monocyclic heteroaryl. In certain embodiments, at least one $R^A$ is 5-membered monocyclic heteroaryl. In certain embodiments, at least one $R^A$ is 5-membered monocyclic heteroaryl, wherein only one of the five atoms in the ring of the heteroaryl is nitrogen, oxygen, or sulfur. In certain embodiments, at least one $R^A$ is 5-membered monocyclic heteroaryl, wherein only two of the five atoms in the ring of the heteroaryl are independently nitrogen, oxygen, or sulfur. In certain embodiments, at least one $R^A$ is 5-membered monocyclic heteroaryl, wherein only three of the five atoms in the ring of the heteroaryl are independently nitrogen, oxygen, or sulfur. In certain embodiments, at least one $R^A$ is tetrazolyl. In certain embodiments, at least one $R^A$ is 6-membered monocyclic heteroaryl. In certain embodiments, at least one $R^A$ is 6-membered monocyclic heteroaryl, wherein only one of the six atoms in the ring of the heteroaryl is nitrogen. In certain embodiments, at least one $R^A$ is 6-membered monocyclic heteroaryl, wherein only two of the six atoms in the ring of the heteroaryl are nitrogen. In certain embodiments, at least one $R^A$ is triazinyl. In certain embodiments, at least one $R^A$ is tetrazinyl. In certain embodiments, at least one $R^A$ is bicyclic heteroaryl, wherein the point of attachment may be on any atom of the bicyclic heteroaryl ring system, as valency permits. In certain embodiments, at least one $R^A$ is a monocyclic heteroaryl ring fused with phenyl. In certain embodiments, at least one $R^A$ is a 5-membered monocyclic heteroaryl ring fused with phenyl. In certain embodiments, at least one $R^A$ is a 6-membered monocyclic heteroaryl ring fused with phenyl. In certain embodiments, at least one $R^A$ is a monocyclic heteroaryl ring fused with another monocyclic heteroaryl. In certain embodiments, at least one $R^A$ is a 5-membered monocyclic heteroaryl ring fused with another 5-membered monocyclic heteroaryl. In certain embodiments, at least one $R^A$ is a 5-membered monocyclic heteroaryl ring fused with a 6-membered monocyclic heteroaryl. In certain embodiments, at least one $R^A$ is a 6-membered monocyclic heteroaryl fused with another 6-membered monocyclic heteroaryl. In certain embodiments, at least one $R^A$ is —OR$^{A1}$. In certain embodiments, at least one $R^A$ is —OMe. In certain embodiments, at least one $R^A$ is —OEt. In certain embodiments, at least one $R^A$ is —OPr. In certain embodiments, at least one $R^A$ is —OBu. In certain embodiments, at least one $R^A$ is —O(pentyl). In certain embodiments, at least one $R^A$ is —O(hexyl). In certain embodiments, at least one $R^A$ is —OPh. In certain embodiments, at least one $R^A$ is —OBn. In certain embodiments, at least one $R^A$ is —O(CH$_2$)$_2$Ph. In certain embodiments, at least one $R^A$ is —OH. In certain embodiments, at least one $R^A$ is —SR$^{A1}$. In certain embodiments, at least one $R^A$ is —SH. In certain embodiments, at least one $R^A$ is —N(R$^{A1}$)$_2$. In certain embodiments, at least one $R^A$ is —NH$_2$. In certain embodiments, at least one $R^A$ is —CN. In certain embodiments, at least one $R^A$ is —SCN. In certain embodiments, at least one $R^A$ is —C(=NR$^{A1}$)R$^{A1}$, —C(=NR$^{A1}$)OR$^{A1}$, or —C(=NR$^{A1}$)N(R$^{A1}$)$_2$. In certain embodiments, at least one $R^A$ is —C(=O)R$^{A1}$, —C(=O)OR$^{A1}$, or —C(=O)N(R$^{A1}$)$_2$. In certain embodiments, at least one $R^A$ is —NO$_2$. In certain embodiments, at least one $R^A$ is —NR$^{A1}$C(=O)R$^{A1}$, —NR$^{A1}$C(=O)OR$^{A1}$, or —NR$^{A1}$C(=O)N(R$^{A1}$)$_2$. In certain embodiments, at least one $R^A$ is —OC(=O)R$^{A1}$, —OC(=O)OR$^{A1}$, or —OC(=O)N(R$^{A1}$)$_2$. In certain embodiments, at least one $R^A$ is a nitrogen protecting group when attached to a nitrogen atom. In certain embodiments, at least one $R^A$ is Bn, BOC, Cbz, Fmoc, trifluoroacetyl, triphenylmethyl, or Ts when attached to a nitrogen atom.

In compounds of Formula (I), two $R^A$ groups may be joined to form a substituted or unsubstituted carbocyclic ring. In certain embodiments, two $R^A$ groups are joined to form a substituted or unsubstituted cyclopropyl ring. In certain embodiments, two $R^A$ groups are joined to form a substituted or unsubstituted cyclobutyl ring. In certain embodiments, two $R^A$ groups are joined to form a substituted or unsubstituted cyclopentyl ring. In certain embodiments, two $R^A$ groups are joined to form a substituted or unsubstituted cyclohexyl ring. In certain embodiments, two $R^A$ groups are joined to form a substituted or unsubstituted cycloheptyl ring. In certain embodiments, two $R^A$ groups are joined to form a substituted or unsubstituted cyclooctyl ring. In certain embodiments, two $R^A$ groups are joined to form a substituted or unsubstituted cyclononyl ring. In certain embodiments, two $R^A$ groups are joined to form a substituted or unsubstituted cyclodecyl ring.

In certain embodiments, two $R^A$ groups are joined to form a substituted or unsubstituted heterocyclic ring. In certain embodiments, two $R^A$ groups are joined to form a substituted or unsubstituted 4-membered heterocyclic ring. In certain embodiments, two $R^A$ groups are joined to form a substituted or unsubstituted 5-membered heterocyclic ring. In certain embodiments, two $R^A$ groups are joined to form a substituted or unsubstituted 6-membered heterocyclic ring. In certain embodiments, two $R^A$ groups are joined to form a substituted or unsubstituted 7-membered heterocyclic ring. In certain embodiments, two $R^A$ groups are joined to form a substituted or unsubstituted 8-membered heterocyclic ring. In certain embodiments, two $R^A$ groups are joined to form a substituted or unsubstituted 9-membered heterocyclic ring. In certain embodiments, two $R^A$ groups are joined to form a substituted or unsubstituted 10-membered heterocyclic ring.

In certain embodiments, two $R^A$ groups are joined to form a substituted or unsubstituted aryl ring. In certain embodiments, two $R^A$ groups are joined to form a substituted or unsubstituted monocyclic aryl ring. In certain embodiments, two $R^A$ groups are joined to form a substituted or unsubstituted phenyl ring. In certain embodiments, two $R^A$ groups are joined to form a substituted or unsubstituted bicyclic aryl ring. In certain embodiments, two $R^A$ groups are joined to form a substituted or unsubstituted naphthyl ring.

In certain embodiments, two $R^A$ groups are joined to form a substituted or unsubstituted heteroaryl ring. In certain embodiments, two $R^A$ groups are joined to form a substituted or unsubstituted monocyclic heteroaryl ring. In certain embodiments, two $R^A$ groups are joined to form a substituted or unsubstituted 5-membered monocyclic heteroaryl ring. In certain embodiments, two $R^A$ groups are joined to form a substituted or unsubstituted 6-membered monocyclic heteroaryl ring. In certain embodiments, two $R^A$ groups are joined to form a substituted or unsubstituted, bicyclic heteroaryl ring. In certain embodiments, two $R^A$ groups are joined to form a substituted or unsubstituted, 5,6-membered bicyclic heteroaryl ring. In certain embodiments, two $R^A$ groups are joined to form a substituted or unsubstituted, 6,5-membered bicyclic heteroaryl ring. In certain embodiments, two $R^A$ groups are joined to form a substituted or unsubstituted, 6,6-membered bicyclic heteroaryl ring.

In certain embodiments, at least one $R^{A1}$ is H. In certain embodiments, at least one $R^{A1}$ is substituted acyl. In certain embodiments, at least one $R^{A1}$ is unsubstituted acyl. In certain embodiments, at least one $R^{A1}$ is acetyl. In certain embodiments, at least one $R^{A1}$ is substituted alkyl. In certain embodiments, at least one $R^{A1}$ is unsubstituted alkyl. In certain embodiments, at least one $R^{A1}$ is $C_{1-6}$ alkyl. In certain embodiments, at least one $R^{A1}$ is methyl. In certain embodiments, at least one $R^{A1}$ is ethyl. In certain embodiments, at least one $R^{A1}$ is propyl. In certain embodiments, at least one $R^{A1}$ is butyl. In certain embodiments, at least one $R^{A1}$ is pentyl. In certain embodiments, at least one $R^{A1}$ is hexyl. In certain embodiments, at least one $R^{A1}$ is substituted alkenyl. In certain embodiments, at least one $R^{A1}$ is unsubstituted alkenyl. In certain embodiments, at least one $R^{A1}$ is vinyl. In certain embodiments, at least one $R^{A1}$ is substituted alkynyl. In certain embodiments, at least one $R^{A1}$ is unsubstituted alkynyl. In certain embodiments, at least one $R^{A1}$ is ethynyl. In certain embodiments, at least one $R^{A1}$ is substituted carbocyclyl. In certain embodiments, at least one $R^{A1}$ is unsubstituted carbocyclyl. In certain embodiments, at least one $R^{A1}$ is cylcopropyl. In certain embodiments, at least one $R^{A1}$ is cylcobutyl. In certain embodiments, at least one $R^{A1}$ is cyclopentyl. In certain embodiments, at least one $R^{A1}$ is cyclohexyl. In certain embodiments, at least one $R^{A1}$ is cycloheptyl. In certain embodiments, at least one $R^{A1}$ is substituted heterocyclyl. In certain embodiments, at least one $R^{A1}$ is unsubstituted heterocyclyl. In certain embodiments, at least one $R^{A1}$ is substituted aryl. In certain embodiments, at least one $R^{A1}$ is unsubstituted aryl. In certain embodiments, at least one $R^{A1}$ is substituted phenyl. In certain embodiments, at least one $R^{A1}$ is unsubstituted phenyl. In certain embodiments, at least one $R^{A1}$ is substituted heteroaryl. In certain embodiments, at least one $R^{A1}$ is unsubstituted heteroaryl. In certain embodiments, at least one $R^{A1}$ is substituted pyridyl. In certain embodiments, at least one $R^{A1}$ is unsubstituted pyridyl. In certain embodiments, at least one $R^{A1}$ is a nitrogen protecting group when attached to a nitrogen atom. In certain embodiments, at least one $R^{A1}$ is Bn, Boc, Cbz, Fmoc, trifluoroacetyl, triphenylmethyl, or Ts when attached to a nitrogen atom. In certain embodiments, $R^{A1}$ is an oxygen protecting group when attached to an oxygen atom. In certain embodiments, $R^{A1}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{A1}$ is a sulfur protecting group when attached to a sulfur atom. In certain embodiments, $R^{A1}$ is acetamidomethyl, t-Bu, 3-nitro-2-pyridine sulfenyl, 2-pyridine-sulfenyl, or triphenylmethyl when attached to a sulfur atom. In certain embodiments, two $R^{A1}$ groups are joined to form a substituted heterocyclic ring. In certain embodiments, two $R^{A1}$ groups are joined to form an unsubstituted heterocyclic ring. In certain embodiments, two $R^{A1}$ groups are joined to form a substituted heteroaryl ring. In certain embodiments, two $R^{A1}$ groups are joined to form an unsubstituted heteroaryl ring.

In certain embodiments, k is 0. In certain embodiments, k is 1. In certain embodiments, k is 2. In certain embodiments, k is 3. In certain embodiments, k is 4. In certain embodiments, k is 5.

Compounds of Formula (I) may include zero, one, two, or more substituents $R^B$. In certain embodiments, at least one $R^B$ is H. In certain embodiments, at least one $R^B$ is halogen. In certain embodiments, at least one $R^B$ is F. In certain embodiments, at least one $R^B$ is Cl. In certain embodiments, at least one $R^B$ is Br. In certain embodiments, at least one $R^B$ is I (iodine). In certain embodiments, at least one $R^B$ is substituted acyl. In certain embodiments, at least one $R^B$ is unsubstituted acyl. In certain embodiments, at least one $R^B$ is substituted alkyl. In certain embodiments, at least one $R^B$ is unsubstituted alkyl. In certain embodiments, at least one $R^B$ is $C_{1-6}$ alkyl. In certain embodiments, at least one $R^B$ is methyl. In certain embodiments, at least one $R^B$ is substituted methyl. In certain embodiments, at least one $R^B$ is —$CH_2F$. In certain embodiments, at least one $R^B$ is —$CHF_2$. In certain embodiments, at least one $R^B$ is —$CF_3$. In certain embodiments, at least one $R^B$ is benzyl (Bn). In certain embodiments, at least one $R^B$ is ethyl. In certain embodiments, at least one $R^B$ is substituted ethyl. In certain embodiments, at least one $R^B$ is —$(CH_2)_2Ph$. In certain embodiments, at least one $R^B$ is propyl. In certain embodiments, at least one $R^B$ is butyl. In certain embodiments, at least one $R^B$ is pentyl. In certain embodiments, at least one $R^B$ is hexyl. In certain embodiments, at least one $R^B$ is substituted alkenyl. In certain embodiments, at least one $R^B$ is unsubstituted alkenyl. In certain embodiments, at least one $R^B$ is vinyl. In certain embodiments, at least one $R^B$ is substituted alkynyl. In certain embodiments, at least one $R^B$ is unsubstituted alkynyl. In certain embodiments, at least one $R^B$ is ethynyl. In certain embodiments, at least one $R^B$ is substituted carbocyclyl. In certain embodiments, at least one $R^B$ is unsubstituted carbocyclyl. In certain embodiments, at least one $R^B$ is cylcopropyl. In certain embodiments, at least one $R^B$ is cylcobutyl. In certain embodiments, at least one $R^B$ is cyclopentyl. In certain embodiments, at least one $R^B$ is cyclohexyl. In certain embodiments, at least one $R^B$ is cycloheptyl. In certain embodiments, at least one $R^B$ is substituted heterocyclyl. In certain embodiments, at least one $R^B$ is unsubstituted heterocyclyl. In certain embodiments, at least one $R^B$ is substituted aryl. In certain embodiments, at least one $R^B$ is unsubstituted aryl. In certain embodiments, at least one $R^B$ is substituted phenyl. In certain embodiments, at least one $R^B$ is unsubstituted phenyl. In certain embodiments, at least one $R^B$ is substituted naphthyl. In certain embodiments, at least one $R^B$ is unsubstituted naphthyl. In certain embodiments, at least one $R^B$ is substituted heteroaryl. In certain embodiments, at least one $R^B$ is unsubstituted heteroaryl. In certain embodiments, at least one $R^B$ is monocyclic heteroaryl. In certain embodiments, at least one $R^B$ is 5-membered monocyclic heteroaryl. In certain embodiments, at least one $R^B$ is 5-membered monocyclic heteroaryl, wherein only one of the five atoms in the ring of the heteroaryl is nitrogen, oxygen, or sulfur. In certain embodiments, at least one $R^B$ is 5-membered monocyclic heteroaryl, wherein only two of the five atoms in the ring of the heteroaryl are independently nitrogen, oxygen, or sulfur. In certain embodiments, at least one $R^B$ is 5-membered monocyclic heteroaryl, wherein only three of the five atoms in the ring of the heteroaryl are independently nitrogen, oxygen, or sulfur. In certain embodiments, at least one $R^B$ is tetrazolyl. In certain embodiments, at least one $R^B$ is 6-membered monocyclic heteroaryl. In certain embodiments, at least one $R^B$ is 6-membered monocyclic heteroaryl, wherein only one of the six atoms in the ring of the heteroaryl is nitrogen. In certain embodiments, at least one $R^B$ is 6-membered monocyclic heteroaryl, wherein only two of the six atoms in the ring of the heteroaryl are nitrogen. In certain embodiments, at least one $R^B$ is triazinyl. In certain embodiments, at least one $R^B$ is tetrazinyl. In certain embodiments, at least one $R^B$ is bicyclic heteroaryl, wherein the point of attachment may be on any atom of the bicyclic heteroaryl, as valency permits. In certain embodiments, at least one $R^B$ is a monocyclic heteroaryl fused with phenyl. In certain embodiments, at least one $R^B$ is a 5-membered monocyclic heteroaryl fused with phenyl. In certain embodiments, at least one $R^B$ is a 6-membered monocyclic heteroaryl fused with phenyl. In certain embodiments, at least one $R^B$ is a monocyclic heteroaryl fused with another monocyclic heteroaryl. In certain embodiments, at least one $R^B$ is a 5-membered monocyclic heteroaryl fused with another 5-membered monocyclic heteroaryl. In certain embodiments, at least one $R^B$ is a 5-membered monocyclic heteroaryl fused with a 6-membered monocyclic heteroaryl. In certain embodiments, at least one $R^B$ is a 6-membered monocyclic heteroaryl fused with another 6-membered monocyclic heteroaryl. In certain embodiments, at least one $R^B$ is —$OR^{B1}$. In certain embodiments, at least one $R^B$ is —OMe. In certain embodiments, at least one $R^B$ is —OEt. In certain embodiments, at least one $R^B$ is —OPr. In certain embodiments, at least one $R^B$ is —OBu. In certain embodiments, at least one $R^B$ is —O(pentyl). In certain embodiments, at least one $R^B$ is —O(hexyl). In certain embodiments, at least one $R^B$ is —OPh. In certain embodiments, at least one $R^B$ is —OBn. In certain embodiments, at least one $R^B$ is —O(CH$_2$)$_2$Ph. In certain embodiments, at least one $R^B$ is —OH. In certain embodiments, at least one $R^B$ is —$SR^{B1}$. In certain embodiments, at least one $R^B$ is —SMe. In certain embodiments, at least one $R^B$ is —SH. In certain embodiments, at least one $R^B$ is —N($R^{B1}$)$_2$. In certain embodiments, at least one $R^B$ is —N(Me)$_2$. In certain embodiments, at least one $R^B$ is —NHMe. In certain embodiments, at least one $R^B$ is —NHAc. In certain embodiments, at least one $R^B$ is —NH$_2$. In certain embodiments, at least one $R^B$ is —CN. In certain embodiments, at least one $R^B$ is —SCN. In certain embodiments, at least one $R^B$ is —C(=$NR^{B1}$)$R^{B1}$, —C(=$NR^{B1}$)$OR^{B1}$, or —C(=$NR^{B1}$)N($R^{B1}$)$_2$. In certain embodiments, at least one $R^B$ is —C(=O)$R^{B1}$. In certain embodiments, at least one $R^B$ is —C(=O)$OR^{B1}$. In certain embodiments, at least one $R^B$ is —C(=O)OMe. In certain embodiments, at least one $R^B$ is —C(=O)N($R^{B1}$)$_2$. In certain embodiments, at least one $R^B$ is —C(=O)N(Me)$_2$. In certain embodiments, at least one $R^B$ is —C(=O)NHMe. In certain embodiments, at least one $R^B$ is —C(=O)NH$_2$. In certain embodiments, at least one $R^B$ is —NO$_2$. In certain embodiments, at least one $R^B$ is —$NR^{B1}$C(=O)$R^{B1}$, —$NR^{B1}$C(=O)$OR^{B1}$, or —$NR^{B1}$C(=O)N($R^{B1}$)$_2$. In certain embodiments, at least one $R^B$ is —OC(=O)$R^{B1}$, —OC(=O)$OR^{B1}$, or —OC(=O)N($R^{B1}$)$_2$.

In compounds of Formula (I), two $R^B$ groups may be joined to form a substituted or unsubstituted carbocyclic ring. In certain embodiments, two $R^B$ groups are joined to form a substituted or unsubstituted cyclopropyl ring. In certain embodiments, two $R^B$ groups are joined to form a substituted or unsubstituted cyclobutyl ring. In certain embodiments, two $R^B$ groups are joined to form a substituted or unsubstituted cyclopentyl ring. In certain embodiments, two $R^B$ groups are joined to form a substituted or unsubstituted cyclohexyl ring. In certain embodiments, two $R^B$ groups are joined to form a substituted or unsubstituted cycloheptyl ring. In certain embodiments, two $R^B$ groups are joined to form a substituted or unsubstituted cyclooctyl ring. In certain embodiments, two $R^B$ groups are joined to form a substituted or unsubstituted cyclononyl ring. In certain embodiments, two $R^B$ groups are joined to form a substituted or unsubstituted cyclodecyl ring.

In certain embodiments, two $R^B$ groups are joined to form a substituted or unsubstituted heterocyclic ring. In certain embodiments, two $R^B$ groups are joined to form a substituted or unsubstituted 4-membered heterocyclic ring. In certain embodiments, two $R^B$ groups are joined to form a substituted or unsubstituted 5-membered heterocyclic ring. In certain embodiments, two $R^B$ groups are joined to form

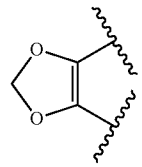 [SMILES: *C1=C(*)OCO1]

or

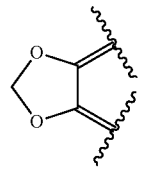 [SMILES: *=C1OCOC1=*]

In certain embodiments, two $R^B$ groups are joined to form a substituted or unsubstituted 6-membered heterocyclic ring. In certain embodiments, two $R^B$ groups are joined to form

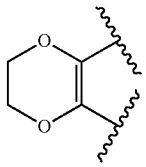

or

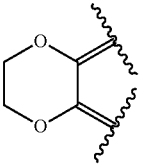

In certain embodiments, two $R^B$ groups are joined to form a substituted or unsubstituted 7-membered heterocyclic ring. In certain embodiments, two $R^B$ groups are joined to form a substituted or unsubstituted 8-membered heterocyclic ring.

In certain embodiments, two $R^B$ groups are joined to form a substituted or unsubstituted 9-membered heterocyclic ring. In certain embodiments, two $R^B$ groups are joined to form a substituted or unsubstituted 10-membered heterocyclic ring.

In certain embodiments, two $R^B$ groups are joined to form a substituted or unsubstituted aryl ring. In certain embodiments, two $R^B$ groups are joined to form a substituted or unsubstituted monocyclic aryl ring. In certain embodiments, two $R^B$ groups are joined to form an unsubstituted phenyl ring. In certain embodiments, two $R^B$ groups are joined to form a substituted phenyl ring. In certain embodiments, two $R^B$ groups are joined to form a substituted or unsubstituted bicyclic aryl ring. In certain embodiments, two $R^B$ groups are joined to form a substituted or unsubstituted naphthyl ring.

In certain embodiments, two $R^B$ groups are joined to form a substituted or unsubstituted heteroaryl ring. In certain embodiments, two $R^B$ groups are joined to form a substituted or unsubstituted monocyclic heteroaryl ring. In certain embodiments, two $R^B$ groups are joined to form a substituted or unsubstituted, 5-membered monocyclic heteroaryl ring. In certain embodiments, two $R^B$ groups are joined to form a substituted or unsubstituted, 6-membered monocyclic heteroaryl ring. In certain embodiments, two $R^B$ groups are joined to form a substituted or unsubstituted, bicyclic heteroaryl ring. In certain embodiments, two $R^B$ groups are joined to form a substituted or unsubstituted, 5,6-membered bicyclic heteroaryl ring. In certain embodiments, two $R^B$ groups are joined to form a substituted or unsubstituted, 6,5-membered bicyclic heteroaryl ring. In certain embodiments, two $R^B$ groups are joined to form a substituted or unsubstituted, 6,6-membered bicyclic heteroaryl ring.

In certain embodiments, $R^B$ is halogen, $C_{1-6}$ alkyl, $-OR^{B1}$, or $-CN$, or two $R^B$ groups are joined to form a substituted or unsubstituted heterocyclic ring, or substituted or unsubstituted aryl ring. In certain embodiments, $R^B$ is halogen, $C_{1-6}$ alkyl, $-OR^{B1}$, or $-CN$, or two $R^B$ groups are joined to form a substituted or unsubstituted, 5-membered, monocyclic heterocyclic ring. In certain embodiments, $R^B$ is halogen, $C_{1-6}$ alkyl, $-OR^{B1}$, or $-CN$, or two $R^B$ groups are joined to form a substituted or unsubstituted, 6-membered, monocyclic heterocyclic ring. In certain embodiments, $R^B$ is halogen, $C_{1-6}$ alkyl, $-OR^{B1}$, or $-CN$, or two $R^B$ groups are joined to form a substituted or unsubstituted phenyl ring.

In certain embodiments, at least one $R^{B1}$ is H. In certain embodiments, at least one $R^{B1}$ is substituted acyl. In certain embodiments, at least one $R^{B1}$ is unsubstituted acyl. In certain embodiments, at least one $R^{B1}$ is acetyl. In certain embodiments, at least one $R^{B1}$ is substituted alkyl. In certain embodiments, at least one $R^{B1}$ is unsubstituted alkyl. In certain embodiments, at least one $R^{B1}$ is $C_{1-6}$ alkyl. In certain embodiments, at least one $R^{B1}$ is methyl. In certain embodiments, at least one $R^{B1}$ is ethyl. In certain embodiments, at least one $R^{B1}$ is propyl. In certain embodiments, at least one $R^{B1}$ is butyl. In certain embodiments, at least one $R^{B1}$ is pentyl. In certain embodiments, at least one $R^{B1}$ is hexyl. In certain embodiments, at least one $R^{B1}$ is substituted alkenyl. In certain embodiments, at least one $R^{B1}$ is unsubstituted alkenyl. In certain embodiments, at least one $R^{B1}$ is vinyl. In certain embodiments, at least one $R^{B1}$ is substituted alkynyl. In certain embodiments, at least one $R^{B1}$ is unsubstituted alkynyl. In certain embodiments, at least one $R^{B1}$ is ethynyl. In certain embodiments, at least one $R^{B1}$ is substituted carbocyclyl. In certain embodiments, at least one $R^{B1}$ is unsubstituted carbocyclyl. In certain embodiments, at least one $R^{B1}$ is cylcopropyl. In certain embodiments, at least one $R^{B1}$ is cylcobutyl. In certain embodiments, at least one $R^{B1}$ is cyclopentyl. In certain embodiments, at least one $R^{B1}$ is cyclohexyl. In certain embodiments, at least one $R^{B1}$ is cycloheptyl. In certain embodiments, at least one $R^{B1}$ is substituted heterocyclyl. In certain embodiments, at least one $R^{B1}$ is unsubstituted heterocyclyl. In certain embodiments, at least one $R^{B1}$ is substituted aryl. In certain embodiments, at least one $R^{B1}$ is unsubstituted aryl. In certain embodiments, at least one $R^{B1}$ is substituted phenyl. In certain embodiments, at least one $R^{B1}$ is unsubstituted phenyl. In certain embodiments, at least one $R^{B1}$ is substituted heteroaryl. In certain embodiments, at least one $R^{B1}$ is unsubstituted heteroaryl. In certain embodiments, at least one $R^{B1}$ is substituted pyridyl. In certain embodiments, at least one $R^{B1}$ is unsubstituted pyridyl. In certain embodiments, at least one $R^{B1}$ is a nitrogen protecting group when attached to a nitrogen atom. In certain embodiments, at least one $R^{B1}$ is Bn, Boc, Cbz, Fmoc, trifluoroacetyl, triphenylmethyl, or Ts when attached to a nitrogen atom. In certain embodiments, $R^{B1}$ is an oxygen protecting group when attached to an oxygen atom. In certain embodiments, $R^{B1}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{B1}$ is a sulfur protecting group when attached to a sulfur atom. In certain embodiments, $R^{B1}$ is acetamidomethyl, t-Bu, 3-nitro-2-pyridine sulfenyl, 2-pyridine-sulfenyl, or triphenylmethyl when attached to a sulfur atom. In certain embodiments, two $R^{B1}$ groups are joined to form a substituted heterocyclic ring. In certain embodiments, two $R^{B1}$ groups are joined to form an unsubstituted heterocyclic ring. In certain embodiments, two $R^{B1}$ groups are joined to form a substituted heteroaryl ring. In certain embodiments, two $R^{B1}$ groups are joined to form an unsubstituted heteroaryl ring.

In certain embodiments, m is 0. In certain embodiments, m is 1. In certain embodiments, m is 2. In certain embodiments, m is 3. In certain embodiments, m is 4. In certain embodiments, m is 5.

Compounds of Formula (I) include a substituent $R^C$. In certain embodiments, $R^C$ is H. In certain embodiments, $R^C$ is $C_{1-6}$ alkyl. In certain embodiments, $R^C$ is methyl. In certain embodiments, $R^C$ is Bn. In certain embodiments, $R^C$ is ethyl. In certain embodiments, $R^C$ is propyl. In certain embodiments, $R^C$ is butyl. In certain embodiments, $R^C$ is pentyl. In certain embodiments, $R^C$ is hexyl.

In compounds of Formula (I), $X^1$ is a divalent linker moiety. In certain embodiments, $X^1$ is $-O-$. In certain embodiments, $X^1$ is $-S-$. In certain embodiments, $X^1$ is $-NR^D-$. In certain embodiments, $X^1$ is $-NH-$. In certain embodiments, $X^1$ is $-C(R^E)_2-$. In certain embodiments, $X^1$ is $-CH_2-$. In certain embodiments, $X^1$ is $-CHMe-$. In certain embodiments, $X^1$ is $-C(Me)_2-$. In certain embodiments, $X^1$ is $-C(=C(R^E)_2)-$. In certain embodiments, $X^1$ is $-C(=CH_2)-$.

In compounds of Formula (I), $X^2$ is a divalent linker moiety. In certain embodiments, $X^2$ is $-O-$. In certain embodiments, $X^2$ is $-S-$. In certain embodiments, $X^2$ is $-NR^D-$. In certain embodiments, $X^2$ is $-NH-$. In certain embodiments, $X^2$ is $-C(R^E)_2-$. In certain embodiments, $X^2$ is $-CH_2-$. In certain embodiments, $X^2$ is $-CHMe-$. In certain embodiments, $X^2$ is $-C(Me)_2-$. In certain embodiments, $X^2$ is $-C(=C(R^E)_2)-$. In certain embodiments, $X^2$ is $-C(=CH_2)-$.

In certain embodiments, $R^D$ is H. In certain embodiments, $R^D$ is $C_{1-6}$ alkyl. In certain embodiments, $R^D$ is methyl. In certain embodiments, $R^D$ is ethyl. In certain embodiments, $R^D$ is propyl. In certain embodiments, $R^D$ is butyl. In certain embodiments, $R^D$ is a nitrogen protecting group. In certain embodiments, $R^D$ is Bn, BOC, Cbz, Fmoc, trifluoroacetyl, triphenylmethyl, or Ts. In certain embodiments, $R^D$ and one $R^B$ group are joined to form a substituted heterocyclic ring. In certain embodiments, $R^D$ and one $R^B$ group are joined to form an unsubstituted heterocyclic ring. In certain embodiments, $R^D$ and one $R^B$ group are joined to form a substituted or unsubstituted 4-membered heterocyclic ring. In certain embodiments, $R^D$ and one $R^B$ group are joined to form a substituted or unsubstituted 5-membered heterocyclic ring. In certain embodiments, $R^D$ and one $R^B$ group are joined to form a substituted or unsubstituted 6-membered heterocyclic ring. In certain embodiments, $R^D$ and one $R^B$ group are joined to form a substituted or unsubstituted 7-membered heterocyclic ring. In certain embodiments, $R^D$ and one $R^B$ group are joined to form a substituted or unsubstituted 8-membered heterocyclic ring. In certain embodiments, $R^D$ and one $R^B$ group are joined to form a substituted or unsubstituted 9-membered heterocyclic ring. In certain embodiments, $R^D$ and one $R^B$ group are joined to form a substituted or unsubstituted 10-membered heterocyclic ring.

In certain embodiments, at least one $R^E$ is H. In certain embodiments, at least one $R^E$ is halogen. In certain embodiments, at least one $R^E$ is F. In certain embodiments, at least one $R^E$ is Cl. In certain embodiments, at least one $R^E$ is Br. In certain embodiments, at least one $R^E$ is I (iodine). In certain embodiments, at least one $R^E$ is $C_{1-6}$ alkyl. In certain embodiments, at least one $R^E$ is methyl. In certain embodiments, at least one $R^E$ is ethyl. In certain embodiments, at least one $R^E$ is propyl. In certain embodiments, at least one $R^E$ is butyl. In certain embodiments, at least one $R^E$ is pentyl. In certain embodiments, at least one $R^E$ is hexyl.

In compounds of Formula (I), two $R^E$ groups may be joined to form a substituted or unsubstituted carbocyclic ring. In certain embodiments, two $R^E$ groups are joined to form a substituted or unsubstituted cyclopropyl ring. In certain embodiments, two $R^E$ groups are joined to form a substituted or unsubstituted cyclobutyl ring. In certain embodiments, two $R^E$ groups are joined to form a substituted or unsubstituted cyclopentyl ring. In certain embodiments, two $R^E$ groups are joined to form a substituted or unsubstituted cyclohexyl ring. In certain embodiments, two $R^E$ groups are joined to form a substituted or unsubstituted cycloheptyl ring.

In compounds of Formula (I), one $R^E$ group and one $R^B$ group may be joined to form a substituted or unsubstituted carbocyclic ring. In certain embodiments, one $R^E$ group and one $R^B$ group are joined to form a substituted or unsubstituted cyclopropyl ring. In certain embodiments, one $R^E$ group and one $R^B$ group are joined to form a substituted or unsubstituted cyclobutyl ring. In certain embodiments, one $R^E$ group and one $R^B$ group are joined to form a substituted or unsubstituted cyclopentyl ring. In certain embodiments, one $R^E$ group and one $R^B$ group are joined to form a substituted or unsubstituted cyclohexyl ring. In certain embodiments, one $R^E$ group and one $R^B$ group are joined to form a substituted or unsubstituted cycloheptyl ring.

In certain embodiments, one $R^E$ group and one $R^B$ group are joined to form a substituted or unsubstituted heterocyclic ring. In certain embodiments, one $R^E$ group and one $R^B$ group are joined to form a substituted or unsubstituted 4-membered heterocyclic ring. In certain embodiments, one $R^E$ group and one $R^B$ group are joined to form a substituted or unsubstituted 5-membered heterocyclic ring. In certain embodiments, one $R^E$ group and one $R^B$ group are joined to form a substituted or unsubstituted 6-membered heterocyclic ring. In certain embodiments, one $R^E$ group and one $R^B$ group are joined to form a substituted or unsubstituted 7-membered heterocyclic ring. In certain embodiments, one $R^E$ group and one $R^B$ group are joined to form a substituted or unsubstituted 8-membered heterocyclic ring. In certain embodiments, one $R^E$ group and one $R^B$ group are joined to form a substituted or unsubstituted 9-membered heterocyclic ring. In certain embodiments, one $R^E$ group and one $R^B$ group are joined to form a substituted or unsubstituted 10-membered heterocyclic ring.

In certain embodiments, one $R^E$ group and one $R^B$ group are joined to form a substituted or unsubstituted aryl ring. In certain embodiments, one $R^E$ group and one $R^B$ group are joined to form a substituted or unsubstituted monocyclic aryl ring. In certain embodiments, one $R^E$ group and one $R^B$ group are joined to form a substituted or unsubstituted phenyl ring. In certain embodiments, one $R^E$ group and one $R^B$ group are joined to form a substituted or unsubstituted bicyclic aryl ring. In certain embodiments, one $R^E$ group and one $R^B$ group are joined to form a substituted or unsubstituted naphthyl ring.

In certain embodiments, one $R^E$ group and one $R^B$ group are joined to form a substituted or unsubstituted heteroaryl ring. In certain embodiments, one $R^E$ group and one $R^B$ group are joined to form a substituted or unsubstituted monocyclic heteroaryl ring. In certain embodiments, one $R^E$ group and one $R^B$ group are joined to form a substituted or unsubstituted 5-membered monocyclic heteroaryl ring. In certain embodiments, one $R^E$ group and one $R^B$ group are joined to form an unsubstituted furan ring. In certain embodiments, one $R^E$ group and one $R^B$ group are joined to form substituted furan ring. In certain embodiments, one $R^E$ group and one $R^B$ group are joined to form a substituted or unsubstituted 6-membered monocyclic heteroaryl ring. In certain embodiments, one $R^E$ group and one $R^B$ group are joined to form a substituted or unsubstituted, bicyclic heteroaryl ring. In certain embodiments, one $R^E$ group and one $R^B$ group are joined to form a substituted or unsubstituted, 5,6-membered bicyclic heteroaryl ring. In certain embodiments, one $R^E$ group and one $R^B$ group are joined to form a substituted or unsubstituted, 6,5-membered bicyclic heteroaryl ring. In certain embodiments, one $R^E$ group and one $R^B$ group are joined to form a substituted or unsubstituted, 6,6-membered bicyclic heteroaryl ring.

In certain embodiments, $X^1$ and $X^2$ are each —$CH_2$—. In certain embodiments, $X^1$ and $X^2$ are each —$CHR^E$—. In certain embodiments, $X^1$ and $X^2$ are each —$CHR^E$—; and two $R^E$ groups are joined to form a substituted or unsubstituted carbocyclic ring. In certain embodiments, —$X^1$—$X^2$— is In certain embodiments, —$X^1$—$X^2$— is or In certain embodiments, —X¹—X²— is

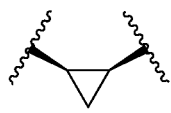 [SMILES: *[C@@H]1C[C@@H]1*]

or

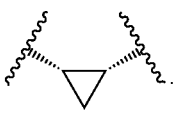.

In certain embodiments, X¹ is —O—, —S—, or —NR$^D$—; and X² is —CH$_2$— or —CHR$^E$—. In certain embodiments, X¹ is —O—, —S—, or —NR$^D$—; and X² is —CHR$^E$— or —C(=CHR$^E$)—. In certain embodiments, X¹ is —O—; and X² is —CHR$^E$—. In certain embodiments, X¹ is —S—; and X² is —CHR$^E$—. In certain embodiments, X¹ is —NR$^D$—; and X² is —CHR$^E$—. In certain embodiments, X¹ is —NH—; and X² is —CHR$^E$—. In certain embodiments, X¹ is —O—; and X² is —CH$_2$—. In certain embodiments, X¹ is —S—; and X² is —CH$_2$—. In certain embodiments, X¹ is —NR$^D$—; and X² is —CH$_2$—. In certain embodiments, X¹ is —NH—; and X² is —CH$_2$—. In certain embodiments, X¹ is —O—; and X² is —C(=CHR$^E$)—. In certain embodiments, X¹ is —S—; and X² is —C(=CHR$^E$)—. In certain embodiments, X¹ is —NR$^D$—; and X² is —C(=CHR$^E$)—. In certain embodiments, X¹ is —NH—; and X² is —C(=CHR$^E$)—.

In certain embodiments, X¹ is —O—, —S—, or —NR$^D$—; X² is —CHR$^E$— or —C(=CHR$^E$)—; and R$^E$ and one R$^B$ group are joined to form a substituted or unsubstituted heterocyclic ring. In certain embodiments, X¹ is —O—, —S—, or —NR$^D$—; X² is —CHR$^E$— or —C(=CHR$^E$)—; and R$^E$ and one R$^B$ group are joined to form a substituted or unsubstituted, 4-membered, monocyclic heterocyclic ring. In certain embodiments, X¹ is —O—, —S—, or —NR$^D$—; X² is —CHR$^E$— or —C(=CHR$^E$)—; and R$^E$ and one R$^B$ group are joined to form a substituted or unsubstituted, 5-membered, monocyclic heterocyclic ring. In certain embodiments, X¹ is —O—, —S—, or —NR$^D$—; X² is —CHR$^E$— or —C(=CHR$^E$)—; and R$^E$ and one R$^B$ group are joined to form a substituted or unsubstituted, 6-membered, monocyclic heterocyclic ring. In certain embodiments, X¹ is —O—, —S—, or —NR$^D$—; X² is —CHR$^E$— or —C(=CHR$^E$)—; and R$^E$ and one R$^B$ group are joined to form a substituted or unsubstituted, 7-membered, monocyclic heterocyclic ring. In certain embodiments, X¹ is —O—, —S—, or —NR$^D$—; X² is —CHR$^E$— or —C(=CHR$^E$)—; and R$^E$ and one R$^B$ group are joined to form a substituted or unsubstituted heteroaryl ring. In certain embodiments, X¹ is —O—, —S—, or —NR$^D$—; X² is —CHR$^E$— or —C(=CHR$^E$)—; and R$^E$ and one R$^B$ group are joined to form a substituted or unsubstituted, 5-membered, monocyclic heteroaryl ring. In certain embodiments, X¹ is —O—, —S—, or —NR$^D$—; X² is —CHR$^E$— or —C(=CHR$^E$)—; and R$^E$ and one R$^B$ group are joined to form a substituted or unsubstituted furanyl ring. In certain embodiments, X¹ is —O—, —S—, or —NR$^D$—; X² is —CHR$^E$— or —C(=CHR$^E$)—; and R$^E$ and one R$^B$ group are joined to form a substituted or unsubstituted, 6-membered, monocyclic heteroaryl ring.

In certain embodiments, the compound of Formula (I) is of the formula:

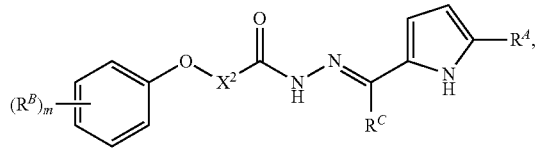

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

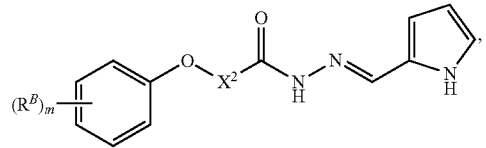

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

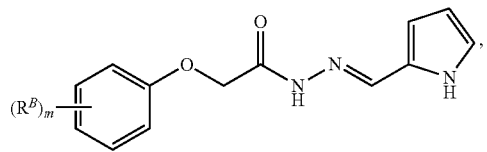

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

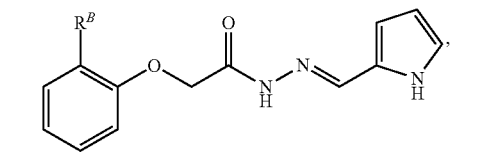

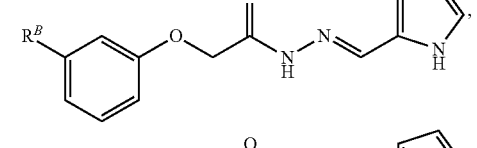

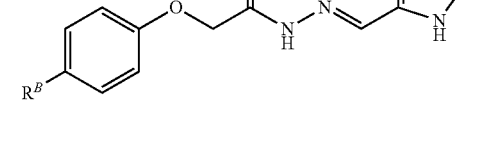

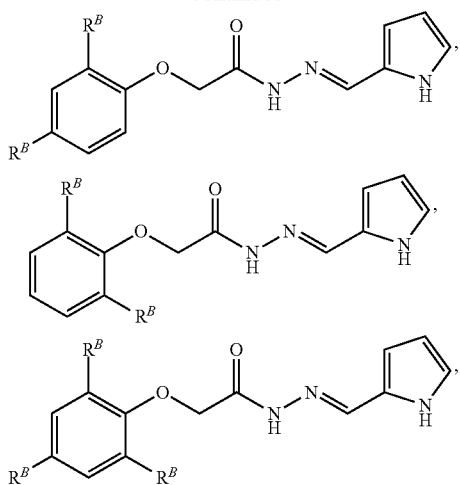

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

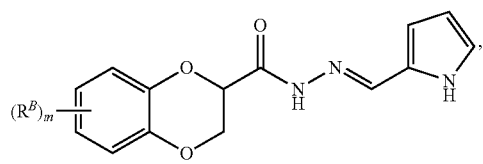

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

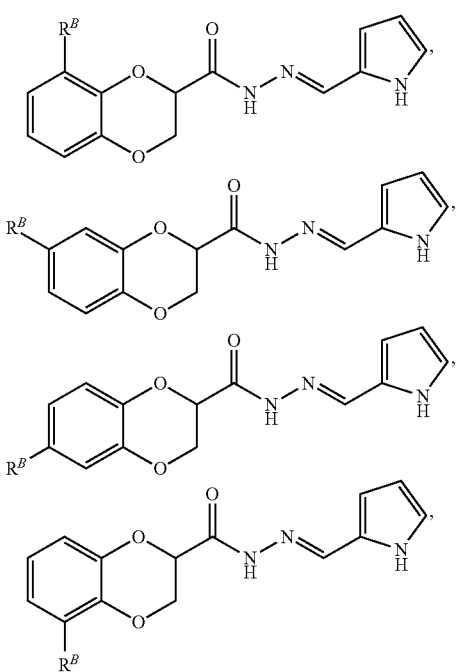

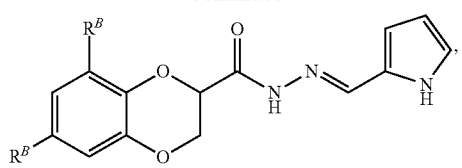

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

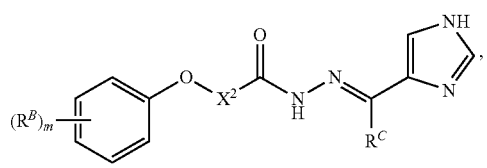

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

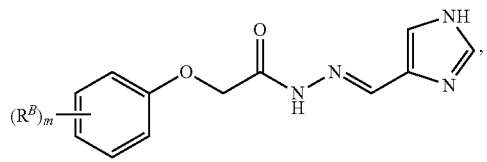

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

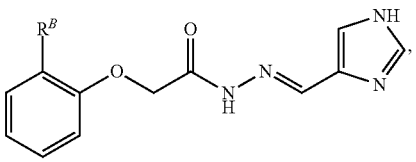

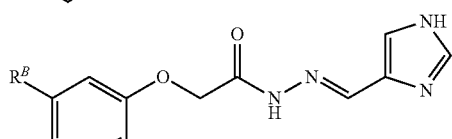

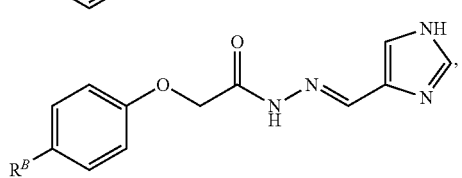

-continued

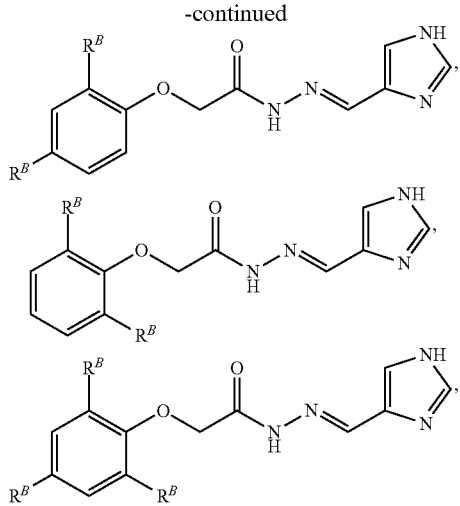

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

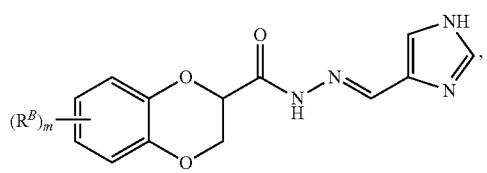

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

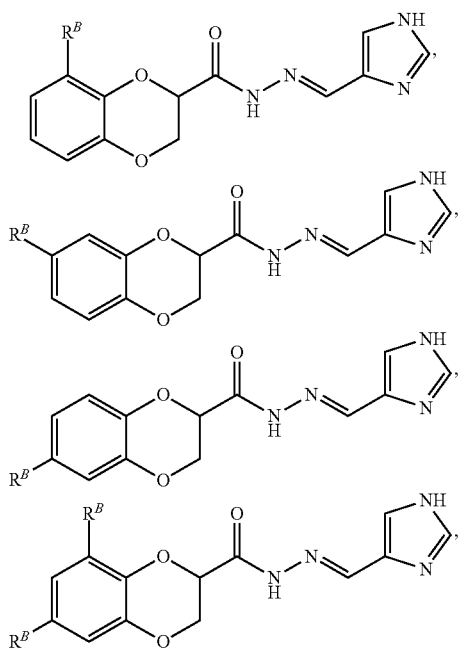

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

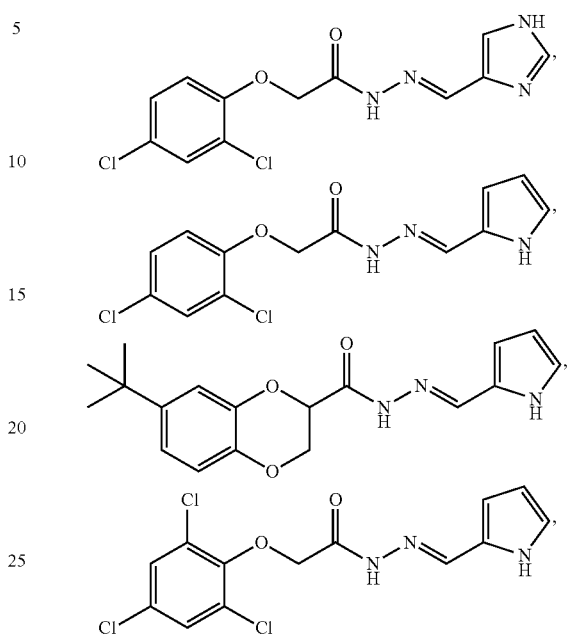

or a pharmaceutically acceptable salt, solvate, hydrate, polymorph, co-crystal, tautomer, stereoisomer, isotopically labeled derivative, or prodrug thereof.

Without limitation, as described in the Examples, thapsigargin was identified using the inventive methods as an ER-stress inducing compound having selective toxicity towards certain cancer stem cells. The invention encompasses use of thapsigargin, thapsigargin derivatives and structurally similar compounds in the compositions and methods of the invention.

Without limitation, as described in the Examples, tunicamycin was identified using the inventive methods as an ER-stress inducing compound having selective toxicity towards certain cancer stem cells. The invention encompasses use of tunicamycin, tunicamycin derivatives and structurally similar compounds in the compositions and methods of the invention.

Without limitation, as described in the Examples, dithiothreitol was identified using the inventive methods as an ER-stress inducing compound having selective toxicity towards certain cancer stem cells. The invention encompasses use of dithiothreitol, dithiothreitol derivatives and structurally similar compounds in the compositions and methods of the invention.

Without limitation, as described in the Examples, A23187 was identified using the inventive methods as an ER-stress inducing compound having selective toxicity towards certain cancer stem cells. The invention encompasses use of A23187, A23187 derivatives and structurally similar compounds in the compositions and methods of the invention.

Cancer Stem Cells, Stress Programs and Epithelial to Mesenchymal Transitions:

Aspects of the invention provided herein relate to the discovery of functional connections between cancer cell malignancy and a conserved stress response program. In some embodiments, it has been determined that cancer stem cells (CSCs) constitutively activate the PERK-eIF2α branch of the UPR. In some embodiments, it has been determined that constitutive UPR activation is a consequence of increased ECM production by CSCs. In some embodiments, it has been determined that increased secretory load sensitizes CSCs to perturbants of ER function, presenting a unique vulnerability to malignant cancer cells.

In some embodiments, CSCs activate the UPR in response to an increased secretory load. In some embodiments, cancer cell invasiveness, which involves secretion of ECM components and remodeling enzymes, entails UPR induction. In some embodiments, cancer cell invasiveness is accompanied by the malignant traits conferred by UPR induction. In some embodiments, invasiveness, via UPR induction, gives rise to one or more other traits possessed by CSCs.

With regard to the UPR pathway, in some embodiments, PERK-eIF2α signaling is substantially constitutively activated in CSCs. In some embodiments, selective utilization of UPR pathways occurs in other contexts, e.g., B cells need XBP1 to differentiate into secretory plasma cells; and osteoblasts utilize PERK to differentiate into functional bone-matrix secreting cells. Although, in some embodiments, PERK-eIF2α signaling is constitutively activated, in such embodiments, ER perturbants strongly induced three branches of the UPR in CSCs. Thus, in some embodiments, massive UPR caused by chemical perturbants may be distinct from induction associated with secretory cell differentiation. In some embodiments, cytosolic kinases may contribute to eIF2α phosphorylation. In some embodiments, increased eIF2α phosphorylation in CSCs may be a consequence of their increased ER load, because inhibition of major secretory proteins (e.g., PAI1, FN1) reduced eIF2α phosphorylation in response to chemical perturbants.

In some embodiments, PAI1 and FN1 secretion for cell migration is consistent with the ability of specific ECM components to positively or negatively modulate cancer progression. In some embodiments, other ECM components could well influence tumorsphere-forming ability. Moreover, CSCs from different tumors may utilize distinct ECM components to modulate their malignant phenotypes.

In some embodiments, differentiation state factors and cellular processes are: (i) involved in maintenance (or survival) of cells in a particular state, (ii) involved in the transition of cells between states, or (iii) involved in the functions of a particular state. In some embodiments, RNAi screens identify genes involved in the first two classes, but not the third (increased ECM secretion and UPR activation are in the third class). In some embodiments, genes in the third class can be discovered by combining RNAi screens with selectively lethal perturbations. In some embodiments, the method has two steps: first, an experimental manipulation is identified which is selectively toxic towards a specific cell-state; this perturbation could be chemical, genetic, or environmental; second, RNAi screens are used to find genes that interact with the selective perturbation. With selective perturbation, inhibition of class (iii) genes has an observable effect, e.g., the selectively toxic perturbation confers upon these genes a viability phenotype.

In some embodiments, epithelial-derived mesenchymal stem-like cells are provided that are useful in the methods of the invention. As used herein, the term "epithelial-derived mesenchymal stem-like cells" refers to cells of an epithelial origin that have acquired (e.g., through transdifferentiation) one or more mesenchymal stem cell related characterisitics. In some embodiments, epithelial-derived mesenchymal stem-like cells are cells of an epithelial origin that have undergo an epithelial-to-mesenchymal transition (EMT). Cells (e.g., cancer cells) can be induced to undergo an EMT through a number of genetic perturbations, e.g. via the overexpression of particular factors (e.g., Twist, Snail, TGF-beta, or MMPs), or by the inhibition of adherens junction proteins such as E-Cadherin. Cells that have been induced into EMT, irrespective of the inducing method used, express similar phenotypic traits and protein markers (e.g., biomarkers), indicating that the EMT is a core differentiation program. The present invention relates to the discovery that cells that have been induced into EMT share many of the properties of cancer stem cells, including the expression of cell surface markers associated with cancer stem cells, growth in suspension culture, tumor formation at low cell numbers in vivo, and resistance to certain standard chemotherapy drugs. Thus, the state of differentiation exhibited by cells that have undergone an epithelial-to-mesenchymal transition, also referred to as mesenchymal transdifferentiation, or epithelial-to-mesenchymal transdifferentiation, can be exploited to identify therapies that specifically target cancer stem cells. In some embodiments, methods are provided to induce an epithelial-mesenchymal transition (e.g., to produce test cells).

As used herein, an "epithelial to mesenchymal transition" (EMT) refers to a transformation, or partial transformation, of an epithelial cell into a cell having one or more mesenchymal charateristics that also has one or more properties of a cancer or non-cancer stem cell. The one or more cancer or non-cancer stem cell properties may include the presence or absence (high expression levels or low expression levels) of one or more proteins (e.g., cell surface markers) and/or an increase in one or more (at least 2, at least 3, at least 4, at least 5, at least 6) functional properties including the ability to grow (proliferate) in suspension cultures, ability to form tumors in vivo at low cell seeding numbers, resistance to certain chemotherapies (e.g., resistance to paclitaxel), metastatic ability, migration ability, resistance to apoptosis or anoikis, scattering, and elongation of cell shape. It is to be understood that the extent to which a cell that has undergone an EMT exhibits an increase or decrease in the expression of one or more proteins or an increase in one or more functional properties of a cancer stem cell may be assessed by performing a comparison with a control cell, e.g., a cell that has not undergone an EMT (a negative control cell) or a cell that has undergone an EMT (a positive control cell), e.g., a cancer stem cell.

In some embodiments, EMT is a non-neoplastic contexts occurs under conditions of stress and is associated with ECM production. In physically disrupted epithelial tissues, cells surrounding a wound may rapidly undergo EMT—this may occur immediately prior to new ECM deposition and migration to fill the wound. As another example, EMT occurs during fibrosis—a condition characterized by excessive ECM production. Both physical wounding and fibrosis involve inflammation and cellular stress; similarly, tumors have been described as wounds that do not heal. Hence, in some embodiments, ECM synthesis and UPR activation by CSCs reflect characteristics present in a corresponding normal epithelial cell state. In some embodiments, cancer cells have been shown to express differentiation-related phenotypes present in their non-cancerous cellular precursors Examples of proteins for which increased expression in a cell that has undergone an EMT, compared with a cell that has not undergone an EMT, is indicative of the EMT includes N-cadherin, Vimentin, Fibronectin, Snail1 (Snail), Snail2 (Slug), Twist, Goosecoid, FOXC2, Sox10, MMP-2, MMP-3, MMP-9, Integrin vβ6, CD44, and ESA. Examples of proteins for which decreased expression in a cell that has undergone an EMT, compared with a cell that has not undergone an EMT, is indicative of the EMT includes E-cadherin, Desmoplakin, Cytokeratin, Occludin, and CD24. The extent to which a epithelial cell has undergone an EMT may be assessed by determining the expression of at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or more proteins. The expression of such proteins may be determined using a variety of assay methods including those disclosed herein and others which are known in the art. It is to be understood that some proteins whose expression levels are indicative of an EMT in a cell are also proteins that may cause the EMT to occur. For example, overexpression of Twist in an epithelial cell causes the cell to undergo an EMT. Similarly, a reduction in expression of E-cadherin in an epithelial cell causes the cell to undergo an EMT. Thus, when an EMT is brought about by increasing (e.g., by cDNA mediated overexpression) the expression of a protein such as Twist or decreasing (e.g., by RNAi mediated inhibition) the expression of a protein such as E-cadherin alterations in the expression of other proteins (e.g., CD44, Desmoplakin) may serve as suitable indicators of the EMT.

It is to be understood that functional properties of cancer or non-cancer stem cells may be assessed using a variety of methods known in the art. Growth in suspension cultures, for example, may be assessed by growing in a spinner flask cells that have undergone an EMT and measuring the change in cell number in the spinner flask over time. This change in cell number may be compared with the change in cell number of control cells that have not undergone an EMT and which have been grown under same or similar conditions. Up to a 10%, 20%, 30%, 40%, 50%, 60%, 70%, 80%, 90%, 100%, or more increase in doubling time of cells grown in suspension culture that have undergone an EMT compared with control cells grown under the same or similar conditions, but that have not undergone an EMT, may be indicative of an increased ability to grow in suspension.

The ability of cells that have undergone an EMT to form tumors in vivo at low cell seeding numbers may be assessed by a comparison with control cells that have not undergone an EMT. The ability to form tumors in vivo at low cell seeding numbers depends on a variety of factors which will be apparent to the skilled artisan, including for example the type of animal (e.g., a mouse) in which the cells are injected, the location where the cells are seeded (e.g., injected), and the ability of the animal to mount an immune response against the cells. As used herein, "low cell seeding numbers" means seeding of up to $10^0$, up to $10^1$, up to $10^2$, up to $10^3$, up to $10^4$, up to $10^5$, up to $10^6$ or more cells. The number of tumors formed in vivo following seeding of cells (e.g., a one or more locations or in one or more animals) is an exemplary parameter by which this comparison with a control may be made. The size (e.g., volume) of tumors formed in vivo following seeding of cells is another exemplary parameter by which this comparison with a control may be made. Up to a 10%, 20%, 30%, 40%, 50%, 60%, 70%, 80%, 90%, 100%, or more increase in tumor incidence or size, for example, may be indicative of an increased ability to form tumors in vivo at low cell seeding numbers.

Other methods for assessing functional properties of cancer or non-cancer stem cells are disclosed herein and elsewhere, and will be apparent to the skilled artisan. (See, e.g., S M Frisch and H Francis, Disruption of epithelial cell-matrix interactions induces apoptosis, J Cell Biol. 1994 February; 124(4):619-26; Mushinski J F, et al, Inhibition of tumor cell motility by the interferon-inducible GTPase MxA. J Biol Chem. 2009 Mar. 18; Liu Y N, et al., Activated androgen receptor downregulates E-cadherin gene expression and promotes tumor metastasis. Mol Cell Biol. 2008 December; 28(23):7096-108; Carpenter P M, et al., Motility Induction in Breast Carcinoma by Mammary Epithelial Laminin 332 (Laminin 5), Mol Cancer Res. 2009 Apr. 7; Nakamura M, et al., Polarized hydroxyapatite promotes spread and motility of osteoblastic cells. J Biomed Mater Res A. 2009 Mar. 9; Gu W, et al., Measuring cell motility using quantum dot probes. Methods Mol Biol. 2007; 374:125-31; and Sakai K, et al., Inducible expression of p57KIP2 inhibits glioma cell motility and invasion. J Neurooncol. 2004 July; 68(3):217-23.)

The present invention discloses methods for inducing EMT in cells. In certain embodiments, the epithelial to mesenchymal transition is brought about by inhibiting the expression or activity of E-Cadherin in the cell. The expression or activity of E-Cadherin can be inhibited by using methods known to one of ordinary skill in the art. Exemplary methods for inhibiting E-cadherin expression or activity include contacting a cell with a small interfering nucleic acid complementary to E-Cadherin mRNA, contacting a cell with a blocking antibody to E-cadherin; inducing the expression of dysadherin, for example by cDNA-based overexpression of dysadherin, in a cell; and interfering with cell-polarity genes in the cell. For example, depletion of Scribble disrupts E-cadherin-mediated cell-cell adhesion and induces EMT (Qin Y, et al., J Cell Biol 2005; 171:1061-71). Thus, in some embodiments, inhibition of Scribble, such as by RNA interference, can induce an EMT. Also, genetic screens in *Drosophila* identified a number of genes affecting cell polarity whose inactivation results in loss of E-cadherin expression (Pagliarini R A, et al., Science 2003; 302:1227-31). Other exemplary methods for interfering with cell polarity genes to induce EMT are known in the art.

In certain embodiments, the activity of E-cadherin is inhibited by RNA interference. Methods for inhibiting gene expression, such as E-cadherin expression, by RNA interference are disclosed herein and known in the art. In some embodiments, a cell is transfected with a small interfering nucleic acid complementary to E-Cadherin mRNA in the cell to inhibit E-cadherin activity in the cell. Exemplary small interfering nucleic acids are disclosed herein and are known to persons skilled in the art. Methods for transfection of small interfering nucleic acids (e.g., siRNA) are well known in the art and examples are disclosed herein. In some embodiments, the cell has a stably integrated transgene that expresses a small interfering nucleic acid (e.g., shRNA, miRNA) that is complementary to E-Cadherin mRNA and that causes the downregulation of E-Cadherin mRNA through the RNA interference pathway.

Various strategies for gene knockdown known in the art can be used to inhibit the expression of a gene, for example E-cadherin and others disclosed herein that are useful for inducing EMT. For example, gene knockdown strategies may be used that make use of RNA interference (RNAi) and/or microRNA (miRNA) pathways including small interfering RNA (siRNA), short hairpin RNA (shRNA), double-stranded RNA (dsRNA), miRNAs, and other nucleotide-based molecules known in the art. In one embodiment, vector-based RNAi modalities (e.g., shRNA or shRNA-mir expression constructs) are used to reduce expression of a gene (e.g., E-cadherin) in a cell.

A broad range of RNAi-based modalities could be also employed to inhibit expression of a gene in a cell, such as siRNA-based oligonucleotides and/or altered siRNA-based oligonucleotides. Altered siRNA based oligonucleotides are those modified to alter potency, target affinity, safety profile and/or stability, for example, to render them resistant or partially resistant to intracellular degradation. Modifications, such as phosphorothioates, for example, can be made to oligonucleotides to increase resistance to nuclease degradation, binding affinity and/or uptake. In addition, hydrophobization and bioconjugation enhances siRNA delivery and targeting (De Paula et al., RNA. 13(4):431-56, 2007) and siRNAs with ribo-difluorotoluyl nucleotides maintain gene silencing activity (Xia et al., ASC Chem. Biol. 1(3):176-83, (2006)). siRNAs with amide-linked oligoribonucleosides have been generated that are more resistant to S1 nuclease degradation than unmodified siRNAs (Iwase R et al. 2006 Nucleic Acids Symp Ser 50: 175-176). In addition, modification of siRNAs at the 2'-sugar position and phosphodiester linkage confers improved serum stability without loss of efficacy (Choung et al., Biochem. Biophys. Res. Commun 342(3):919-26, 2006). Other molecules that can be used to inhibit expression of a gene (e.g., a gene, such as E-Cadherin, that negatively regulates EMT) include sense and antisense nucleic acids (single or double stranded), ribozymes, peptides, DNAzymes, peptide nucleic acids (PNAs), triple helix forming oligonucleotides, antibodies, and aptamers and modified form(s) thereof directed to sequences in gene(s), RNA transcripts, or proteins. Antisense and ribozyme suppression strategies have led to the reversal of a tumor phenotype by reducing expression of a gene product or by cleaving a mutant transcript at the site of the mutation (Carter and Lemoine Br. J. Cancer. 67(5):869-76, 1993; Lange et al., Leukemia. 6(11):1786-94, 1993; Valera et al., J. Biol. Chem. 269(46):28543-6, 1994; Dosaka-Akita et al., Am. J. Clin. Pathol. 102(5):660-4, 1994; Feng et al., Cancer Res. 55(10):2024-8, 1995; Quattrone et al., Cancer Res. 55(1):90-5, 1995; Lewin et al., Nat Med. 4(8):967-71, 1998). Ribozymes have also been proposed as a means of both inhibiting gene expression of a mutant gene and of correcting the mutant by targeted trans-splicing (Sullenger and Cech Nature 371(6498):619-22, 1994; Jones et al., Nat. Med. 2(6):643-8, 1996). Ribozyme activity may be augmented by the use of, for example, non-specific nucleic acid binding proteins or facilitator oligonucleotides (Herschlag et al., Embo J. 13(12):2913-24, 1994; Jankowsky and Schwenzer Nucleic Acids Res. 24(3):423-9, 1996). Multitarget ribozymes (connected or shotgun) have been suggested as a means of improving efficiency of ribozymes for gene suppression (Ohkawa et al., Nucleic Acids Symp Ser. (29):121-2, 1993).

In some embodiments, EMT is brought about by modulating the activity of a transcription factor (e.g., a transcription factor that modulates E-cadherin activity). The directionality of the modulation (e.g., inhibiting the activity or inducing the activity of the transcription factor) to induce EMT can be determined or confirmed by a skilled artisan using routine experimentation. In cases where it is desirable to inhibit the activity of a transcription factor, RNA interference is useful. For example, a small interfering nucleic acid, as disclosed herein, complementary to mRNA of a transcription factor can be used to inhibit the activity of the transcription factor. In some embodiments, EMT is brought about by inducing the activity of a transcription factor selected from: Snail1, Snail2, Goosecoid, FoxC2, TWIST, E2A, SIP-1/Zeb-2, dEF1/ZEb1, LEF1, Myc, HMGA2, TAZ, Klf8, HIF-1, HOXB7, SIM2s, and Fos. Exemplary methods for inducing the activity of transcription factors are known in the art. In some cases where it is desirable to induce the activity of a transcription factor exogenous expression of the transcription factor is useful. For example, induction of TWIST expression in a cell is known in the art to inhibit the activity of E-cadherin in the cell and induce EMT. In one embodiment, TWIST is induced in a cell by transfecting the cell with an expression vector encoding TWIST, thereby exogenously expressing TWIST in the cell.

In some embodiments, a cell has a stably integrated transgene that expresses a transcription factor, such as TWIST, that causes an EMT in the cell.

In some embodiments, EMT is brought about by modulating the activity of a signaling pathway in a cell, wherein the signaling pathway is selected from TGF-β, Wnt, BMP, Notch, HGF-Met, EGF, IGF, PDGF, FGF, P38-mapk, Ras, PI3Kinase-Akt, Src, and NF-kB. In some embodiments, the signaling pathway that induces EMT is modulated by contacting a cell with a growth factor selected from: a TGF-β/BMP superfamily member, a Wnt-family member, an FGF family member, a Notch Ligand, an EGF family member, an IGF family member, PDGF, and HGF. In some embodiments, the signaling pathway that induces EMT is modulated by contacting a cell with TGF-$β_1$. Exemplary TGF-β/BMP superfamily members include TGF-β1, TGF-β2, TGF-β3, BMP2, BMP3, BMP4, BMP5, BMP6, BMP7, BMP8a, BMP8b, BMP10, BMP15, GDF1, GDF2, GDF3, GDF5, GDF6, GDF7, Myostatin/GDF8, GDF9, GDF10, GDF11, GDF15, Activin A and B/Inhibin A and B, Anti-müllerian hormone, and Nodal. Exemplary FGF family members include FGF1, FGF2, FGF4, FGF8, FGF10. Exemplary Wnt-family members include WNT1, WNT2, WNT2B/13, WNT3, WNT3A, WNT4, WNT5A, WNT5B, WNT6, WNT7A, WNT7B, WNT8A, WNT8B, WNT9A, WNT9B, WNT10A, WNT10B, WNT11, and WNT16. Exemplary EGF family members include Heparin-binding EGF-like growth factor (HB-EGF), transforming growth factor-α (TGF-α), Amphiregulin (AR), Epiregulin (EPR), Epigen, Betacellulin (BTC), neuregulin-1 (NRG1), neuregulin-2 (NRG2), neuregulin-3 (NRG3), and neureguline-4 (NRG4). Exemplary IGF family members include IGF1 and IGF2.

In some embodiments, the EMT is brought about by subjecting a cell to a stress selected from: hypoxia, irradiation, and chronic chemotherapy treatment. Methods for inducing stress in the cell are known in the art. Exemplary methods are disclosed in Docherty, N G, et al., Am J Physiol Renal Physiol 290: F1202-F1212, 2006 and Manotham K, et al., Kidney Int 65: 871-880, 2004, the contents of which are incorporated in their entirety by reference herein.

Exemplary methods for inducing EMT in a cell are disclosed in Weinberg R A, et al., WO2007/005611; Zavadil J et al., Oncogene 24: 5764-5774, 2005; Sato M, J Clin Invest 112: 1486-1494, 2003; Gregory P A, et al., Nat Cell Biol. Mar. 30, 2008; Zeng R, et. al., J Am Soc Nephrol. 2008 February; 19(2):380-7. Epub 2008 Jan. 9; Krawetz R, et al., Cell Signal. 2008 March; 20(3):506-17; Jiang Y G, et al., Int J Urol. 2007 Nov. 14(11):1034-9; Lo H W, et al., Cancer Res. 2007 Oct. 1, 67(19):9066-76; Lester R D, et al., J Cell Biol. 2007 Jul. 30 178(3):425-36; Moustakas A, et al., Cancer Sci. 2007 October 98(10):1512-20; and Wahab N A, et al., Nephron Exp Nephrol. 2006, 104(4):e129-34, the contents of which are incorporated herein by reference. However, these methods are not meant to be limiting and other appropriate methods will be apparent to one of ordinary skill in the art.

Cells

Aspects of the invention provide test cells and control cells, for example test and control cells that are useful for identifying compounds that specifically target cancer stem cells. As described herein, test or control cells can be primary cells, non-immortalized cell lines, immortalized cell lines, transformed immortalized cell lines, benign tumor derived cells or cell lines, malignant tumor derived cells or cell lines, transgenic cell lines, etc. In some embodiments the tumor is a metastatic tumor, in which case the cells may be derived from the primary tumor or a metastasis. In preferred embodiments, test cells are cells that have undergone an epithelial to mesenchymal transition. Control cells can include both positive and negative controls cells. In one embodiment, a positive control cell is a cancer stem cell, optionally which expresses one or more cancer stem cell biomarker(s). In certain embodiments, a cancer stem cell biomarker is selected from E-Cadherin, TWIST, and a CD44$^+$CD24$^-$ marker profile. Non limiting cancer stem cell biomarkers include: CD20, CD24, CD34, CD38, CD44, CD45, CD105, CD133, CD166, EpCAM, ESA, SCA1, Pecam, Stro1, FOXC2$^{pos}$, N-cadherin$^{high}$, E-cadherin$^{low/neg}$, alpha-catenin$^{low/neg}$, gamma-catenin$^{low/neg}$, vimentin$^{pos}$, and fibronectin$^{pos}$. Other exemplary cancer stem cell markers will be apparent to one of ordinary skill in the art. In some embodiments, a positive control cell is a cell that has undergone an EMT, for example a cell that has reduced E-Cadherin expression.

In some embodiments, a negative control cell is a cancer cell that is not a cancer stem cell, optionally which does not exhibit detectable expression of one or more cancer stem cell biomarker(s). More than one set of control cells may be provided, such as cancer cells that are not cancer stem cells and non-cancer cells. Cells (test or control) may be subjected to one or more genetic or chemical perturbations (e.g., siRNA treatment or Compound treatment) and then incubated for a predetermined time. The predetermined time is a time sufficient to produce a desired effect in a control cell (e.g., inhibit the growth and/or survival thereof).

In some embodiments the cells are mammalian cells, e.g., human cells or non-human animal cells, e.g., cells of non-human primate, rodent (e.g., mouse, rat, guinea pig, rabbit), origin, or interspecies hybrids. In certain embodiments the test and control cells are obtained from a biopsy (e.g., tissue biopsy, fine needle biopsy, etc.) or at surgery for a cancerous or noncancerous condition.

In some embodiments, cells (e.g., test cells, controls cells) of the invention may be derived from a cancer (e.g., naturally occurring cancer). In some embodiments, cells (e.g., test cells, controls cells) of the invention may be derived from a cancer of epithelial origin (e.g., breast cancer). In some embodiments, the cancer from which cells are derived is a colon carcinoma, a pancreatic cancer, a breast cancer, an ovarian cancer, a prostate cancer, a squamous cell carcinoma, a cervical cancer, a lung carcinoma, a small cell lung carcinoma, a bladder carcinoma, a squamous cell carcinoma, a basal cell carcinoma, an adenocarcinoma, a sweat gland carcinoma, a sebaceous gland carcinoma, a papillary carcinoma, a papillary adenocarcinoma, a cystadenocarcinoma, a medullary carcinoma, a bronchogenic carcinoma, a renal cell carcinoma, a hepatocellular carcinoma, a bile duct carcinoma, a choriocarcinoma, a seminoma, a embryonal carcinoma, a Wilms' tumor, melanoma, or a testicular tumor. In one embodiment, cancer is a lung carcinoma. In one embodiment, cancer is a breast carcinoma. Other cancers will be known to one of ordinary skill in the art. In some embodiments the cancer is a spontaneously arising cancer. In some embodiments the cancer is a cancer associated with a known or characteristic genetic mutation or polymorphism. In some embodiments the cancer is an experimentally produced cancer. In some embodiments the cancer is a hormone-responsive cancer. In some embodiments the cells are derived from an early stage cancer or precancerous lesion, e.g., a papilloma, adenoma, dysplastic lesion, etc., or a carcinoma in situ. In some embodiments the cancer is one that is responsive to a chemotherapeutic agent or combination thereof (e.g., any one or more of the chemotherapeutic agents discussed below). In some embodiments the cancer is one that is resistant to a chemotherapeutic agent or combination thereof.

In some embodiments, cancer cells are experimentally produced. Cancer cells can be experimentally produced by a number of methods known in the art that result in transformation of a non-cancer cell (non-transformed cell) to a cancer cell (transformed cell). Such experimentally produced cancer cells may be metastatic or non-metastatic.

In some cases, cancer cells are produced from non-cancer cells by transfecting the non-cancer cells (transiently or stably) with one or more expression vector(s) encoding an oncogene. Such oncogenes, when expressed, lead to neoplastic or hyperplastic transformation of a cell. The oncogene may be a complete sequence of the oncogene, preferably an oncogenic form of the oncogene, or it may be a fragment of the oncogene that maintains the oncogenic potential of the oncogene. Exemplary oncogenes include MYC, SRC, FOS, JUN, MYB, RAS, ABL, BCL2, HOXI1, HOX1 1L2, TAL1/SCL, LMO1, LMO2, EGFR, MYCN, MDM2, CDK4, GLI1, IGF2, activated EGFR, mutated genes, such as FLT3-ITD, mutated of TP53, PAX3, PAX7, BCR/ABL, HER2/NEU, FLT3R, FLT3-ITD, SRC, ABL, TAN1, PTC, B-RAF, PML-RAR-alpha, E2A-PBX1, and NPM-ALK, as well as fusion of members of the PAX and FKHR gene families. Other exemplary oncogenes are well known in the art and several such examples are described in, for example, The Genetic Basis of Human Cancer (Vogelstein, B. and Kinzler, K. W. eds. McGraw-Hill, New York, N. Y., 1998). Homologues of such genes can also be used.

In some cases, cancer cells can be produced from non-cancer cells by transfecting the non-cancer cells (transiently or stably) with one or more expression vector(s) encoding an inhibitory molecule (e.g., shRNA, mirRNA) capable of inhibiting the expression of a tumor suppressor gene. Such inhibitory molecules, when expressed, lead to neoplastic or hyperplastic transformation of a cell. Exemplary tumor suppressor genes include RB, TP53, APC, NF-1, BRCA-1, BRCA-2 and WT-1. Other exemplary tumor suppressor genes are well known in the art.

In some cases, cancer cells can be produced from non-cancer cells by transfecting the non-cancer cells (transiently or stably) with one or more expression vector(s) encoding an inhibitory molecule (e.g., shRNA) capable of inhibiting the expression of a tumor suppressor gene and one or more expression vector(s) encoding an oncogene.

In some embodiments, cells (e.g., test cells, control cells) of the invention are derived from noncancerous tissue. For example, the cells may be derived from any epithelial tissue. One of skill in the art will appreciate that "epithelium" refers to layers of cells that line the cavities and surfaces of structures throughout the body and is also the type of tissue of which many glands are at least in part formed. Such tissues include, for example, tissues found in the breast, gastrointestinal tract (stomach, small intestine, colon), liver, biliary tract, bronchi, lungs, pancreas, kidneys, ovaries, prostate, skin, cervix, uterus, bladder, ureter, testes, exocrine glands, endocrine glands, blood vessels, etc. In some embodiments the epithelium is endothelium or mesothelium. In certain embodiments the cells are human breast epithelial cells. In certain embodiments the cells are noncancerous human breast cells obtained from a reduction mammoplasty. In certain embodiments, the test and control cells are derived from any cell type that normally expresses E-cadherin. In certain embodiments, the test and control cells are of a cell type that does not normally express N-cadherin. In certain embodiments, the test and control cells are of a cell type that normally expresses E-cadherin at levels at least 5, 10, 20, 50, or 100-fold higher levels, on average, than those at which it expresses N-cadherin.

In some embodiments the cells (test and/or control) have been modified, e.g., genetically modified, so as to express, inhibit, or delete one or more oncogenes or tumor suppressor genes. In some embodiments such modification immortalizes the cells. In some embodiments such modification transforms the cells to tumorigenic cells. For example, in certain embodiments test and/or control cells are immortalized by expressing telomerase catalytic subunit (e.g., human telomerase catalytic subunit; hTERT) therein. In certain embodiments test and/or control cells are transformed by expressing SV40 (e.g., early region) or Ras, optionally activated Ras such as H-rasV12, therein. In some embodiments cells are modified or treated so as to have reduced or essentially absent expression and/or functional activity of cell cycle checkpoint or DNA damage sensing proteins, e.g., p16, e.g., p16$^{INK4a}$, p53 and/or retinoblastoma (Rb) proteins. For example, cells can be modified to express a shRNA targeted to one or more of these genes, or to express a viral protein that binds to one or more of these proteins. Combinations of such modifications can be used. For example, cells may be modified to express SV40 large T (LT), hTERT, and H-rasV12. Other means of immortalizing and/or transforming cells are known in the art and are within the scope of the invention.

In certain embodiments of the invention the test cells and control cells are derived from an initial population of substantially identical cells that have not undergone an EMT. Certain of these cells are manipulated so as to render them suitable for use as test cells, e.g., by modifying them so as to be able to induce EMT in a controlled manner and then inducing EMT or by treating them with an agent that induces EMT, e.g., as described above. In certain embodiments such as these the test and control cells are genetically matched but have one or several defined genetic differences such as those described herein that result in the test cells having undergone EMT while the control cells have not undergone EMT. In certain embodiments, two populations of cells derived from the same starting population, wherein one population has been modified by introducing a vector and the other population has not been so modified. In certain embodiments, two populations of cells derived from the same starting population, wherein one population has been modified by introducing an expression construct encoding an inhibitory nucleic acid or protein element and the other population has been modified by introducing an expression construct encoding a control nucleic acid or protein element (e.g., one that would not be expected to inhibit an endogenous cellular gene or protein). Typically the expression constructs are otherwise similar or identical. In certain embodiments of the invention, the test cells and control cells are genetically matched and contain an expression construct (optionally integrated into the genome) comprising a sequence encoding a short interfering RNA capable of inducing EMT (such as a shRNA or miRNA targeted to E-cadherin), wherein the sequence is operably linked to a regulatable (e.g., inducible or repressible) promoter. In certain embodiments of the invention, the test cells and control cells are genetically matched and contain an expression construct (optionally integrated into the genome) comprising a sequence encoding a protein capable of inducing EMT, wherein the sequence is linked to a regulatable (e.g., inducible or repressible) promoter. Regulatable expression systems are known in the art and include, e.g., systems utilizing promoters that are inducible by heavy metals, small molecules, etc. Drug-regulatable promoters that are suited for use in mammalian cells include the tetracycline/doxycycline regulatable promoter systems.

"Genetically matched" includes cells or populations of cells that have largely identical genomes, e.g., their genomes are at least 95%, 98%, 99%, 99.5%, 99.9%, 99.99% identical, or more. Typically, genetically matched cells are derived from the same subject or, in the case of certain species such as mice or rats, from different subjects belonging to a particular inbred strain. In some embodiments genetically matched cells are derived from the same tissue sample. In some embodiments of the invention, test and control cells will have been derived from the same initial population of genetically matched cells and will have undergone no more than 2, 5, 10, 15, 20, 25, 30, 35, 40, 50, 60, 70, 80, 90, or 100 rounds of cell division before being used in an inventive method.

The invention provides genetically matched test cells (or cells that can be induced to undergo an EMT and thereby become suitable for use as test cells) and control cells and kits containing such cells. Without wishing to be bound by any theory and without limiting the invention in any way, by using test and control cells that are genetically matched and differ primarily or essentially in that the test cells have undergone an EMT and the control cells have not, the invention allows identification of compounds that differentially affect the test cells versus the control cells (e.g., compounds that inhibit growth of the test cells to a significantly greater extent than the extent to which they inhibit growth of the control cells) as a result of differences in the test cells and control cells that arise as a consequence of the differentiation state of the cells e.g., as a consequence of the test cells having undergone an EMT (associated with acquiring cancer stem cell-like properties) rather than because of other, possibly unknown, genetic or epigenetic differences in the test and control cells.

Screening for ER-Stress Inducing Compounds

In some embodiments, methods for identifying ER-stress inducing compounds or compositions are provided. In some embodiments, screening may be carried out in vitro or in vivo using any of the assays disclosed herein, or any assay known to one of ordinary skill in the art to be suitable for contacting a test cell with a test compound and assaying for alterations in the growth and/or survival of the test cell and/or ER function of the test cell.

In one aspect compounds are contacted with test cells (and optionally control cells) at a predetermined dose. In one embodiment the dose may be about up to 1 nM. In another embodiment the dose may be between about 1 nM and about 100 nM. In another embodiment the dose may be between about 100 nM and about 10 uM. In another embodiment the dose may be at or above 10 uM. Following incubation for an appropriate time, optionally a predetermined time, the effect of compounds or composition on the growth and/or survival of the test cell is determined by an appropriate method known to one of ordinary skill in the art. Cells can be contacted with compounds for various periods of time. In certain embodiments cells are contacted for between 12 hours and 20 days, e.g., for between 1 and 10 days, for between 2 and 5 days, or any intervening range or particular value. Cells can be contacted transiently or continuously.

If desired, compound can be removed prior to assessing growth and/or survival and/or the ER function of the test cell. As used herein, "suppress", "inhibit", or "reduce" may, or may not, be complete. For example, cell proliferation, may, or may not, be decreased to a state of complete arrest for an effect to be considered one of suppression, inhibition or reduction of cell proliferation. Similarly, gene expression may, or may not, be decreased to a state of complete cessation for an effect to be considered one of suppression, inhibition or reduction of gene expression. Moreover, "suppress", "inhibit", or "reduce" may comprise the maintenance of an existing state and the process of affecting a state change. For example, inhibition of cell proliferation may refer to the prevention of proliferation of a non-proliferating cell (maintenance of a non-proliferating state) and the process of inhibiting the proliferation of a proliferating cell (process of affecting a proliferation state change). Similarly, inhibition of cell survival may refer to killing of a cell, or cells, such as by necrosis or apoptosis, and the process of rendering a cell susceptible to death, such as by inhibiting the expression or activity of an anti-apoptotic regulatory factor. The suppression, inhibition, or reduction may be at least about 5%, 10%, 15%, 20%, 25%, 30%, 35%, 40%, 45%, 50%, 55%, 60%, 65%, 70%, 75%, 80%, 85%, 90%, 95%, 99% of a reference level (e.g., a control level).

In some cases the level of modulation (e.g., suppression, inhibition, or reduction) compared with a control level is statistically significant. As used herein, "statistically significant" refers to a p-value of less than 0.05, e.g., a p-value of less than 0.025 or a p-value of less than 0.01, using an appropriate statistical test (e.g, ANOVA, t-test, etc.).

In certain embodiments, the growth and/or survival of the test cell and/or control cell is determined by an assay selected from: a cell counting assay, a replication labeling assay, a cell membrane integrity assay, a cellular ATP-based viability assay, a mitochondrial reductase activity assay, a caspase activity assay, an Annexin V staining assay, a DNA content assay, a DNA degradation assay, and a nuclear fragmentation assay. Other exemplary assays include BrdU, EdU, or H3-Thymidine incorporation assays; DNA content assays using a nucleic acid dye, such as Hoechst Dye, DAPI, Actinomycin D, 7-aminoactinomycin D or Propidium Iodide; Cellular metabolism assays such as AlamarBlue, MTT, XTT, and CellTitre Glo; Nuclear Fragmentation Assays; Cytoplasmic Histone Associated DNA Fragmentation Assay; PARP Cleavage Assay; TUNEL staining; and Annexin staining.

In one embodiment, gene expression analysis (e.g., microarray, cDNA array, quantitative RT-PCR, RNAse protection assay) is employed to examine the expression of genes whose products mediate cell cycle/growth and/or survival.

In other embodiments, alterations in the growth and/or survival of the test cell and/or control cell is/are assessed by examining protein levels, for example the level of protein encoded by a foregoing cell cycle/growth and/or survival gene. Protein levels can be assessed by an appropriate method known to one of ordinary skill in the art, such as western analysis. Other methods known to one of ordinary skill in the art could be employed to analyze proteins levels, for example immunohistochemistry, immunocytochemistry, ELISA, radioimmunoassays, proteomics methods, such as mass spectroscopy or antibody arrays.

Still other parameters disclosed herein that are relevant assessing cell growth and/or survival can provide assays for screening for compounds. For example, high-content imaging or Fluorescence-activated cell sorting (FACS) of cells may be used. In one embodiment, the effect of a compound on a test cell and/or control cell can be assessed by evaluating the apoptotic state of the test cell using automated microscopic imaging or FACS (See for example United States Patent Publication 20070172818). In some cases, fluorescence-based TUNEL staining (e.g., using a FITC-dUTP with standard TUNEL methods known in the art) can reveal apoptosis in a test cell and/or control cell. Other methods include immunocytochemistry using an antibody (e.g., cleaved PARP, cleaved Lamin A, etc.) to detect caspase activity. In other embodiments, an image-based cell cycle/growth marker can be used, such as one or more of those exemplified in Young D W, et al., Nat Chem Biol. 2008 January; 4(1):59-68. These examples of imaging are not intended to be limiting, and other similar methods will be readily apparent to one of ordinary skill in the art.

In other embodiments, the activity of a cell growth and/or survival gene and/or components of the ER or of UPR signaling, such as those disclosed herein, can be assayed in a compound screen. In one embodiment, the assay comprises an expression vector that includes a regulatory region of a gene of interest operably linked to a sequence that encodes a reporter gene product (e.g., a luciferase enzyme), wherein expression of the reporter gene is correlated with the activation of the gene. In this embodiment assessment of reporter gene expression (e.g., luciferase activity) provides an indirect method for assessing cell growth and/or survival and/or ER function. This and other similar assays will be well known to one of ordinary skill in the art. The reporter gene product could be, without limitation, a fluorescent or luminescent protein, enzyme, or other protein amenable to convenient detection and, optionally, quantitation. Examples include GFP, RFP, BFP, YFP, CYP, SFP, reef coral fluorescent protein, mFruits such as mCherry, luciferase, aequorin and derivatives of any of the foregoing. Enzyme reporter proteins such as beta-galactosidase, alkaline phosphatase, chloramphenicol acetyltransferase, etc., are also of use. In other embodiments, chromatin immunoprecipitation assays could be used to assess the binding of transcription factors at a regulatory DNA region of cell growth and/or survival gene(s).

The foregoing assay methods of the invention are amenable to high-throughput screening (HTS) implementations. In some embodiments, the screening assays of the invention are high throughput or ultra high throughput (e.g., Fernandes, P. B., Curr Opin Chem Biol. 1998 2:597; Sundberg, S A, Curr Opin Biotechnol. 2000, 11:47). HTS refers to testing of up to, and including, 100,000 compounds per day. Whereas ultra high throughput (uHTS) refers to screening in excess of 100,000 compounds per day. The screening assays of the invention may be carried out in a multi-well format, for example, a 96-well, 384-well format, or 1,536-well format, and are suitable for automation. In the high throughput assays of the invention, it is possible to screen several thousand different compounds or compositions in a single day. In particular, each well of a microtiter plate can be used to run a separate assay against a selected test compound, or, if concentration or incubation time effects are to be observed, a plurality of wells can contain test samples of a single compound. It is possible to assay many plates per day; assay screens for up to about 6,000, 20,000, 50,000, or more than 100,000 different compounds are possible using the assays of the invention. Typically, HTS implementations of the assays disclosed herein involve the use of automation. In some embodiments, an integrated robot system consisting of one or more robots transports assay microplates between multiple assay stations for compound, cell and/or reagent addition, mixing, incubation, and finally readout or detection. In some aspects, an HTS system of the invention may prepare, incubate, and analyze many plates simultaneously, further speeding the data-collection process. High throughput screening implementations are well known in the art. Exemplary methods are also disclosed in High Throughput Screening: Methods and Protocols (Methods in Molecular Biology) by William P. Janzen (2002) and High-Throughput Screening in Drug Discovery (Methods and Principles in Medicinal Chemistry) (2006) by Jörg Wiser, the contents of which are both incorporated herein by reference in their entirety.

As described above, compounds or compositions that substantially affect the growth and/or survival of a test cell and/or control cell, and/or that are candidate modulators ER function or UPR signaling can be discovered using the disclosed test methods. Examples of types of compounds or compositions that may be tested include, but are not limited to: anti-metastatic agents, cytotoxic agents, cytostatic agents, cytokine agents, anti-proliferative agents, immunotoxin agents, gene therapy agents, angiostatic agents, cell targeting agents, HDAC inhibitory agents, etc. As used herein, compounds or compositions may in some cases be referred to as test agents.

The following provides further examples of test compounds and is not meant to be limiting. Those of ordinary skill in the art will recognize that there are numerous additional types of suitable test compounds that may be tested using the methods, cells, and/or animal models of the invention. Test compounds can be small molecules (e.g., compounds that are members of a small molecule chemical library). The compounds can be small organic or inorganic molecules of molecular weight below about 3,000 Daltons. The small molecules can be, e.g., from at least about 100 Da to about 3,000 Da (e.g., between about 100 to about 3,000 Da, about 100 to about 2,500 Da, about 100 to about 2,000 Da, about 100 to about 1,750 Da, about 100 to about 1,500 Da, about 100 to about 1,250 Da, about 100 to about 1,000 Da, about 100 to about 750 Da, about 100 to about 500 Da, about 200 to about 1500, about 500 to about 1000, about 300 to about 1000 Da, or about 100 to about 250 Da).

The small molecules can be natural products, synthetic products, or members of a combinatorial chemistry library. A set of diverse molecules can be used to cover a variety of functions such as charge, aromaticity, hydrogen bonding, flexibility, size, length of side chain, hydrophobicity, and rigidity. Combinatorial techniques suitable for synthesizing small molecules are known in the art (e.g., as exemplified by Obrecht and Villalgrodo, *Solid-Supported Combinatorial and Parallel Synthesis of Small-Molecular-Weight Compound Libraries*, Pergamon-Elsevier Science Limited (1998)), and include those such as the "split and pool" or "parallel" synthesis techniques, solid-phase and solution-phase techniques, and encoding techniques (see, for example, Czarnik, A. W., *Curr. Opin. Chem. Biol.* (1997) 1:60). In addition, a number of small molecule libraries are publicly or commercially available (e.g., through Sigma-Aldrich, TimTec (Newark, Del.), Stanford School of Medicine High-Throughput Bioscience Center (HTBC), and ChemBridge Corporation (San Diego, Calif.).

Compound libraries screened using the new methods can comprise a variety of types of test compounds. A given library can comprise a set of structurally related or unrelated test compounds. In some embodiments, the test compounds are peptide or peptidomimetic molecules. In some embodiments, test compounds include, but are not limited to, peptide analogs including peptides comprising non-naturally occurring amino acids, phosphorous analogs of amino acids, amino acids having non-peptide linkages, or other small organic molecules. In some embodiments, the test compounds are peptidomimetics (e.g., peptoid oligomers, e.g., peptoid amide or ester analogues, D-peptides, L-peptides, oligourea or oligocarbamate); peptides (e.g., tripeptides, tetrapeptides, pentapeptides, hexapeptides, heptapeptides, octapeptides, nonapeptides, decapeptides, or larger, e.g., 20-mers or more); cyclic peptides; other non-natural peptide-like structures; and inorganic molecules (e.g., heterocyclic ring molecules). Test compounds can also be nucleic acids.

The test compounds and libraries thereof can be obtained by systematically altering the structure of a first "hit" compound, also referred to as a lead compound, that has a chemotherapeutic (e.g., anti-CSC) effect, and correlating that structure to a resulting biological activity (e.g., a structure-activity relationship study).

Such libraries can be obtained using any of the numerous approaches in combinatorial library methods known in the art, including: peptoid libraries (libraries of molecules having the functionalities of peptides, but with a novel, non-peptide backbone which are resistant to enzymatic degradation but which nevertheless remain bioactive; see, e.g., Zuckermann, et al., *J. Med. Chem.*, 37:2678-85 (1994)); spatially addressable parallel solid phase or solution phase libraries; synthetic library methods requiring deconvolution; the "one-bead on e-Compound" library method; and synthetic library methods using affinity chromatography selection (Lam, *Anticancer Drug Des.* 12:145 (1997)). Examples of methods for the synthesis of molecular libraries can be found in the art, for example in: DeWitt et al., *Proc. Natl. Acad. Sci. USA*, 90:6909 (1993); Erb et al., *Proc. Natl. Acad. Sci. USA*, 91:11422 (1994); Zuckermann et al., *J. Med. Chem.*, 37:2678 (1994); Cho et al., *Science*, 261:1303 (1993); Carrell et al., *Angew. Chem. Int. Ed. Engl.*, 33:2059 (1994); Carell et al., *Angew. Chem. Int. Ed. Engl.*, 33:2061 (1994); and in Gallop et al., *J. Med. Chem.*, 37:1233 (1994). Libraries of compounds can be presented in solution (e.g., Houghten (1992) *Biotechniques*, 13:412-421), or on beads (Lam (1991) *Nature*, 354: 82-84), chips (Fodor (1993) *Nature*, 364:555-556), bacteria (Ladner, U.S. Pat. No. 5,223,409), spores (Ladner, U.S. Pat. No. 5,223,409), plasmids (Cull et al. (1992) *Proc. Natl. Acad. Sci. USA*, 89:1865-1869) or on phage (Scott and Smith (1990) *Science*, 249:386-390; Devlin (1990) *Science*, 249:404-406; Cwirla et al. (1990) *Proc. Natl. Acad. Sci. USA*, 87:6378-6382; Felici (1991) *J. Mol. Biol.*, 222:301-310; Ladner, supra.).

In some embodiments, the methods of the invention are used to screen "approved drugs". An "approved drug" is any compound (which term includes biological molecules such as proteins and nucleic acids) which has been approved for use in humans by the FDA or a similar government agency in another country, for any purpose.

Applicants reserve the right to exclude any particular compound, compounds, or compound class from the scope of "test compound" and/or from the compositions and methods of the invention. In some embodiments the "test compound" is not a compound found in, or known in the art as an ingredient of, tissue culture medium, e.g., a compound provided for purposes of culturing the cells. In some embodiments the test compound may be one found in, or known in the art as an ingredient of, tissue culture medium, but is used as a test compound at concentrations differing from those at which it is typically used as an ingredient of tissue culture medium. In some embodiments the compound is not a compound known in the art as being useful for treating cancer and/or for reducing side effects associated with chemotherapy.

Certain results of the compound identification and characterization methods disclosed herein may be clinically beneficial, such as if the compound is a inducer of ER-stress such as those disclosed herein. Still other clinically beneficial results include: (a) inhibition or arrest of primary tumor growth, (b) inhibition of metastatic tumor growth and (c) extension of survival of a test subject. Compounds with clinically beneficial results are potential chemotherapeutics, and may be formulated as such.

Compounds identified as having a chemotherapeutic or anti-CSC effect are referred to herein as lead compounds and can be selected and systematically altered, e.g., using rational design, to optimize binding affinity, avidity, specificity, or other parameters. Such optimization can also be screened for using the methods described herein. Thus, one can screen a first library of small molecules using the methods described herein, identify one or more compounds that are "hits" or "leads" (by virtue of, for example, their ability to inhibit the growth and/or survival of a test cell and/or cancer stem cell and/or their ability to reduce the size and/or number of CSC dependent tumors, e.g., at the original site of implantation and at metastasis sites), and subject those hits to systematic structural alteration to create a second library of compounds (e.g., refined lead compounds) structurally related to the hit. The second library can then be screened using the methods described herein. A refined lead compound can be produced by modifying the lead compound to achieve (i) improved potency, (ii) decreased toxicity (improved therapeutic index); (iii) decreased side effects; (iv) modified onset of therapeutic action and/or duration of effect; and/or (v) modified pharmacokinetic parameters (absorption, distribution, metabolism and/or excretion). The lead compound could be, e.g., purified from natural sources or chemically synthesized. Modifications could be made directly to the lead compound, or refined lead compounds (e.g., derivatives) could be synthesized from suitable starting materials.

In certain embodiments of the invention a compound identified using the inventive methods displays selective activity (e.g., induction of ER stress, inhibition of proliferation, toxicity) against test cells relative to its activity against control cells. For example, the IC50 of a compound may be about 2, 5, 10, 20, 50, 100, 250, 500, or 1000-fold lower for test cells versus control cells. In some embodiments, the IC50 of a compound may be about 2, 5, 10, 20, 50, 100, 250, 500, or 1000-fold lower for cells that have undergone EMT than for genetically matched cells that have not undergone EMT. In some embodiments, the IC50 of a compound may be about 2, 5, 10, 20, 50, 100, 250, 500, or 1000-fold lower for CSCs than for non-CSC cancer cells. In some embodiments, the IC50 of a compound may be about 2, 5, 10, 20, 50, 100, 250, 500, or 1000-fold lower for CSCs than for normal (non-cancerous) cells that have not undergone EMT.

In some cases it is desirable to determine the potency of a compound of the invention using a dose response assay. Methods for determining the potency of compounds or compositions are well known in the art. In some embodiments, potency is characterized as a half maximal effective concentration (EC50) of a compound. As used herein, the term half maximal effective concentration (EC50) refers to the concentration of a compound that induces a response in a biological system (e.g., one or more cells) halfway between the baseline response (e.g., no compound) and the maximal response. EC50 is commonly used in the art as a measure of compound potency (e.g., drug potency). The EC50 of a dose response curve represents the concentration of a compound where 50% of its maximal effect (also referred to as maximal response) is observed. EC50 is related to the half maximal inhibitory concentration (IC50), which is often used as a measure of inhibition by a compound (50% inhibition) in a biochemical assays, for example competitive binding assays and functional agonist/antagonist assays. Methods for determining EC50/IC50 values are well known in the art.

A variety of techniques useful for determining the structures of compounds are known and can be used in the methods described herein (e.g., NMR, mass spectrometry, gas chromatography equipped with electron capture detectors, fluorescence, and absorption spectroscopy).

Assays of chemotherapeutic activity of test compounds may be conducted in vitro or ex vivo and/or in vivo using cells (e.g., test cells that have undergone an epithelial to mesenchymal transition, cancer stem cells identified or generated using any suitable method, cancer cells, cancer cell lines, etc.) and methods of the invention or any suitable system for testing efficacy. For example, a test compound may be administered to a nonhuman subject to which has been administered (e.g., implanted or injected with) a plurality of the test cells described herein, e.g., a number of cancer stem cells sufficient to induce the formation of one or more tumors (e.g., CSC-dependent tumors), a tumor xenograft, etc. The nonhuman subject can be, e.g., a rodent (e.g., a mouse). Optionally the nonhuman subject is immunocompromised, e.g., a Nude, SCID, NOD-SCID, Rag1−/−, and Rag2−/− mouse. In some embodiments the test subject is a cancer-prone animal, e.g., an animal model harboring an activated oncogene and/or lacking a tumor suppressor gene, or an animal that has been exposed to a condition, compound, or stimulus that renders the animal prone to develop cancer. As used herein, a non-human test subject may also be referred to as an animal host.

The test compound can be administered to the subject by any regimen known in the art. For example, the test compound can be administered prior to, concomitant with, and/or following the administration of cancer stem cells of the invention. A test compound can also be administered regularly throughout the course of the method, for example, one, two, three, four, or more times a day, weekly, bi-weekly, or monthly, beginning before or after cells of the invention have been administered. In other embodiments, the test compound is administered continuously to the subject (e.g., intravenously or by release from an implant, pump, sustained release formulation, etc.). The dose of the test compound to be administered can depend on multiple factors, including the type of compound, weight of the subject, frequency of administration, etc. Determination of dosages is routine for one of ordinary skill in the art. Typical dosages are 0.01-200 mg/kg (e.g., 0.1-20 or 1-10 mg/kg).

The size and/or number of tumors in the subject can be determined following administration of the tumor cells and the test compound. The size and/or number of tumors can be determined non-invasively by any means known in the art. For example, tumor cells that are fluorescently labeled (e.g., by expressing a fluorescent protein such as GFP) can be monitored by various tumor-imaging techniques or instruments, e.g., non-invasive fluorescence methods such as two-photon microscopy. The size of a tumor implanted subcutaneously can be monitored and measured underneath the skin.

To determine whether a compound affects ER-stress or the growth of cells, the size and/or number of tumors in the subject can be compared to a reference standard (e.g., a control value). A reference standard can be a control subject which has been given the same regimen of administration of cancer stem cells and test compound, except that the test compound is omitted or administered in an inactive form. Alternately, a compound believed to be inert in the system can be administered. A reference standard can also be a control subject which has been administered cancer cells that are not cancer stem cells and test compound, cancer cells that are not cancer stem cells and no test compound, or cancer cells that are not cancer stem cells and an inactive test compound. The reference standard can also be a numerical figure(s) or range of figures representing the level of a biomarker of ER-stress and/or the size and/or number of tumors expected in an untreated subject. This numerical figure(s) or range of figures can be determined by observation of a representative sample of untreated subjects. A reference standard may also be the test animal before administration of the compound.

In some cases the activity of a compound (e.g., a lead compound) can be tested by contacting control cells and test cells that are grown in a co-culture. Co-cultures enable evaluation of the selective growth and/or survival properties of two or more populations of cells (e.g., control and test cells) in contact with a compound in a common growth chamber. Typically, each population of cells grown a co-culture will have an identifying characteristic that is detectable and distinct from an identifying characteristic of the other population(s) of cells in the co-culture. In some embodiments, the identifying characteristic comprises a level of expression of GFP protein or other reporter protein such as those mentioned above and/or a biomarker of ER stress. However, the invention is not so limited and other identifying characteristics known in the art may be suitable, provided that the identifying characteristic enables measurement (e.g., by FACS or other suitable assay method disclosed herein) of a parameter of interest (e.g., ER stress, cell growth, cell survival) of each of the two or more populations of cells in the co-culture. Compositions, e.g., co-cultures, comprising at least some test cells (e.g., between 1 and 99% test cells) and at least some control cells (e.g., between 1 and 99% control cells), are an aspect of the invention. In some embodiments the percentage of test cells is between 10% and 90%. In other embodiments the percentage of test cells is between 20% and 80%. In some embodiments the percentage of test cells is between 30% and 70%. In some embodiments the percentage of test cells is between 40% and 60%, e.g., about 50%. In some embodiments the composition further comprises a test agent.

In other embodiments, test cells and control cells are maintained in separate vessels (e.g., separate wells of a microwell plate) under substantially identical conditions.

Assay systems comprising test cells, control cells, and one or more test compounds, e.g., 10, 100, 1000, 10,000, or more test compounds, wherein the cells and test agents are arranged in one or more vessels in a manner suitable for assessing effect of the test compound(s) on the cells, are aspects of the invention. Typically the vessels contain a suitable tissue culture medium, and the test compounds are present in the tissue culture medium. One of skill in the art can select a medium appropriate for culturing a particular cell type. In some embodiments, a medium is free or essentially free of serum or tissue extracts while in other embodiments such a component is present. In some embodiments, cells are cultured on a plastic or glass surface. In some embodiments cells are cultured on or in a material comprising collagen, laminin, Matrigel®, or a synthetic material, e.g., a synthetic hydrogel, intended to provide an environment that resembles in at least some respects the extracellular environment found in many tissues. In some embodiments test and/or control cells are cultured with non-cancerous stromal cells. In some embodiments test and/or control cells are cultured with fibroblasts. In some embodiments test and/or control cells are cultured in three-dimensional culture matrix.

Treatment of a Subject

Methods described herein have broad application to treating disorders, such as cancer, that are associated with cancer stem cells. Cancer is a disease characterized by uncontrolled or aberrantly controlled cell proliferation and other malignant cellular properties. As used herein, the term cancer includes, but is not limited to, the following types of cancer: breast cancer; biliary tract cancer; bladder cancer; brain cancer including glioblastomas and medulloblastomas; cervical cancer; choriocarcinoma; colon cancer; endometrial cancer; esophageal cancer; gastric cancer; hematological neoplasms including acute lymphocytic and myelogenous leukemia; T-cell acute lymphoblastic leukemia/lymphoma; hairy cell leukemia; chronic myelogenous leukemia, multiple myeloma; AIDS-associated leukemias and adult T-cell leukemia/lymphoma; intraepithelial neoplasms including Bowen's disease and Paget's disease; liver cancer; lung cancer; lymphomas including Hodgkin's disease and lymphocytic lymphomas; neuroblastomas; oral cancer including squamous cell carcinoma; ovarian cancer including those arising from epithelial cells, stromal cells, germ cells and mesenchymal cells; pancreatic cancer; prostate cancer; rectal cancer; sarcomas including leiomyosarcoma, rhabdomyosarcoma, liposarcoma, fibrosarcoma, and osteosarcoma; skin cancer including melanoma, Merkel cell carcinoma, Kaposi's sarcoma, basal cell carcinoma, and squamous cell cancer; testicular cancer including germinal tumors such as seminoma, non-seminoma (teratomas, choriocarcinomas), stromal tumors, and germ cell tumors; thyroid cancer including thyroid adenocarcinoma and medullar carcinoma; and renal cancer including adenocarcinoma and Wilms tumor. In preferred embodiments, cancer is a colon carcinoma, a pancreatic cancer, a breast cancer, an ovarian cancer, a prostate cancer, a squamous cell carcinoma, a cervical cancer, a lung carcinoma, a small cell lung carcinoma, a bladder carcinoma, a squamous cell carcinoma, a basal cell carcinoma, an adenocarcinoma, a sweat gland carcinoma, a sebaceous gland carcinoma, a papillary carcinoma, a papillary adenocarcinoma, a cystadenocarcinoma, a medullary carcinoma, a bronchogenic carcinoma, a renal cell carcinoma, a hepatocellular carcinoma, a bile duct carcinoma, a choriocarcinoma, a seminoma, a embryonal carcinoma, a Wilms' tumor, or a testicular tumor. In one embodiment, cancer is a lung carcinoma. In one embodiment, cancer is a breast carcinoma. Other appropriate cancers will be known to one of ordinary skill in the art.

Some aspects of the invention are methods for treating a subject having, or suspected of having, cancer comprising administering to the subject an effective amount of a compound that selectively targets cancer stem cells by inducing ER-stress In some embodiments, the treatment methods of the invention involve treatment of a subject having (e.g., harboring) or at risk of having a cancer stem cell (CSC) and/or a CSC-dependent tumor. In some embodiments, the subject has a tumor of epithelial origin (i.e., a carcinoma).

As used herein, a subject is a mammal, including but not limited to a dog, cat, horse, cow, pig, sheep, goat, chicken, rodent, or primate. Preferred subjects are human subjects. The human subject may be a pediatric or adult subject. In some embodiments the adult subject is a geriatric subject. Whether a subject is deemed "at risk" of having a tumor is a determination that may be within the discretion of the skilled practitioner caring for the subject. Any suitable diagnostic test and/or criteria can be used. For example, a subject may be considered "at risk" of having a tumor if (i) the subject has a mutation, genetic polymorphism, gene or protein expression profile, and/or presence of particular substances in the blood, associated with increased risk of developing or having cancer relative to other members of the general population not having mutation or genetic polymorphism; (ii) the subject has one or more risk factors such as having a family history of cancer, having been exposed to a carcinogen or tumor-promoting agent or condition, e.g., asbestos, tobacco smoke, aflatoxin, radiation, chronic infection/inflammation, etc., advanced age; (iii) the subject has one or more symptoms of cancer, etc. In some embodiments, if the compound is one that has been previously (i.e., prior to the instant invention) administered to subjects for purposes other than treating cancer, e.g., for treatment of a condition other than cancer, the subject is not one to whom the compound would normally be administered for such other purpose and/or the compound is administered in a formulation or at a dose distinct from that known in the art to be useful for such other purpose.

Moreover, as used herein treatment or treating includes amelioration, cure, and/or maintenance of a cure (i.e., the prevention or delay of relapse) of a disorder (e.g., a tumor). Treatment after a disorder has started aims to reduce, ameliorate or altogether eliminate the disorder, and/or its associated symptoms, to prevent it from becoming worse, to slow the rate of progression, or to prevent the disorder from re-occurring once it has been initially eliminated (i.e., to prevent a relapse). A suitable dose and therapeutic regimen may vary depending upon the specific compound used, the mode of delivery of the compound, and whether it is used alone or in combination.

As used herein, a therapeutically effective amount is an amount of a compound that inhibits tumor formation, progression, and/or spread (e.g., metastasis). In some embodiments, therapeutically effective amount is an amount of a compound sufficient to induce ER-stress in cell. A therapeutically effective amount can refer to any one or more of the compounds or compositions described herein, or discovered using the methods described herein, that have ER-stress inducing properties or that otherwise inhibit the growth and/or survival of cells, e.g., CSCs.

Methods for establishing a therapeutically effective amount for any compounds or compositions described herein will be known to one of ordinary skill in the art. As used herein, pharmacological compositions comprise compounds or compositions that have therapeutic utility, and a pharmaceutically acceptable carrier, e.g., that facilitate delivery of compounds or compositions, in a therapeutically effective amount. The effective amount for any particular application can also vary depending on such factors as the cancer being treated, the particular compound being administered, the size of the subject, or the severity of the disease or condition. One of ordinary skill in the art can empirically determine the effective amount of a particular molecule of the invention without necessitating undue experimentation. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned with the goal of avoiding substantial toxicity and yet effective to treat the particular subject. In some embodiments a useful compound increases the average length of survival, increases the average length of progression-free survival, and/or reduces the rate of recurrence, of subjects treated with the compound in a statistically significant manner.

Subject doses of the compounds described herein typically range from about 0.1 µg to 10,000 mg, more typically from about 1 µg to 8000 mg, e.g., from about 10 µg to 100 mg once or more per day, week, month, or other time interval. Stated in terms of subject body weight, typical dosages in certain embodiments of the invention range from about 0.1 µg to 20 mg/kg/day, e.g., from about 1 to 10 mg/kg/day, e.g., from about 1 to 5 mg/kg/day. The absolute amount will depend upon a variety of factors including the concurrent treatment, the number of doses and the individual patient parameters including age, physical condition, size and weight. These are factors well known to those of ordinary skill in the art and can be addressed with no more than routine experimentation. It is often the case that a maximum dose be used, that is, the highest safe dose according to sound medical judgment.

The dose used may be the maximal tolerated dose or a sub-therapeutic dose or any dose there between. Multiple doses of the molecules of the invention are also contemplated. When the molecules of the invention are administered in combination a sub-therapeutic dosage of either of the molecules, or a sub-therapeutic dosage of both, may be used in the treatment of a subject having, or at risk of developing, cancer. When the two classes of drugs are used together, the cancer medicament may be administered in a sub-therapeutic dose to produce a desirable therapeutic result. A "sub-therapeutic dose" as used herein refers to a dosage which is less than that dosage which would produce a therapeutic result in the subject if administered in the absence of the other agent. Thus, the sub-therapeutic dose of a cancer medicament is one which would not produce the desired therapeutic result in the subject in the absence of the administration of the molecules of the invention. Therapeutic doses of cancer medicaments are well known in the field of medicine for the treatment of cancer. These dosages have been extensively described in references such as Remington's Pharmaceutical Sciences, 18th ed., 1990; as well as many other medical references relied upon by the medical profession as guidance for the treatment of cancer.

The compositions disclosed herein may be administered by any suitable means such as orally, intranasally, subcutaneously, intramuscularly, intravenously, intra-arterially, parenterally, intraperitoneally, intrathecally, intratracheally, ocularly, sublingually, vaginally, rectally, dermally, or as an aerosol. Depending upon the type of condition (e.g., cancer) to be treated, compounds of the invention may, for example, be inhaled, ingested or administered by systemic routes. Thus, a variety of administration modes, or routes, are available. The particular mode selected will depend, of course, upon the particular compound selected, the particular condition being treated and the dosage required for therapeutic efficacy. The methods of this invention, generally speaking, may be practiced using any mode of administration that is medically acceptable, meaning any mode that produces acceptable levels of efficacy without causing clinically unacceptable adverse effects. Preferred modes of administration are parenteral and oral routes. The term "parenteral" includes subcutaneous, intravenous, intramuscular, intraperitoneal, and intrasternal injection, or infusion techniques. In some embodiments, inhaled medications are of particular use because of the direct delivery to the lung, for example in lung cancer patients. Several types of metered dose inhalers are regularly used for administration by inhalation. These types of devices include metered dose inhalers (MDI), breath-actuated MDI, dry powder inhaler (DPI), spacer/holding chambers in combination with MDI, and nebulizers. Other appropriate routes will be apparent to one of ordinary skill in the art.

According to the methods of the invention, the compounds may be administered in a pharmaceutical composition. Administering the pharmaceutical composition of the present invention may be accomplished by any means known to the skilled artisan. In addition to the active agent, the pharmaceutical compositions of the present invention typically comprise a pharmaceutically-acceptable carrier. The term "pharmaceutically-acceptable carrier", as used herein, means one or more compatible solid or liquid filler diluents or encapsulating substances which are suitable for administration to a human or lower animal. In preferred embodiments, a pharmaceutically-acceptable carrier is a non-toxic material that does not interfere with the effectiveness of the biological activity of the active ingredients. The term "compatible", as used herein, means that the components of the pharmaceutical compositions are capable of being comingled with the compound of the present invention, and with each other, in a manner such that there is no interaction which would substantially reduce the pharmaceutical efficacy of the pharmaceutical composition under ordinary use situations. Pharmaceutically-acceptable carriers must, of course, be of sufficiently high purity and sufficiently low toxicity to render them suitable for administration to the human or lower animal being treated.

Some examples of substances which can serve as pharmaceutically-acceptable carriers are sugars such as lactose, glucose and sucrose; starches such as corn starch and potato starch; cellulose and its derivatives, such as sodium carboxymethylcellulose, ethylcellulose, cellulose acetate; powdered tragacanth; malt; gelatin; talc; stearic acid; magnesium stearate; calcium sulfate; vegetable oils such as peanut oil, cottonseed oil, sesame oil, olive oil, corn oil and oil of theobrama; polyols such as propylene glycol, glycerin, sorbitol, mannitol, and polyethylene glycol; sugar; alginic acid; pyrogen-free water; isotonic saline; phosphate buffer solutions; cocoa butter (suppository base); emulsifiers, such as the Tweens®; as well as other non-toxic compatible substances used in pharmaceutical formulation. Wetting agents and lubricants such as sodium lauryl sulfate, as well as coloring agents, flavoring agents, excipients, tableting agents, stabilizers, antioxidants, and preservatives, can also be present.

The pharmaceutically-acceptable carrier employed in conjunction with the compounds of the present invention is used at a concentration sufficient to provide a practical size to dosage relationship. The pharmaceutically-acceptable carriers, in total, may comprise from about 60% to about 99.99999% by weight of the pharmaceutical compositions of the present invention, e.g., from about 80% to about 99.99%, e.g., from about 90% to about 99.95%, from about 95% to about 99.9%, or from about 98% to about 99%.

Pharmaceutically-acceptable carriers suitable for the preparation of unit dosage forms for oral administration and topical application are well-known in the art. Their selection will depend on secondary considerations like taste, cost, and/or shelf stability, which are not critical for the purposes of the subject invention, and can be made without difficulty by a person skilled in the art.

Pharmaceutically acceptable compositions can include diluents, fillers, salts, buffers, stabilizers, solubilizers and other materials which are well-known in the art. The choice of pharmaceutically-acceptable carrier to be used in conjunction with the compounds of the present invention is basically determined by the way the compound is to be administered. Exemplary pharmaceutically acceptable carriers for peptides in particular are described in U.S. Pat. No. 5,211,657. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts. It will also be understood that the compound can be provided as a pharmaceutically acceptable pro-drug, or an active metabolite can be used. Furthermore it will be appreciated that agents may be modified, e.g., with targeting moieties, moieties that increase their uptake, biological half-life (e.g., pegylation), etc.

The formulations of the invention are administered in pharmaceutically acceptable solutions, which may routinely contain pharmaceutically acceptable concentrations of salt, buffering agents, preservatives, compatible carriers, adjuvants, and optionally other therapeutic ingredients.

The compounds of the invention may be formulated into preparations in solid, semi-solid, liquid or gaseous forms such as tablets, capsules, powders, granules, ointments, solutions, depositories, inhalants and injections, and usual ways for oral, parenteral or surgical administration. The invention also embraces pharmaceutical compositions which are formulated for local administration, such as by implants.

Compositions suitable for oral administration may be presented as discrete units, such as capsules, tablets, lozenges, each containing a predetermined amount of the active agent. Other compositions include suspensions in aqueous liquids or non-aqueous liquids such as a syrup, elixir or an emulsion.

When the compounds described herein are used therapeutically, in certain embodiments a desirable route of administration may be by pulmonary aerosol. Techniques for preparing aerosol delivery systems containing compounds are well known to those of skill in the art. Generally, such systems should utilize components which will not significantly impair the biological properties of the peptides (see, for example, Sciarra and Cutie, "Aerosols," in Remington's Pharmaceutical Sciences, 18th edition, 1990, pp 1694-1712; incorporated by reference). Those of skill in the art can readily determine the various parameters and conditions for producing aerosols without resort to undue experimentation.

The compounds of the invention may be administered directly to a tissue. Preferably, the tissue is one in which the cancer cells are found. Alternatively, the tissue is one in which the cancer is likely to arise. Direct tissue administration may be achieved by direct injection. The peptides may be administered once, or alternatively they may be administered in a plurality of administrations. If administered multiple times, the peptides may be administered via different routes. For example, the first (or the first few) administrations may be made directly into the affected tissue while later administrations may be systemic.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl cellulose, sodium carboxymethylcellulose, and/or polyvinylpyrrolidone (PVP). If desired, disintegrating agents may be added, such as the cross linked polyvinyl pyrrolidone, agar, or alginic acid or a salt thereof such as sodium alginate. Optionally the oral formulations may also be formulated in saline or buffers for neutralizing internal acid conditions or may be administered without any carriers.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner. For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch. Techniques for preparing aerosol delivery systems are well known to those of skill in the art. Generally, such systems should utilize components which will not significantly impair the biological properties of the active agent (see, for example, Sciarra and Cutie, "Aerosols," in Remington's Pharmaceutical Sciences, 18th edition, 1990, pp 1694-1712; incorporated by reference). Those of skill in the art can readily determine the various parameters and conditions for producing aerosols without resort to undue experimentation.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like. Lower doses will result from other forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of compounds.

In yet other embodiments, the preferred vehicle is a biocompatible microparticle or implant that is suitable for implantation into the mammalian recipient. Exemplary bioerodible implants that are useful in accordance with this method are described in PCT International Application No. PCT/US/03307 (Publication No. WO 95/24929, entitled "Polymeric Gene Delivery System", claiming priority to U.S. patent application Ser. No. 213,668, filed Mar. 15, 1994). PCT/US/0307 describes a biocompatible, preferably biodegradable polymeric matrix for containing a biological macromolecule. The polymeric matrix may be used to achieve sustained release of the agent in a subject. In accordance with one aspect of the instant invention, the agent described herein may be encapsulated or dispersed within the biocompatible, preferably biodegradable polymeric matrix disclosed in PCT/US/03307. The polymeric matrix preferably is in the form of a microparticle such as a microsphere (wherein the agent is dispersed throughout a solid polymeric matrix) or a microcapsule (wherein the agent is stored in the core of a polymeric shell). Other forms of the polymeric matrix for containing the agent include films, coatings, gels, implants, and stents. The size and composition of the polymeric matrix device is selected to result in favorable release kinetics in the tissue into which the matrix device is implanted. The size of the polymeric matrix device further is selected according to the method of delivery which is to be used, typically injection into a tissue or administration of a suspension by aerosol into the nasal and/or pulmonary areas. The polymeric matrix composition can be selected to have both favorable degradation rates and also to be formed of a material which is bioadhesive, to further increase the effectiveness of transfer when the device is administered to a vascular, pulmonary, or other surface. The matrix composition also can be selected not to degrade, but rather, to release by diffusion over an extended period of time.

Both non-biodegradable and biodegradable polymeric matrices can be used to deliver the agents of the invention to the subject. Biodegradable matrices are preferred. Such polymers may be natural or synthetic polymers. Synthetic polymers are preferred. The polymer is selected based on the period of time over which release is desired, generally in the order of a few hours to a year or longer. Typically, release over a period ranging from between a few hours and three to twelve months is most desirable. The polymer optionally is in the form of a hydrogel that can absorb up to about 90% of its weight in water and further, optionally is cross-linked with multivalent ions or other polymers.

In general, the agents of the invention may be delivered using the bioerodible implant by way of diffusion, or more preferably, by degradation of the polymeric matrix. Exemplary synthetic polymers which can be used to form the biodegradable delivery system include: polyamides, polycarbonates, polyalkylenes, polyalkylene glycols, polyalkylene oxides, polyalkylene terepthalates, polyvinyl alcohols, polyvinyl ethers, polyvinyl esters, poly-vinyl halides, polyvinylpyrrolidone, polyglycolides, polysiloxanes, polyurethanes and co-polymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethyl methacrylate), poly (butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly(ethylene glycol), poly(ethylene oxide), poly(ethylene terephthalate), poly(vinyl alcohols), polyvinyl acetate, poly vinyl chloride, polystyrene and polyvinylpyrrolidone.

Examples of non-biodegradable polymers include ethylene vinyl acetate, poly(meth)acrylic acid, polyamides, copolymers and mixtures thereof.

Examples of biodegradable polymers include synthetic polymers such as polymers of lactic acid and glycolic acid, polyanhydrides, poly(ortho)esters, polyurethanes, poly(butic acid), poly(valeric acid), and poly(lactide-cocaprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

Bioadhesive polymers of particular interest include bio-erodible hydrogels described by H. S. Sawhney, C. P. Pathak and J. A. Hubell in Macromolecules, 1993, 26, 581-587, the teachings of which are incorporated herein, polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

Other delivery systems can include time-release, delayed release or sustained release delivery systems. Such systems can avoid repeated administrations of the peptide, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono- di- and tri-glycerides; hydrogel release systems; silastic systems; peptide based systems; wax coatings; compressed tablets using conventional binders and excipients; partially fused implants; and the like. Specific examples include, but are not limited to: (a) erosional systems in which the platelet reducing agent is contained in a form within a matrix such as those described in U.S. Pat. Nos. 4,452,775, 4,675,189, and 5,736,152 and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

Use of a long-term sustained release implant may be particularly suitable for prophylactic treatment of subjects at risk of developing a recurrent cancer. Long-term release, as used herein, means that the implant is constructed and arranged to deliver therapeutic levels of the active ingredient for at least 30 days, and preferably 60 days. Long-term sustained release implants are well-known to those of ordinary skill in the art and include some of the release systems described above.

EXAMPLES

Experimental Procedures

Cell Culture

HMLE and HMLER cells expressing shRNAs targeting GFP (shGFP), E-cadherin (shEcad) or coding sequence of Twist (Twist) were generated and maintained in a 1:1 mixture of DMEM+10% FBS, insulin, hydrocortisone, and MEGM. DsRed-expressing HMLE_shGFP and GFP-expressing HMLE_shEcad/HMLE_Twist cell strains were generated as described (Gupta et al., 2009). MCF7, T47D, BT474, ZR-75-30, Hs578T, MDA-MB-157, MDA-MB-231 cells (ATCC) were cultured in DMEM+10% FBS. BT549 and 4T1 cells (ATCC) were cultured in RPMI+10% FBS. SUM159 cells (Asterand) were cultured in F12+5% FBS, insulin, and hydrocortisone.

Mammosphere formation assays were performed as described (Dontu et al., 2003), but with 0.6% methylcellulose (Stem Cell Technologies). Five thousand cells were plated per well in low-adherence 24-well plates and cultured for 5-8 days prior to being counted and photographed.

shRNA Screen for Genetic-Chemical Interactions

For shRNA screens, a previously described (Luo et al., 2008) pool of 54,020 shRNAs targeting 11,194 human genes was utilized. The list of all shRNAs can be found at www-.broadinstitute.org/igp. The 54K pool of shRNAs, along with pCMV-dR8.2 dVPR and pCMV-VSVG, was transfected into 293T cells for viral packaging. An appropriate amount of lentivirus of the 54K pool was used to infect $3.6 \times 10^7$ HMLE_Twist cells to achieve an MOI of 0.3 (Luo et al., 2008). The infected cells were selected with puromycin. Three days after puromycin selection, half of the cells were treated with 4.5 μM Cmp302 for 14 days, while the other half was cultured in DMSO containing media for the same period of time. At this dose, cell numbers were depleted versus untreated control cell by more than 95% at the end of treatment. Final harvests of the infected cell in both groups were used for the subsequent analysis.

Purification of Genomic DNA

Harvested cells were resuspended in PBS and lysed according to the QIAamp Blood Maxi Kit protocol (Qiagen). The purified genomic DNA was eluded in 100 μl of TE buffer.

Amplification and Illumina Sequencing for Hairpin Region within Genomic DNA

The hairpin region of purified genomic DNA was amplified by PCR containing (per 100 μl reaction mix) 1 μM 5' primer (5'-AAT GAT ACG GCG ACC ACC GAG AAA GTA TTT CGA TTT CTT GGC TTT ATA TAT CTT GTG GAA CTG ACG A-3'; SEQ ID NO:1), 1 μM 3' primer (5'-CAA GCA GAA GAC GGC ATA CGA GCT CTT CCG ATC TTG TGG ATG AAT ACT GCC ATT TGT CTC GAG GTC-3'; SEQ ID NO:2), 6 μg genomic DNA, 5 μl DMSO and appropriate amount of reaction buffer, dNTPs and Taq. Thermal cycler PCR conditions consisted of heating samples to 95° C. for 5 min; 25 cycles of 94° C. for 30 sec, 58° C. for 30 sec, and 72° C. for 1 min; and 72° C. for 10 min. The PCR product was purified and sent for Illumina sequencing using a sequencing primer (5'-GAG AAA GTA TTT CGA TTT CTT GGC TTT ATA TAT CTT GTG GA-3'; SEQ ID NO:3)

Detection of ER Exit Sites (ERES)

HMLE and HMLE_shEcad cells ($2 \times 10^5$/well of a 6-well plate) were transfected with 1 μg pmGFP-Sec16S (Addgene plasmid 15775, Dr. Benjamin Glick) using 2.5 μl of Fugene (Roche). The next day, cells were re-plated and allowed to adhere onto cover slides prior to confocal imaging, which was performed in accordance with the manufacturer's protocols (Perkin Elmer).

Animal Experiments

NOD/SCID mice were purchased from Jackson Labs. All mouse procedures were approved by the Animal Care and Use Committees of the Massachusetts Institute of Technology. For drug pretreatment experiments, SUM159 cells were treated for 3 days and allowed to recover in the absence of drug for 4 days prior to in vivo injection, $1\times10^6$ SUM159 cells were resuspended in 100 µl PBS and injected into the tail-veins of mice. Lung tissues from experimental animals were harvested 4 and 48 hours post-injection.

Dose-Response Assays with Chemical Compounds

Cells (3000/well) were plated in 100 µl per well in 96-well plates. One day (24 hr) after seeding, compounds were added in 8 different doses at three replicates per dose for each cell line. Cell viability was measured after 72 hr with the CellTiter-Glo AQueous Non-radioactive Assay (Promega). Paclitaxel, Doxorubicin, Tunicamycin, Thapsigargin, A23187 and DTT were purchased from Sigma Aldrich. Cmp302 and Cmp308 were purchased from Biointerscreen.

In Vitro Wound-Healing Assay $7.5\times10^5$ cells were seeded on 3.5 cm plates 18 hours before wounding. Cells were washed two times with PBS, refed with culture medium and allowed to migrate for 7 hours before visualization.

Western Blot

Western blotting was performed as previously described (Gupta et al., 2009). Antibodies used for immunoblotting were as follows: E-cadherin (BD Transduction), Fibronectin (Abcam), Actin, Cytokeratin 8/18, PERK, eIF2α, peIF2α, CHOP, Caspase-3 and Bip (Cell Signal Technology).

Immunohistochemistry

Immunohistochemistry procedures were performed as previously described (Gupta et al., 2009). Anti-GFP antibody was from Cell Signal Technology.

Fluorescence-Activated Cell Sorting (FACS)

FACS analysis was performed according to the manufacturer's protocol (BD Biosciences). Reagents used in FACS were as follows: APC-conjugated anti-CD44 antibody (clone G44-26), PE-conjugated anti-CD24 antibody (clone ML5), and propidium iodide (5 µg/ml) (BD Bioscience).

ATF6 Reporter Assay p5xATF6-GL3 and hRluc constructs were obtained from Addgene (plasmids 11976 and 24348, provided by Drs. Ron Prywes and Liqun Luo, resp.). 24 hours after co-transfection of 0.3 µg p5xATF6-GL3 and 0.05 µg hRluc plasmids, cells were treated with indicated compounds for another 6 hours, and ATF6 activity was measured by a dual luciferase assay (Promega).

$^{35}$S-Methionine/Cysteine Protein Labeling

Equal numbers of cells were cultured in the presence of $^{35}$S-methionine/cysteine in medium with reduced methionine/cysteine content and minimal serum. At the indicated timepoints, aliquots of medium were extracted for analysis. Medium was centrifuged at 800×g for 2 min to pellet any whole cell contaminants. Equal volume of medium was reduced in loading buffer, separated by SDS-PAGE and analyzed by autoradiography.

Identification of Major Secreted Proteins 10 million HMLE_shGFP and HMLE_shEcad cells were seeded in serum-free medium, and culture medium was collected at 48 hours. Protein from the culture medium was concentrated, separated by SDS-PAGE and silver-stained. Proteins in specific fractions of the gel were analyzed by mass-spectrometry.

Example 1

Characterization of Small Molecules with Selective Toxicity Towards IDMS Cells

Figure 1B:
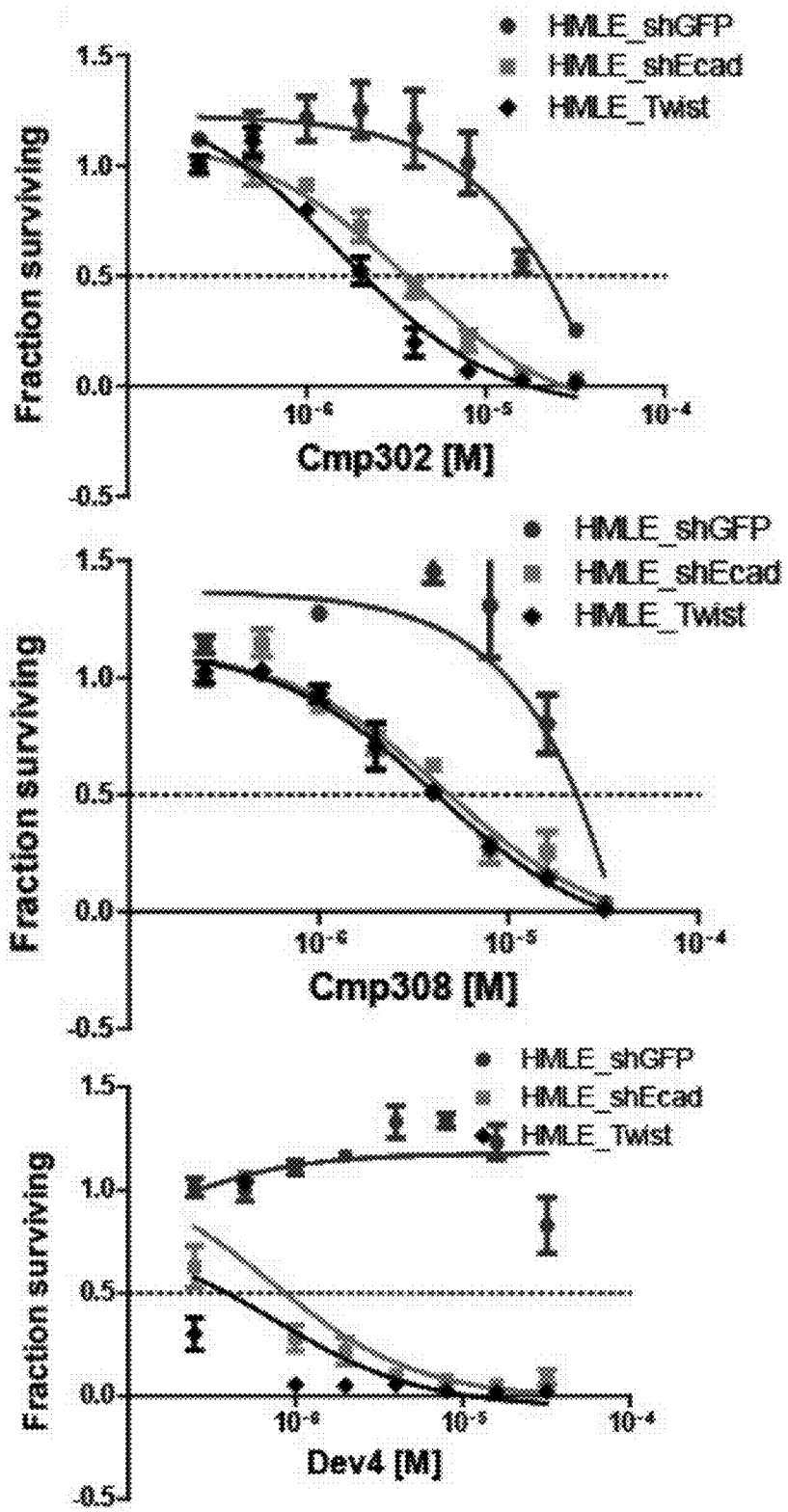
Figure 1C:
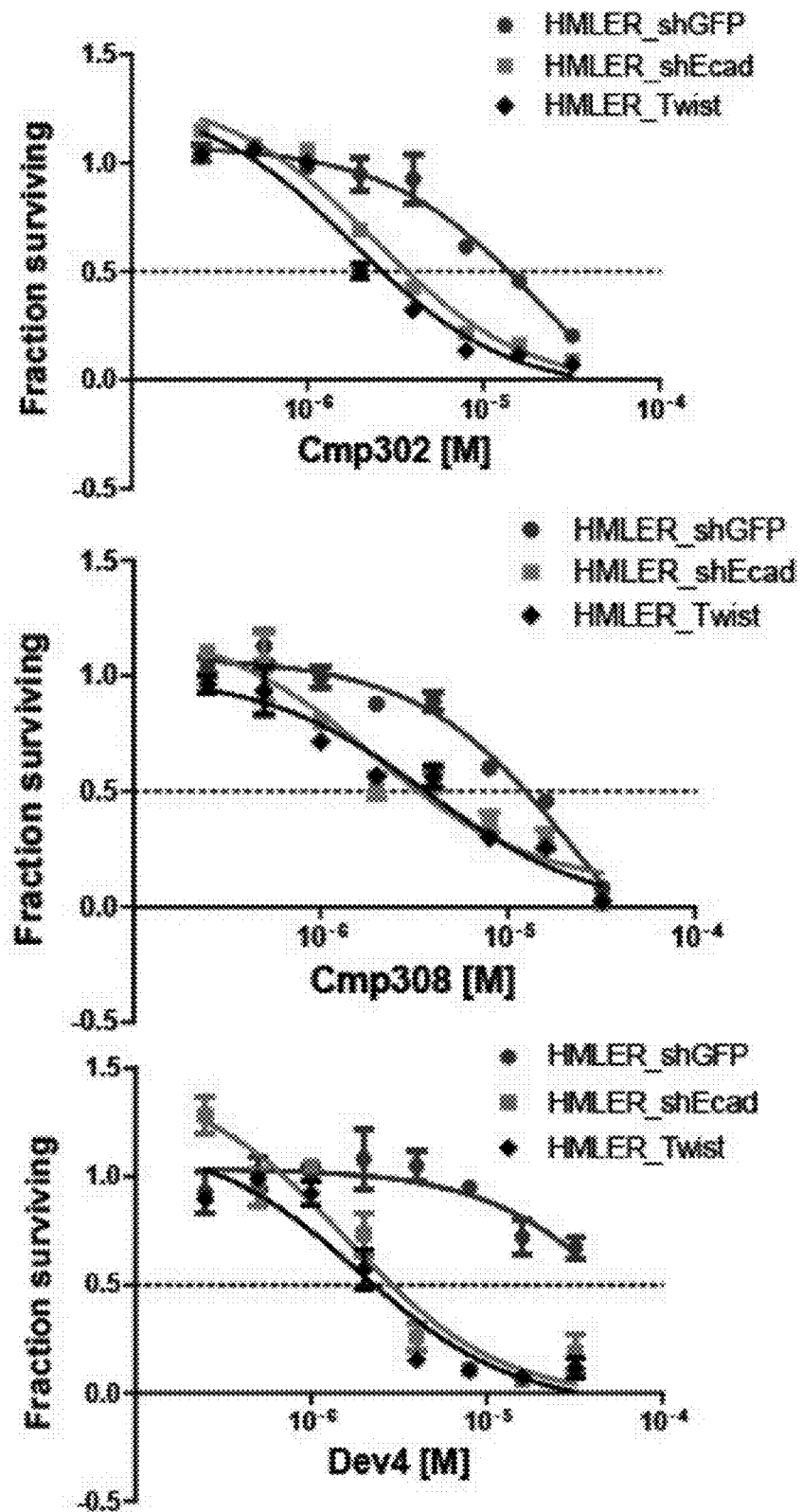

A recent report described two structurally similar compounds, Cmp302 and Cmp308, that exhibit 20-fold selective toxicity towards invasive, drug-resistant, mesenchymal, stem-like cells (hereafter IDMS, to emphasize these various phenotypic traits) (FIG. 1A, 1B) (Germain et al., 2012). These compounds displayed selective toxicity towards immortalized human mammary epithelial cells (HMLE) induced through EMT either by inhibition of E-cadherin (shEcad) or overexpression of Twist, indicating that their selective toxicity did not depend on the means of EMT induction (FIG. 1B). The selectivity of these compounds was retained when HMLE epithelial cells were transformed by an oncogenic RasV12 allele (FIG. 1C).

Figure 1D:
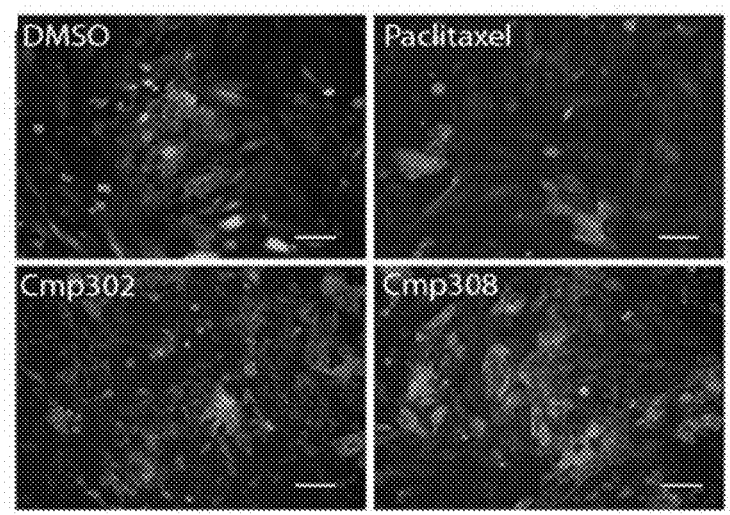
Figure 1E:
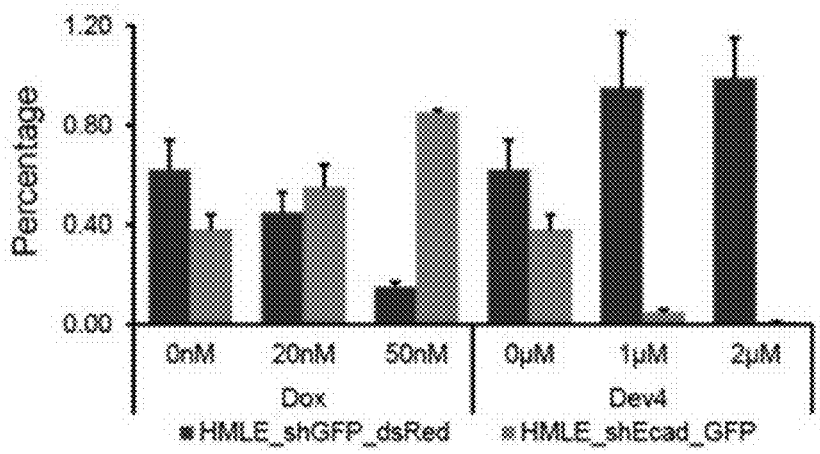

Even though Cmp302 and Cmp308 were selective for IDMS cells when cultured alone, tumors are comprised of heterogeneous populations of cells that could affect the sensitivity or selectivity of the applied chemicals. Therefore GFP-labeled IDMS cells were co-cultured with dsRed-labeled control epithelial cells and then applied Cmp302 and Cmp308. Treatment with Cmp302 or Cmp308 selectively depleted IDMS cells from the mixed populations; in contrast, treatment with paclitaxel or doxorubicin led to a selective expansion of IDMS cells (FIGS. 1D and E). These results exclude the possibility that Cmp302 and Cmp308 were more stable in IDMS-conditioned medium, which would have skewed toxicity towards the IDMS cells.

Modifications in the benzene ring of Cmp302 modulated selective potency, whereas modifications in its pyrrolidine group abrogated overall potency (Germain et al., 2012). These analyses led to the development of compound Dev4, with greater potency and selective toxicity (>100-fold) towards IDMS cells (Dev4; FIG. 1A-E). In contrast, the single substitution in the pyrrolidine group in Dev2 completely abrogated activity (FIG. 8A-B).

Figure 1F:
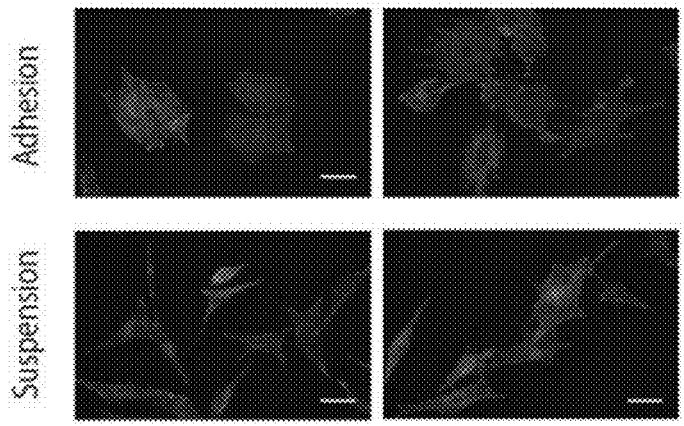
Figure 1G:
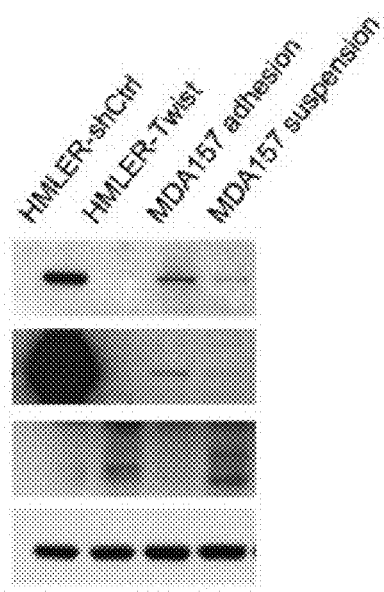
Figure 1H:
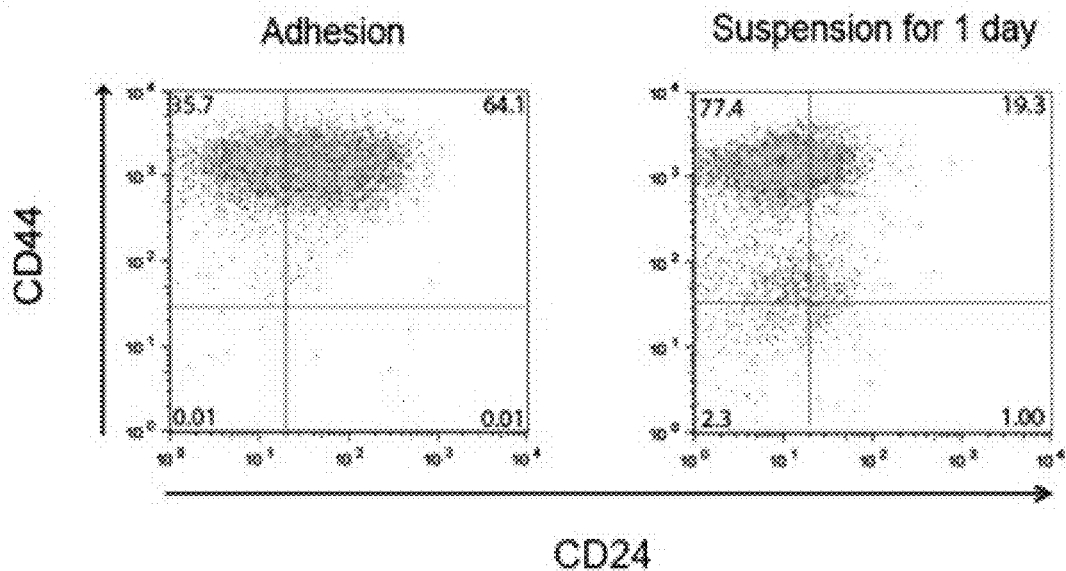

Next, it was determined whether the preferential toxicity of these compounds was unique to the oncogenic modifications of the HMLE breast epithelial cell system. Accordingly, a model was developed in which human breast carcinoma cells progressed towards the IDMS state in the absence of genetic modifications by altering their extracellular contextual signals. The MDA-MB-157 line was established from a medullary breast carcinoma and displays typical epithelial characteristics when grown adherently. However, this line adopts an IDMS state when detached from its substratum and cultured in suspension (FIG. 1F). MDA-MB-157 cells grown in suspension exhibited a morphology consistent with mesenchymal transdifferentiation, maintained for at least 24 hours when cells were allowed to re-adhere in 2D culture (FIG. 1F). This morphologic alteration was accompanied by upregulation of mesenchymal markers (fibronectin) and downregulation of epithelial proteins (cytokeratin 8/18 and E-cadherin) (FIG. 1G). Furthermore, cells grown in suspension acquired a breast CSC CD44$^{hi}$/CD24$^{lo}$ immunophenotype (FIG. 1H).

Figure 1I:
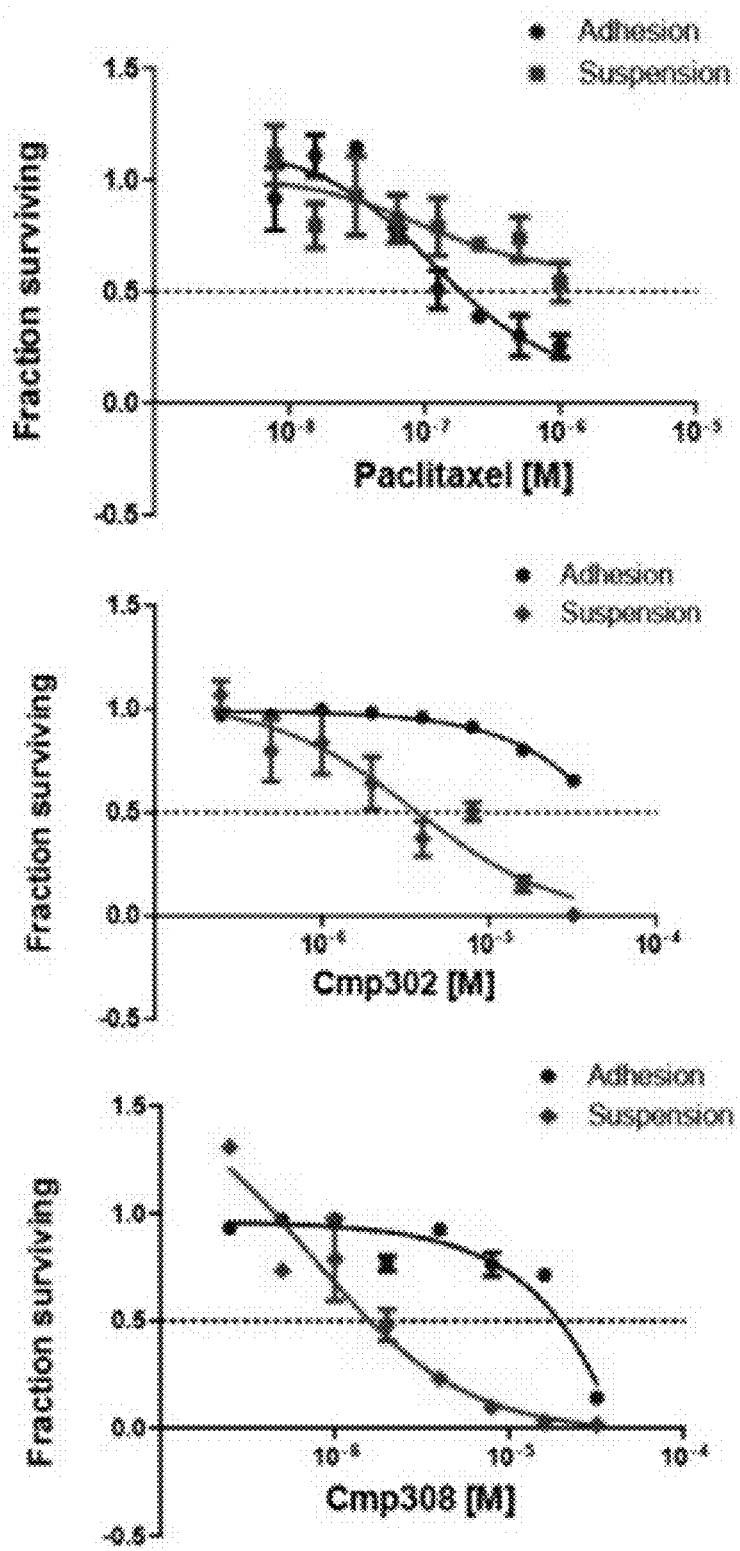
Figure 1J:
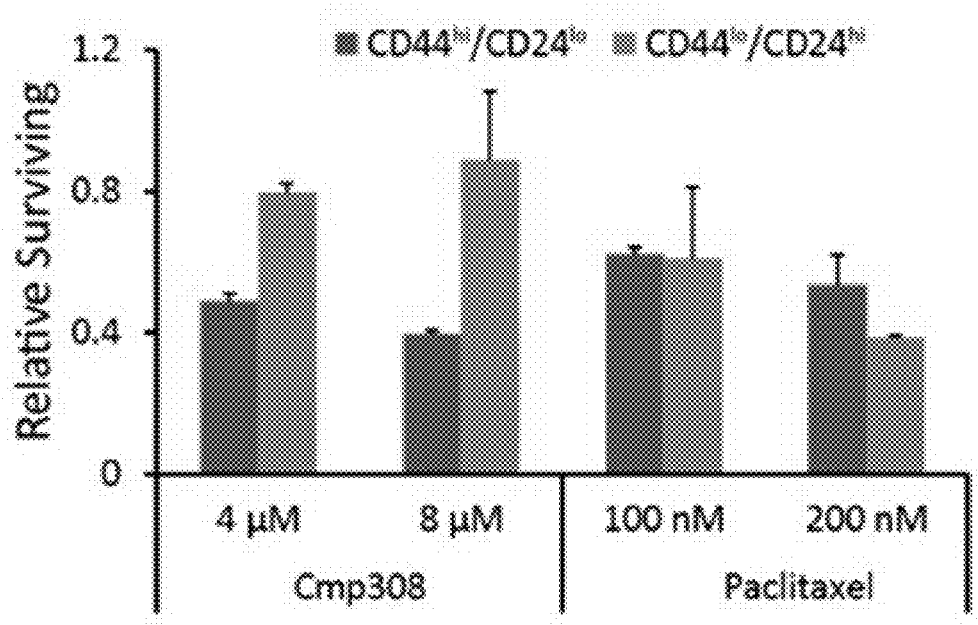

Consistent with the observations with IDMS cells in the context of the HMLE model, IDMS MDA-MB-157 cells were also more sensitive to the lethal effects of Cmp302 and Cmp308, relative to non-IDMS MDA-MB-157 cells grown in adherent conditions (20-fold and 10-fold more sensitive, respectively; FIG. 1I, 1J). In contrast, the chemotherapy drug paclitaxel displayed decreased toxicity towards IDMS MDA-MB-157 cells in suspension, relative to non-IDMS cells in adherent conditions (FIG. 1I). Moreover, Cmp302 treatment was mostly toxic towards the $CD44^{hi}CD24^{lo}$ fraction, with minimal impact on the $CD44^{lo}CD24^{hi}$ fraction; in contrast, paclitaxel treatment did not exhibit this preferential toxicity (FIG. 1J).

Thus Cmp302, Cmp308 and Dev4 display selective toxicity towards IDMS cells, unlike established chemotherapy drugs, which do not display this selective toxicity.

Example 2

Figure 2A:
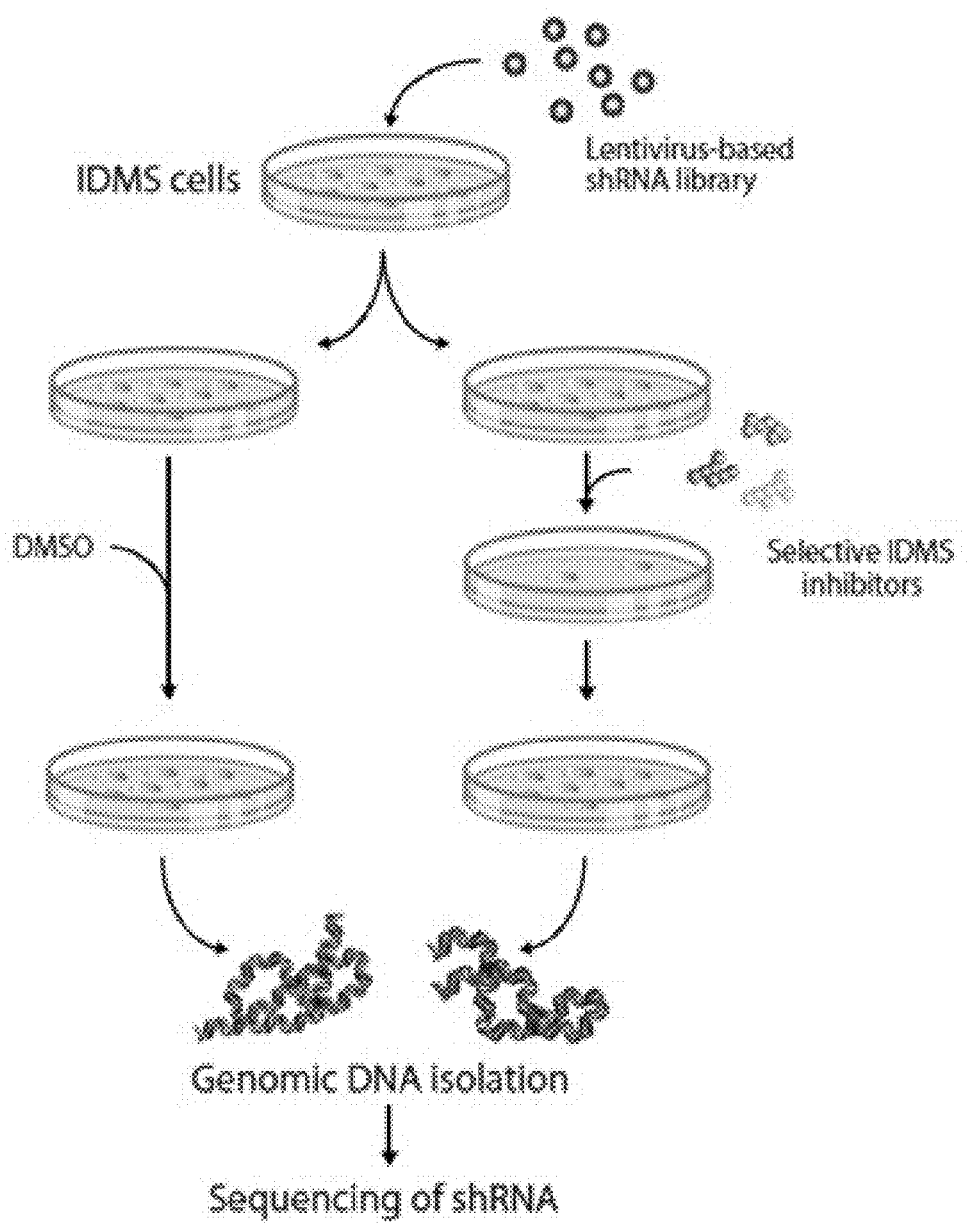

Genome-Wide shRNA Screen to Identify Genetic Interactions with Compound Treatment To identify the mechanism by which the selective small-molecules exert their toxicity towards IDMS cells, a genome-scale shRNA screen was performed to identify genetic interactions with Cmp302 treatment (FIG. 2A). For this experiment, IDMS breast epithelial cells (HMLE_Twist) first were stably transduced with a complex mixture of ~55,000 shRNAs; these infections were performed at a low multiplicity of infection to ensure that the vast majority of cells expressed a single shRNA. After expansion in culture, the shRNA-transduced cells were treated with either Cmp302 at its $IC_{95}$ dose or with a vehicle control. Following chemical treatment, genomic DNA was isolated from the surviving cells and used PCR, followed by next-generation sequencing, to quantify the relative numbers of surviving cells with each introduced shRNA.

Figure 2B:
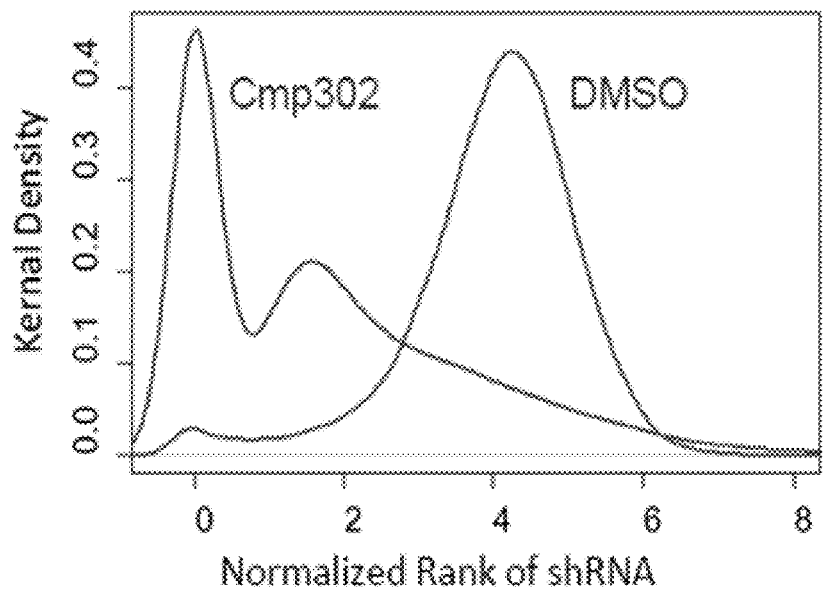
Figure 2C:
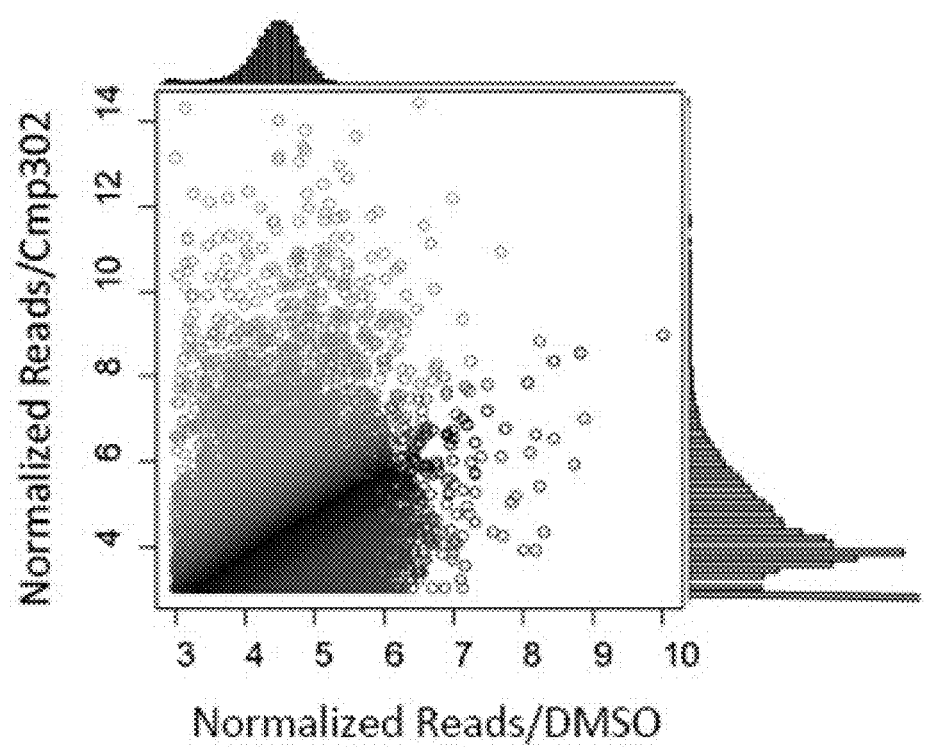
Figure 2D:
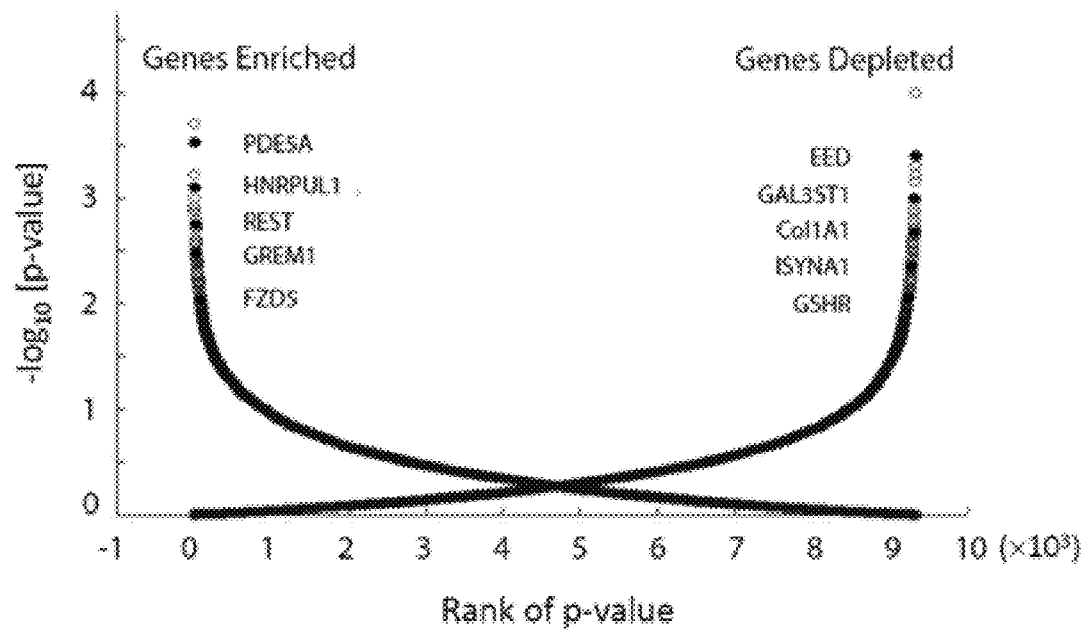

The analysis of the quantitative screen data was divided into three steps. First, the relative representation of each shRNA in the Cmp302- and DMSO-treated conditions was compared (FIG. 2B, C). This indicated that Cmp302 treatment led to a loss of many shRNAs from the infected population, consistent with the significant cell death that occurred at its applied dose (FIG. 2B). Second, each shRNA was ranked based on its degree of enrichment or depletion in the Cmp302 vs. vehicle treatment conditions and applied RNAi gene enrichment ranking analysis to compute gene-level scores (FIG. 2D). Third, gene set enrichment analysis (GSEA) was performed to identify sets of genes whose expression levels modulated cellular sensitivity to compound treatment (FIG. 2E, 2F).

These analyses identified gene sets whose expression correlated positively or negatively with survival in the presence of Cmp302 (FIG. 2E, 2F). Analysis of 790 annotated Gene Ontology (GO) gene sets revealed that shRNA-mediated inhibition of 13 gene sets conferred resistance to Cmp302 at a $p<0.05$ significance threshold (FIG. 2E). Genes that encode extracellular matrix (ECM) components were significantly overrepresented among these 13 gene sets (blue, FIG. 2D; $p<8.8\times10^{-6}$, hypergeometric test), indicating that shRNAs which target ECM genes were significantly overrepresented in the Cmp302 treatment condition.

Conversely, shRNA-mediated inhibition of 33 gene sets ($p<0.05$) increased sensitivity to Cmp302 treatment (FIG. 2F). These gene sets segregated into two major functional categories: regulation of cellular proliferation and ER physiology (red, blue resp., FIG. 2F). Notably, many aspects of ER function were represented at a statistically significant level, including gene sets related to lipid biosynthesis, vesicular localization and transport, and protein glycosylation ($p<10^{-10}$, hypergeometric test).

Example 3

IDMS Cells are Sensitized to ER Stress

The shRNA screen results described in Example 2 indicated that reducing ER load by knockdown of secreted proteins in IDMS cells leads to Cmp302 resistance. Conversely, compromising ER function by disruption of vesicular transport, lipid synthesis or protein glycosylation further sensitized cells to Cmp302-induced death. Based on these findings, it was hypothesized that Cmp302 could be causing cell death by compromising ER function.

Figure 3A:
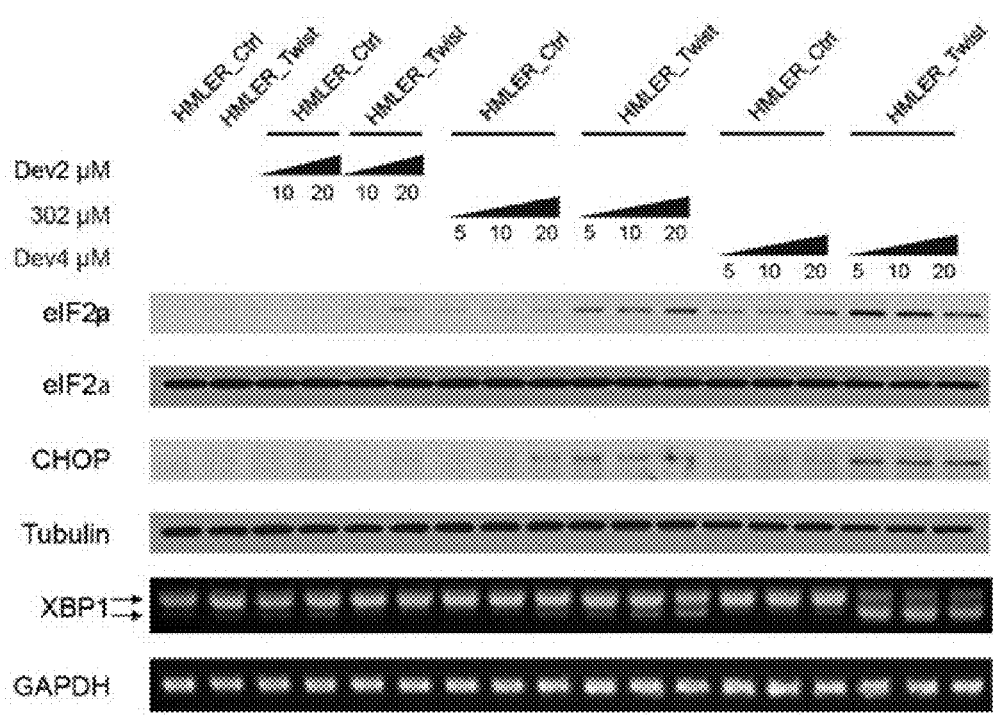

Cmp302 treatment triggered a dosage-dependent increase in UPR signaling, including increased XBP1 splicing, eIF2α phosphorylation and ATF6 activation (FIG. 3A and FIG. 8A). Additionally, there was a strong induction of downstream UPR factors including CHOP and Bip (FIG. 3A, FIG. 8B). These ER stress-associated signaling alterations occurred at a lower dose in IDMS carcinoma cells when compared to non-IDMS cells (FIG. 3A).

Dev4 is a derivative of Cmp302 optimized for potency and selective toxicity. Dev4 selectively induced the UPR in IDMS cells; it did so at lower doses than Cmp302 (FIG. 3A and FIGS. 8A, 8B and 8E). Treatment with the non-toxic derivative, Dev2, failed to evoke a UPR (FIG. 3A). The relative toxicities of Cmp302, Dev4 and Dev2 towards IDMS cells were thus directly correlated with the extent to which these compounds induced the UPR.

The facile induction of cell death and UPR pathways in IDMS could be a consequence either of a unique interaction between Cmp302/Dev4 treatment and the IDMS state, or might result from a generalized sensitivity of IDMS cells to ER stress. To distinguish between these possibilities, an assessment was performed of whether IDMS cancer cells were also selectively sensitive to four established chemical inducers of the UPR: thapsigargin, tunicamycin, dithiothreitol (DTT), and A23187.

Figure 3B:
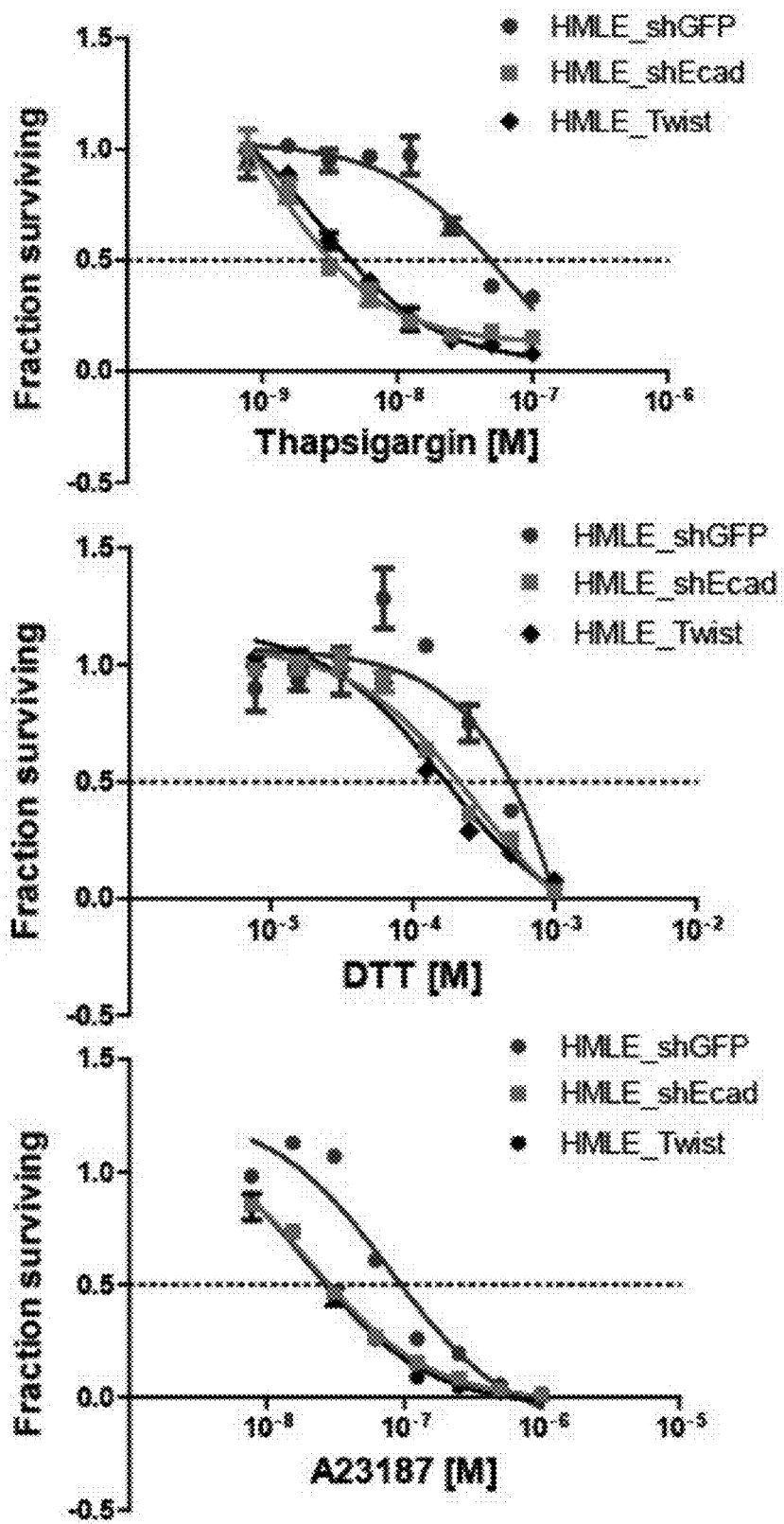
Figure 3C:
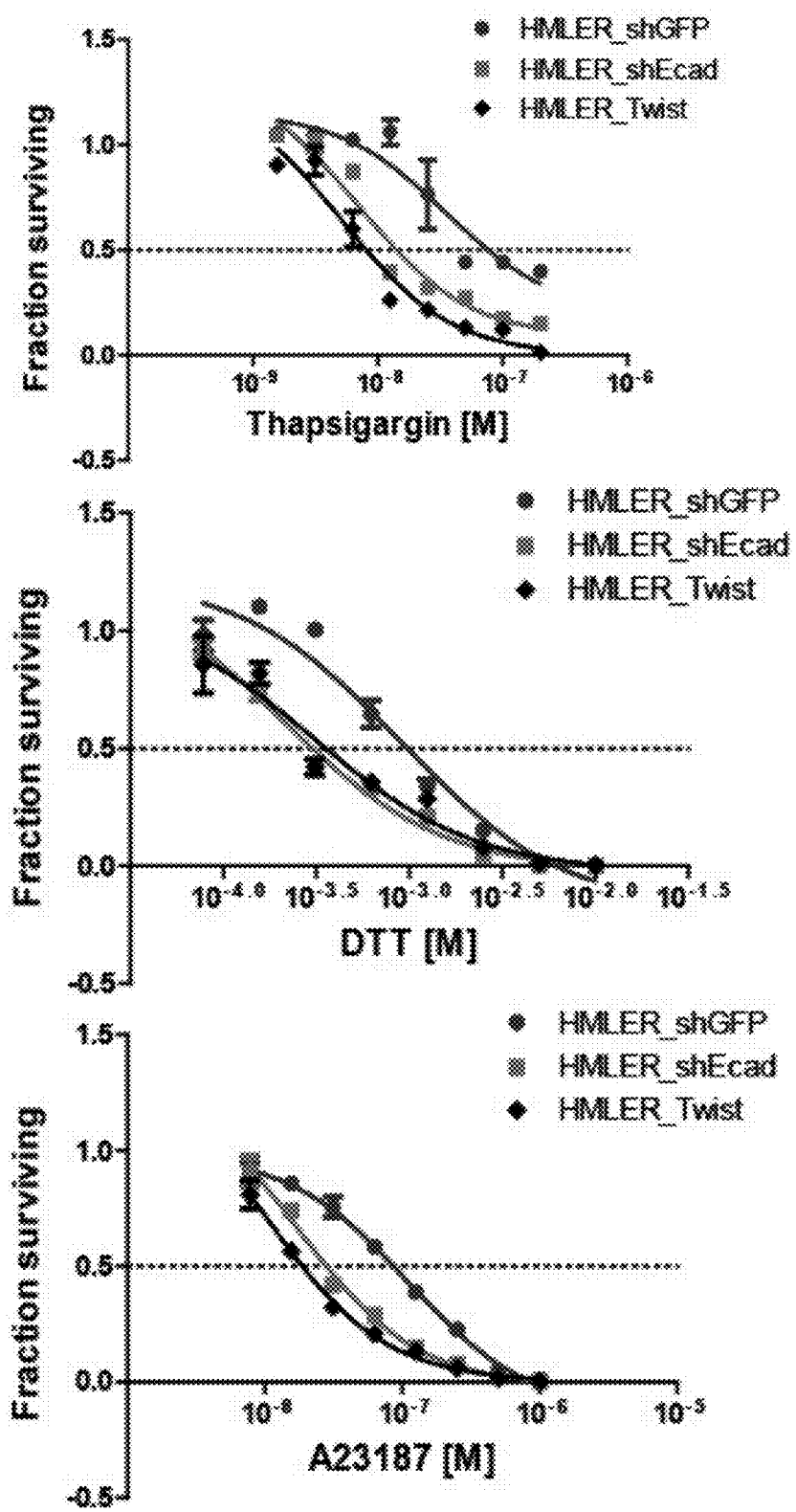
Figure 3D:
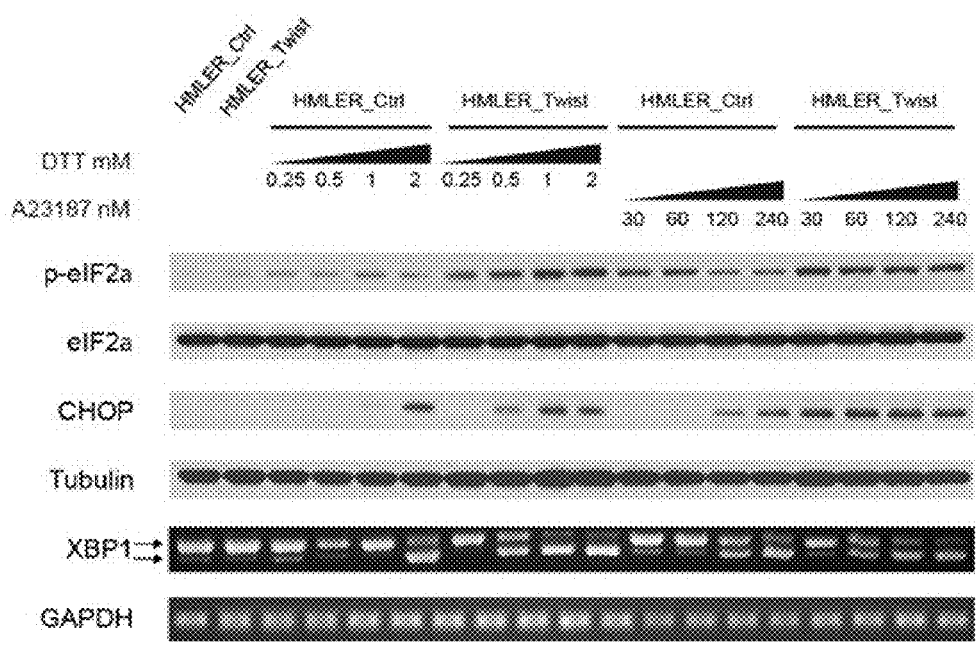
Figure 3E:
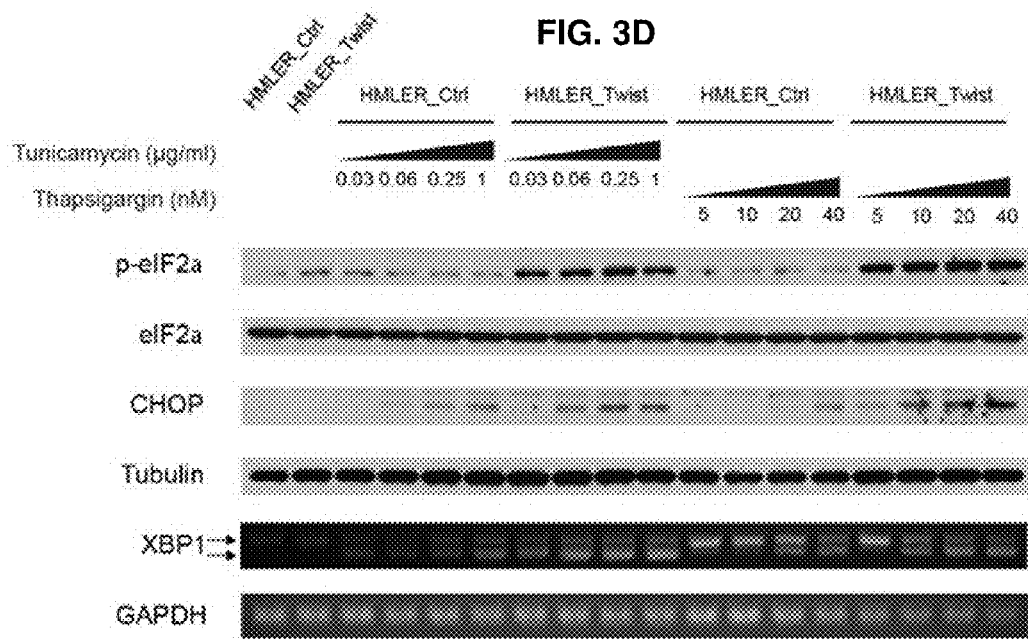

Three out of four of these UPR-inducing compounds were significantly more effective in killing IDMS cells relative to control HMLE cells (FIG. 3B, 3C). Tunicamycin exhibited strong toxicity against both IDMS and control HMLE cells even at very low doses ($IC50<10^{-10}$ g/ml), precluding an effective assessment of its relative toxicity (data not shown).

The selective lethality of DTT, A23187 and thapsigargin towards IDMS cells and correlation with a selective induction of the UPR was next examined. When applied at a range of doses bracketing their respective IC50s, treatment with these compounds selectively induced eIF2α phosphorylation, XBP1 splicing and ATF6 activation, as well as the expression of CHOP, GADD34 and Bip in IDMS cells relative to controls (FIG. 3D, 3E and FIGS. 8C, 8D and 8E). The preferential induction of UPR signaling in IDMS cells was accompanied by selective cleavage of caspase-3, consistent with ER-stress associated apoptosis (FIG. 8F). UPR signaling was also more readily induced in IDMS cells by tunicamycin (FIG. 3E), but required a dose 100-fold higher than its toxic dose, indicating that its toxicity was occurring via a different mechanism. Thus, the selective toxicity of DTT, A23187, thapsigargin and tunicamycin correlated with their ability to selectively induce UPR signaling in IDMS cells.

Collectively, these findings demonstrate that IDMS cells are sensitized to death in response to chemical perturbants that induce ER stress. Moreover, the increased sensitivity of IDMS cells was not a consequence of their tumorigenicity per se, but rather was attributable to their state of differentiation.

Example 4

IDMS Cells are Highly Secretory

To identify the molecular factors that underlie the heightened sensitivity of IDMS cells to chemical inducers of ER stress, global transcriptional profiles of immortalized IDMS cells were compared with their corresponding controls. For these studies, five distinct genetic perturbations were applied to induce the IDMS state: a shRNA targeting E-cadherin, stimulation with TGF-beta ligand, or overexpression of one of three transcription factors—Twist, Snail or Goosecoid (Taube et al., 2010). These data were analyzed by scoring the enrichment of 956 sets of functionally annotated genes in the IDMS epithelial cells relative to the control cells (Subramanian et al., 2005).

Figure 4A:
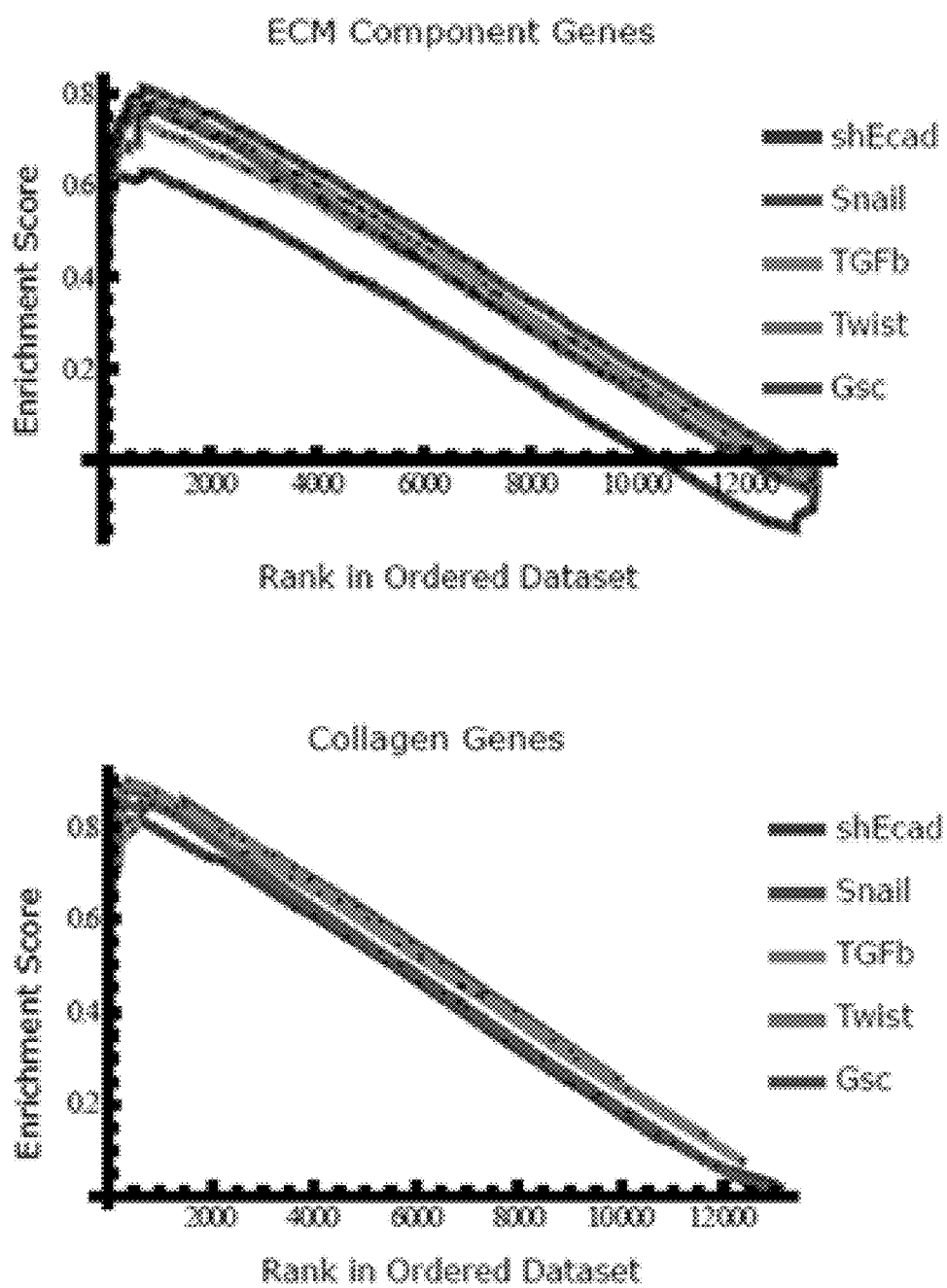
Figure 4B:
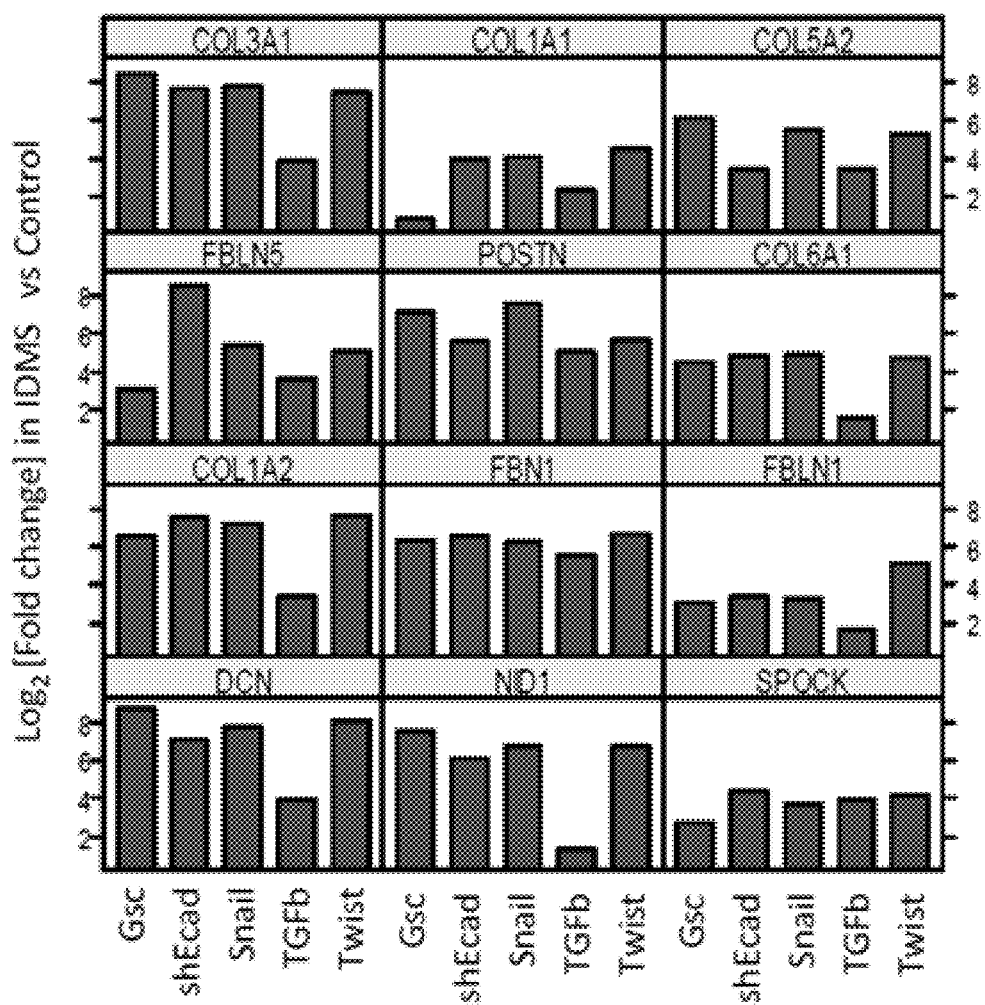
Figure 4C:
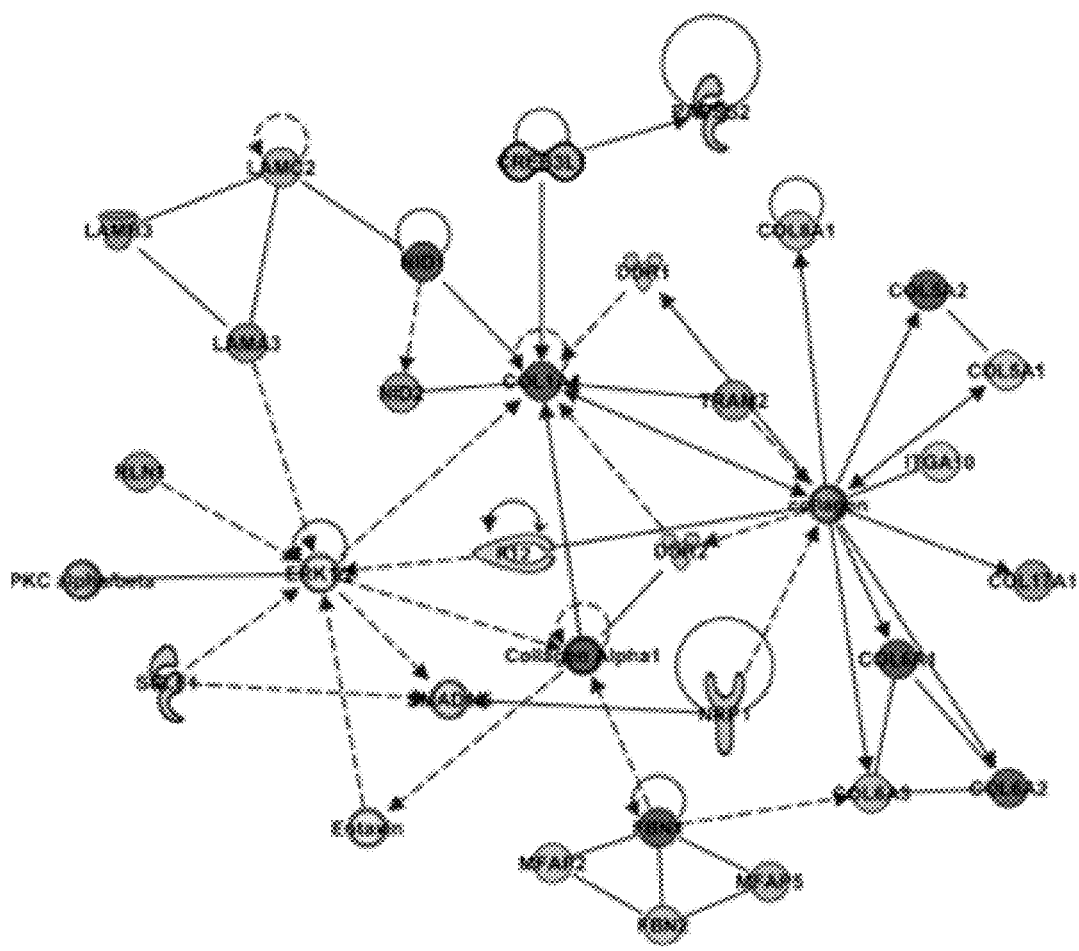
Figure 4D:
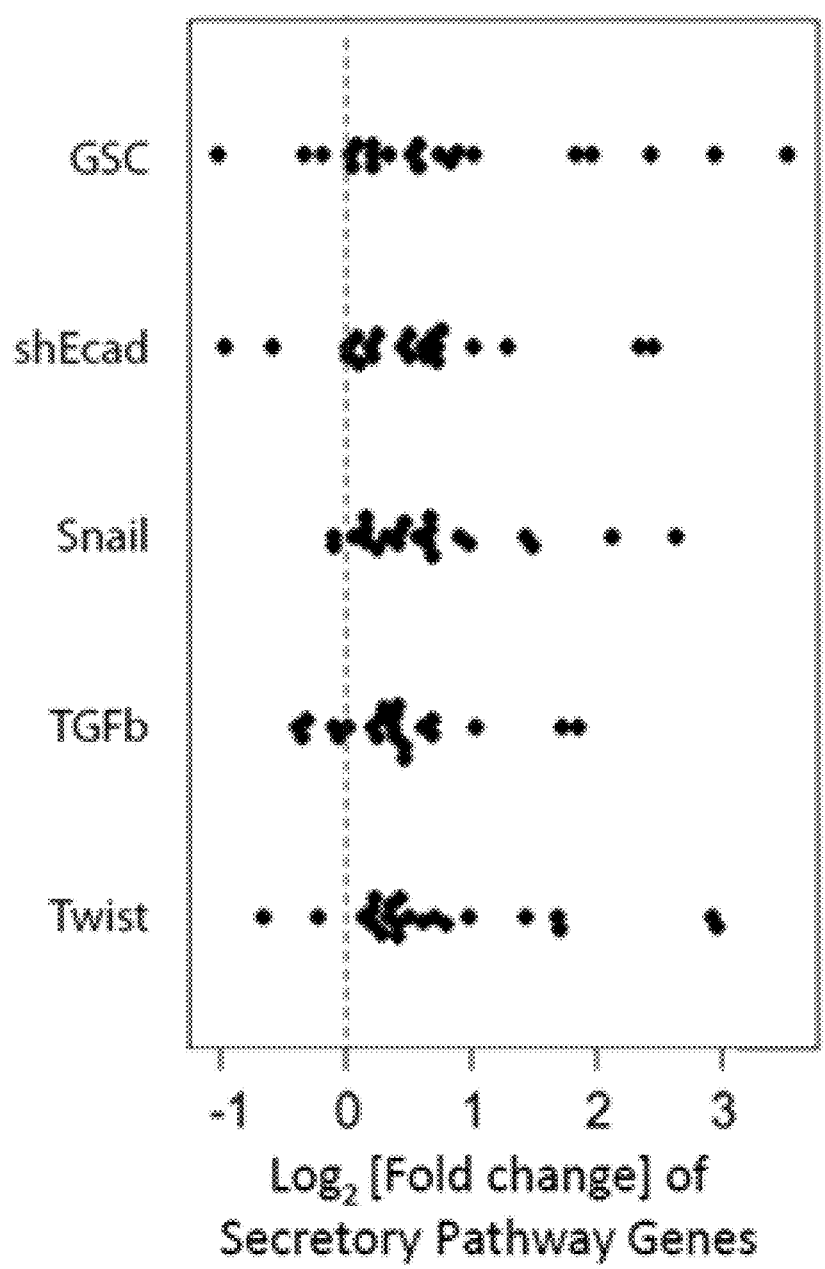

The gene sets most differentially expressed between IDMS and control cells encoded extracellular matrix proteins ($p<10^{-3}$ in all five IDMS cells) and secreted collagens ($p<10^{-3}$ in all five IDMS cells, FIG. 4A). Many individual genes that encode ECM products were strongly upregulated in IDMS cells relative to controls (FIG. 4B). Unbiased network analysis of the genes differentially expressed in IDMS cells indicated that a network of genes that encode secreted ECM products was the second most highly expressed in IDMS cells relative to controls (FIG. 4C); the most highly differentially expressed network corresponded to keratins, known to be modulated upon mesenchymal transdifferentiation (FIG. 9).

If IDMS cells secrete increased quantities of extracellular proteins, they would require an expansion of ER protein secretory capacity. It was therefore hypothesized that IDMS cells might exhibit increased expression of genes that encode components of the secretory pathway. Expression of CREB3L1 (Fox et al., 2010), a master regulator of secretory pathway component expression, increased ~5-fold in IDMS cells relative to controls. Of 20 transcriptional targets of CREB3L1 (Abrams and Andrew, 2005; Fox et al., 2010), 18 secretory pathway component genes are upregulated in at least 4 of the 5 IDMS lines relative to their respective controls ($p<1\times10^{-10}$ using sign test, FIG. 4D).

Figure 4E:
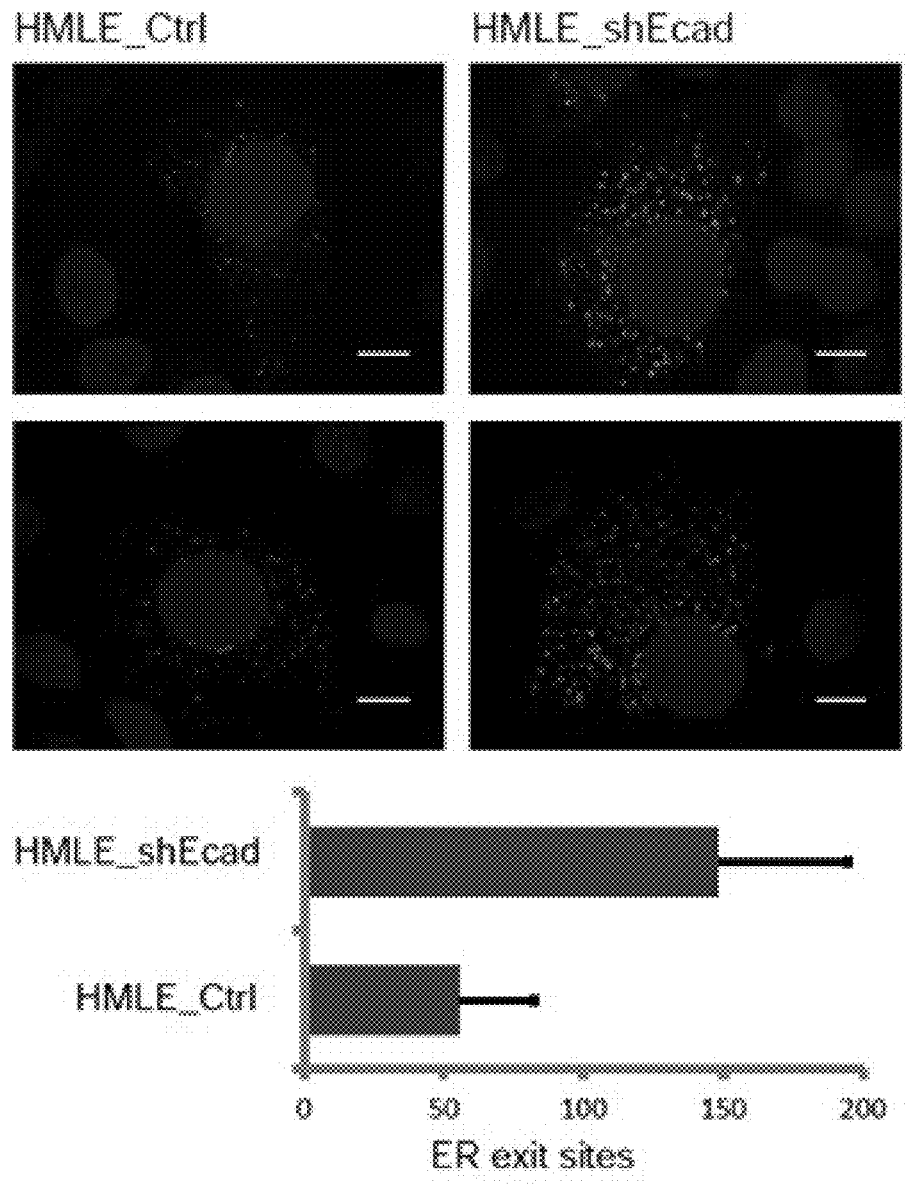

Whether the increase in secretory pathway component expression in IDMS cells is associated with increased intracellular vesicular transport from the ER to cis-Golgi was next assessed. To assess vesicular flux, Sec16, a core component of ER exit sites (Gimeno et al., 1996), fused with GFP was transiently expressed in either IDMS or control cells to visualize ER exit sites by confocal imaging (Aridor et al., 1998; Bhattacharyya and Glick, 2007). Highly secretory cells have increased numbers of ER exit sites to support the increased flux of proteins that leave the ER. Quantification of Sec16-GFP foci revealed a 3-fold increase in the number of ER exit sites in IDMS cells relative to control cells, consistent with an increased secretory burden (FIG. 4E).

Figure 4F:
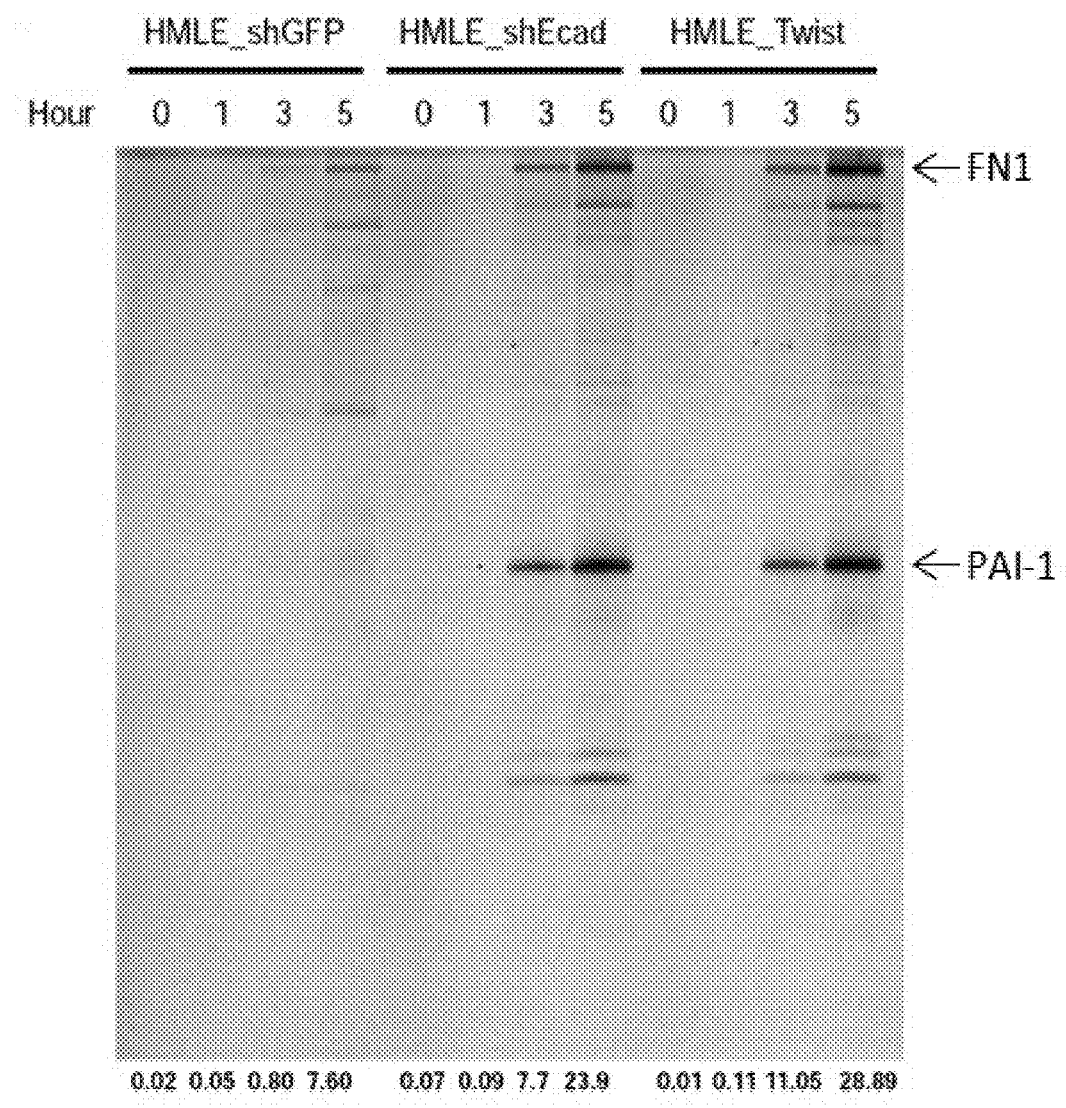

To determine whether overall protein secretion was elevated in IDMS cells, total protein synthesis and secretion was measured using $^{35}$S-methionine/cysteine. Labeled proteins secreted by cells into the culture medium ("secretome") were visualized by gel electrophoresis and autoradiography. After three hours of $^{35}$S-methionine/cysteine labeling, we observed a 9.6-fold and 13.7-fold increase in the secretome of IDMS cells (HMLE_shEcad and HMLE_Twist, resp.) relative to the control epithelial cells (FIG. 4F). As a control, treatment with Brefeldin-A completely abolished protein secretion (data not shown), indicating that protein accumulation in the culture medium is true secretion and not attributable to protein release from dying cells.

Next, whether the increased secretory load of IDMS cells in the HMLE model also applied to IDMS cancer cell lines derived from human breast tumors was determined Breast tumors are broadly divided into Luminal and Basal subtypes. Basal tumors can be further subdivided into two classes—Basal-A and Basal-B (Hollestelle et al., 2010; Neven et al., 2008; Prat et al., 2010). Relative to Luminal breast tumors, Basal B tumors have a relatively poor prognosis and exhibit both increased expression of mesenchymal genes and increased proportions of stem-like cancer cells (Keller et al., 2010; Prat et al., 2010).

Figure 4G:
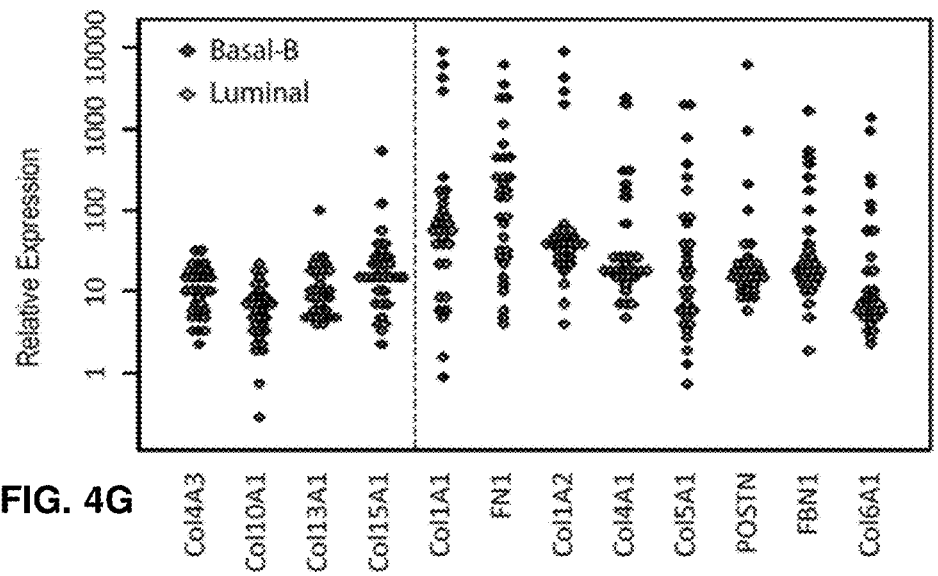
Figure 4H:
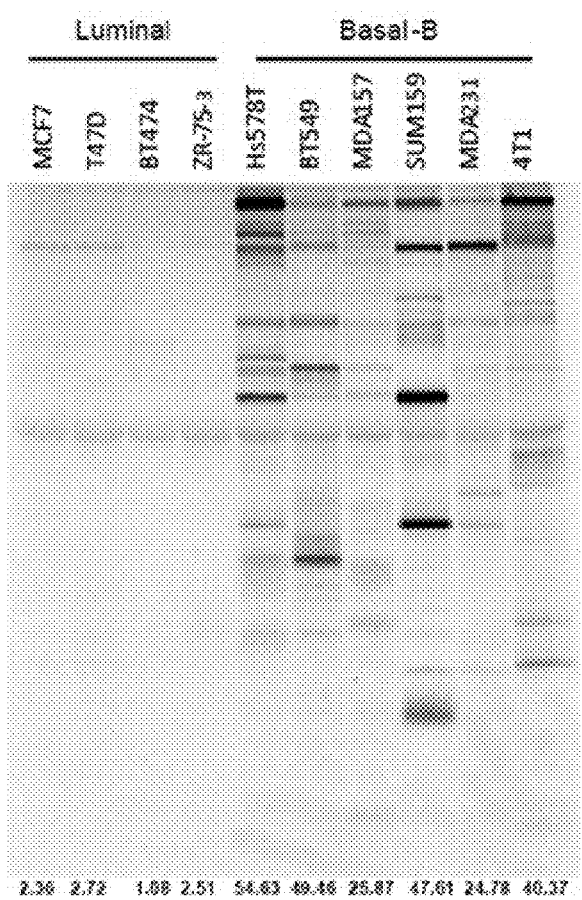

Relative to Luminal breast cancer lines (N=23), Basal-B lines (N=9) were more likely to express the ECM genes also highly expressed in IDMS cells (FIG. 4G). Many of these upregulated ECM genes (FN1, COL1A1, COL1A2, COL4A1, COL5A1, POSTN, FBN1 and COL6A1) were expressed at levels several orders of magnitude higher in a subset of Basal-B lines relative to their average expression in Luminal lines (FIG. 4G). The increased expression in Basal-B cancers was limited to ECM genes expressed in IDMS cells, as several genes did not display increased expression (COL4A3, COL10A1, COL13A1, COL15A1; FIG. 4G). Consistent with the gene expression analysis, all six Basal B lines (Hs578T, BT549, MDA-MB-157, SUM159, MDA-MB-231 and 4T1) exhibited on average greater than 40-fold increase in secretion of extracellular proteins relative to the four Luminal lines (MCF7, T47D, BT474 and ZR-75-3) (FIG. 4H). While the complexity of the total secretome was significantly increased in each of the six Basal B lines relative to each of the four Luminal lines, the levels of specific proteins secreted between the different Basal B lines varied.

IDMS cancer cells thus show a significant increase in both the complexity and quantity of secreted proteins relative to non-IDMS cells.

Example 5

ECM Secretion Promotes Migration but Sensitizes IDMS Cells to ER Stressors

The foregoing observations suggested that the increased ER protein load in IDMS cells sensitized them to chemical perturbants of ER function. If this were indeed the case, then inhibition of genes encoding for major secreted proteins would reduce IDMS cell sensitivity to ER perturbants.

Figure 5A:
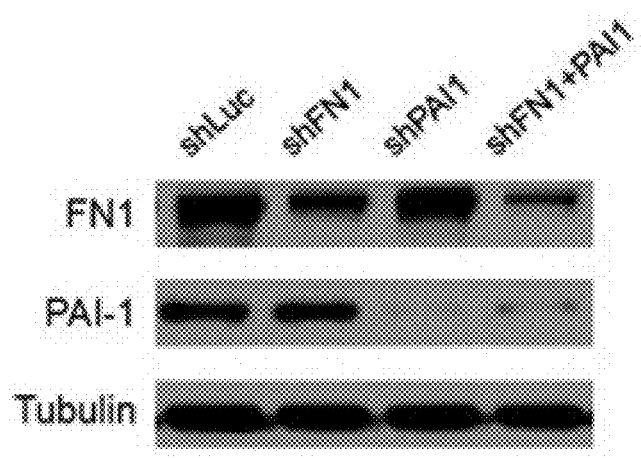
Figure 5B:
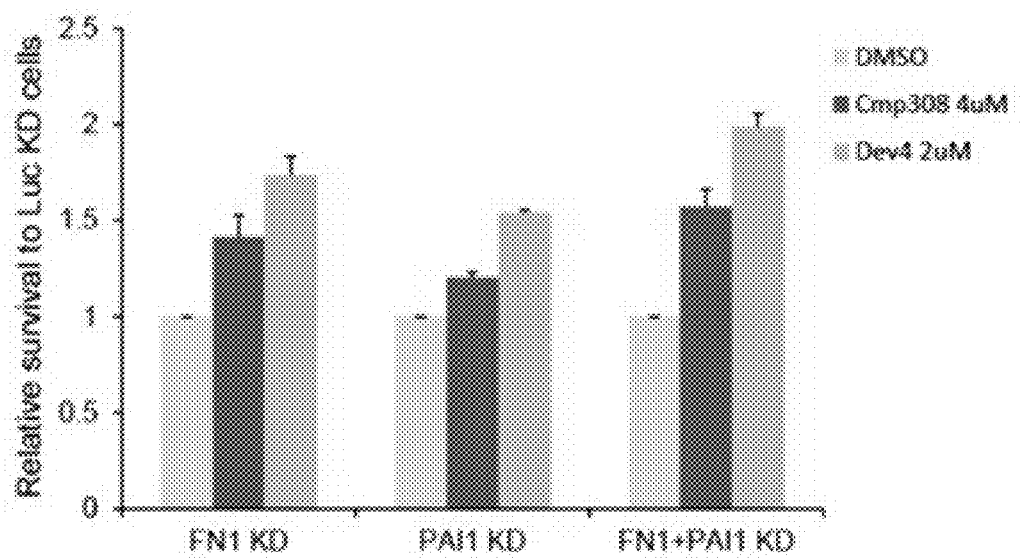
Figure 5C:
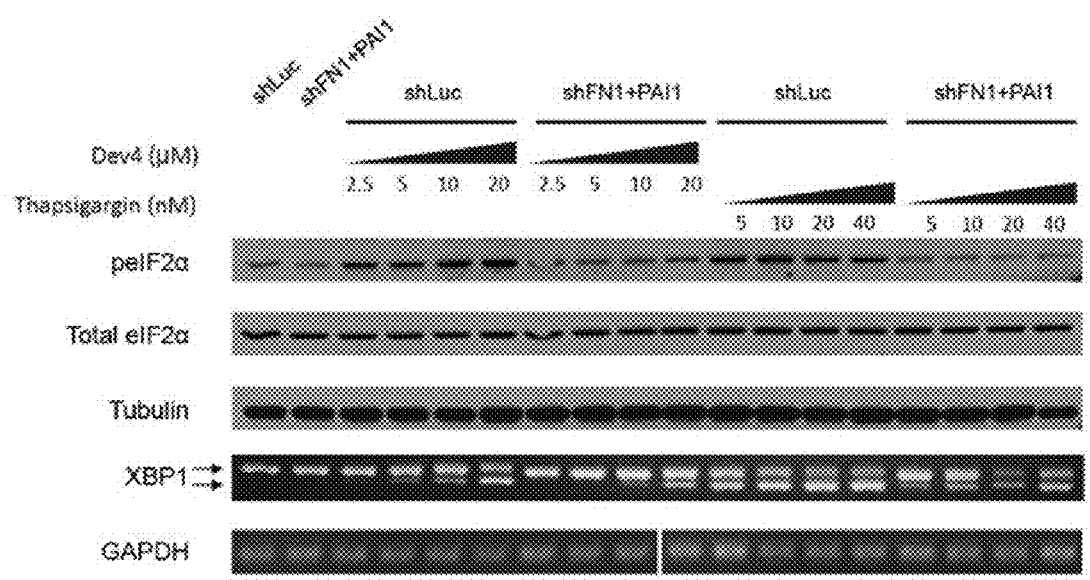
Figure 5D:
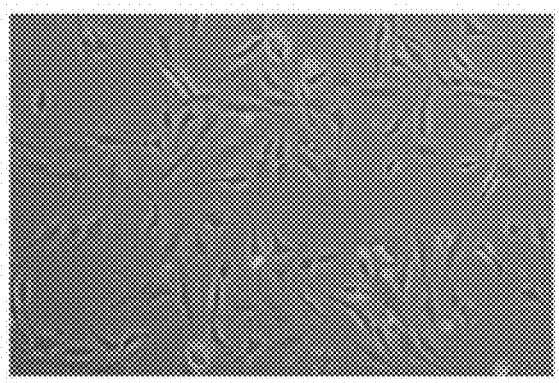
Figure 5D:
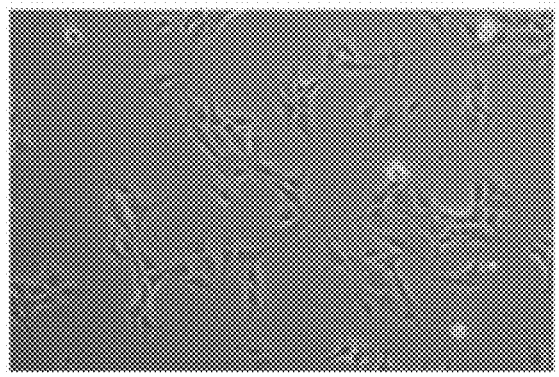

To identify upregulated secreted proteins, bands were excised from silver-stained gels loaded with secreted proteins from IDMS (HMLE_shEcad, HMLE_Twist) and control (HMLE_shGFP) cells. Mass-spectrometric analysis of these fractions identified two extracellular matrix proteins—plasminogen activator inhibitor 1 (PAI1) and fibronectin (FN1)—as constituting the majority of the increased secreted proteins in HMLE_shEcad and HMLE_Twist cells. Accordingly, shRNAs were used to inhibit the expression of PAI1 and FN1, both individually and in combination, in HMLE_shEcad IDMS cells (FIG. 5A). The shRNA-inhibited cells were mixed with control GFP-labeled HMLE_shEcad cells and co-cultured to assess relative viabilities in the presence of chemical compounds Inhibition of either PAI1 or FN1 alone was sufficient to confer resistance to Cmp308 and Dev4 (FIG. 5B); inhibition of both PAI1 and FN1 in combination conferred even greater resistance to these compounds (FIG. 5B). Moreover, inhibition of PAI1 and FN1 expression strongly abrogated eIF2α phosphorylation and XBP1 splicing in response to Dev4 or thapsigargin treatment (FIG. 5C).

Figure 5E:
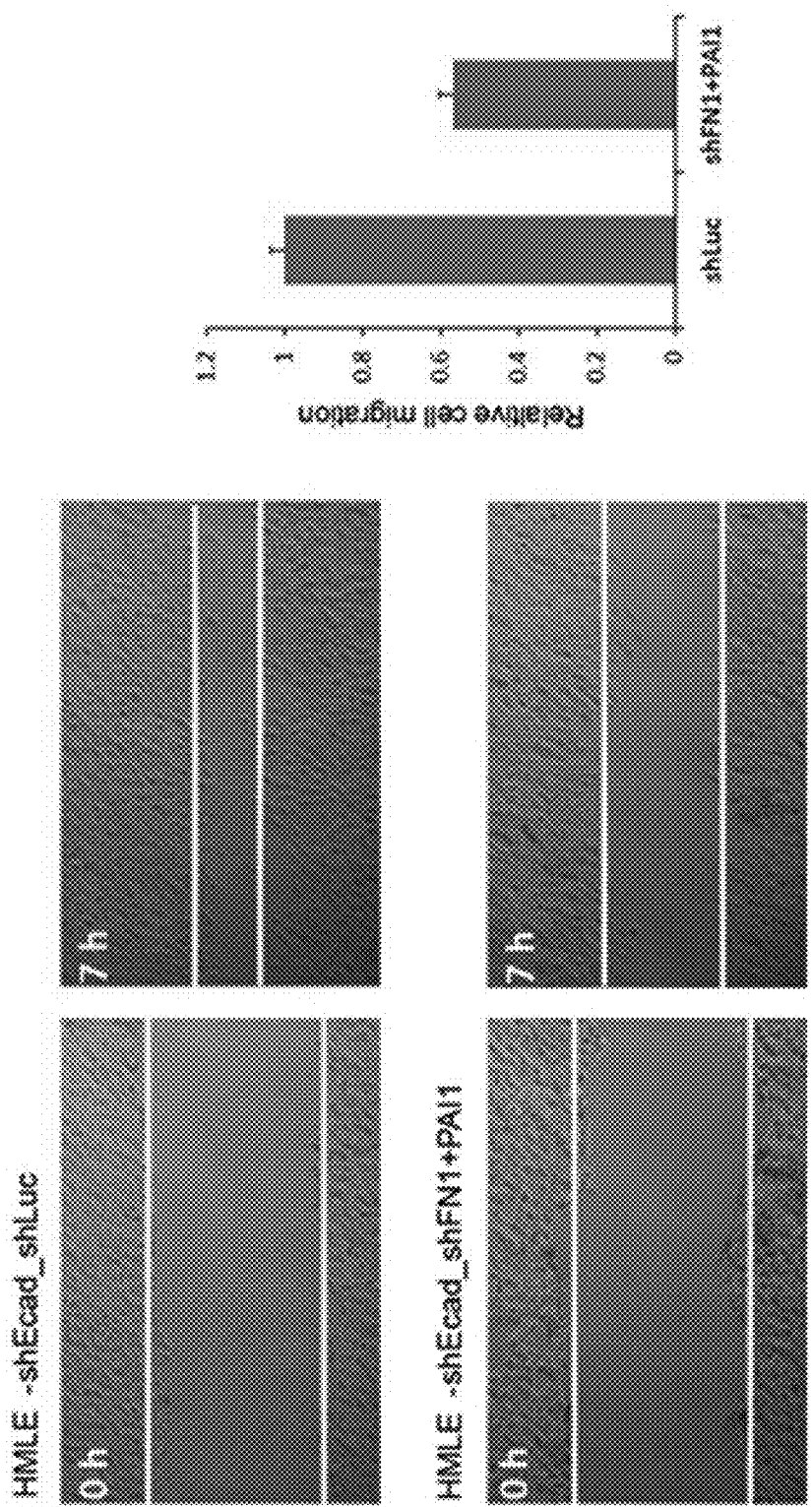

Microscopic examination of cells showed that inhibition of PAI1 and FN1 caused HMLE_shEcad cells to reverse their scattered growth pattern and instead adhere together in cellular clusters (FIG. 5D) Inhibition of PAI1 and FN1 also strongly reduced the migratory ability of the HMLE_shEcad cells, as gauged by a scratch-wound assay (FIG. 5E).

Collectively, these observations demonstrated that the increased ER protein load in IDMS cells is responsible for their increased sensitivity to chemical perturbants of ER function. These results also indicated that the migration of IDMS cells requires expression of specific ECM proteins.

Example 6

Increased Basal PERK-eIF2α Signaling in IDMS Cells

UPR signaling is activated in highly secretory cell types even in the absence of external stressors (Iwakoshi et al., 2003; Zhang et al., 2002). Given the above findings, whether IDMS cells might also exhibit increased basal UPR signaling relative to non-IDMS cells was examined.

Figure 6A:
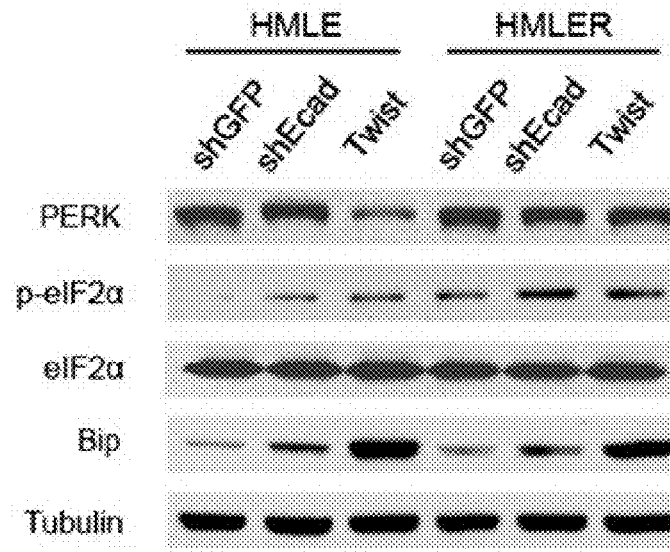
Figure 6B:
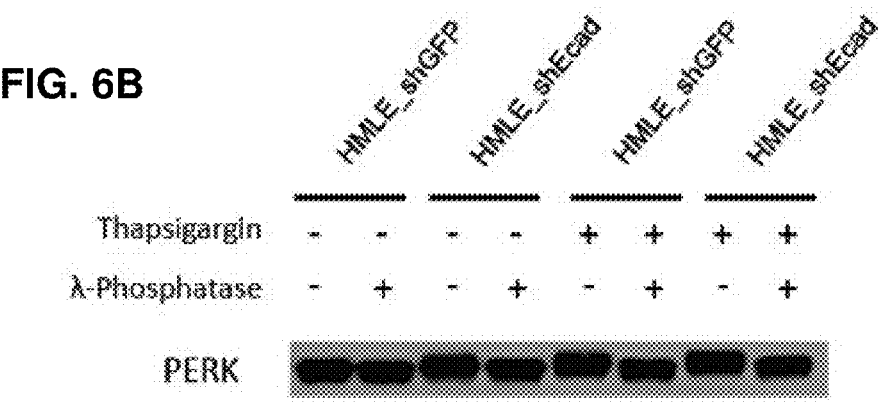

While there were no obvious differences in levels of XBP1 spliced mRNA (XBP1(s)) or cleaved ATF6 protein (FIG. 10A-B), there was a significant increase in eIF2α phosphorylation and Bip expression in IDMS (shEcad, Twist) vs. control (shGFP) HMLE and HMLER cells (FIG. 6A). The electrophoretic mobility of PERK was also reduced in IDMS cells, suggestive of its activation by phosphorylation (FIG. 6A) (Harding et al., 1999; Shi et al., 1998). This was confirmed by treatment of cellular lysates with lambda phosphatase, which abolished the constitutively reduced electrophoretic mobility of PERK in IDMS cells, as well as the alteration in PERK mobility induced by thapsigargin (FIG. 6B).

Figure 6C:
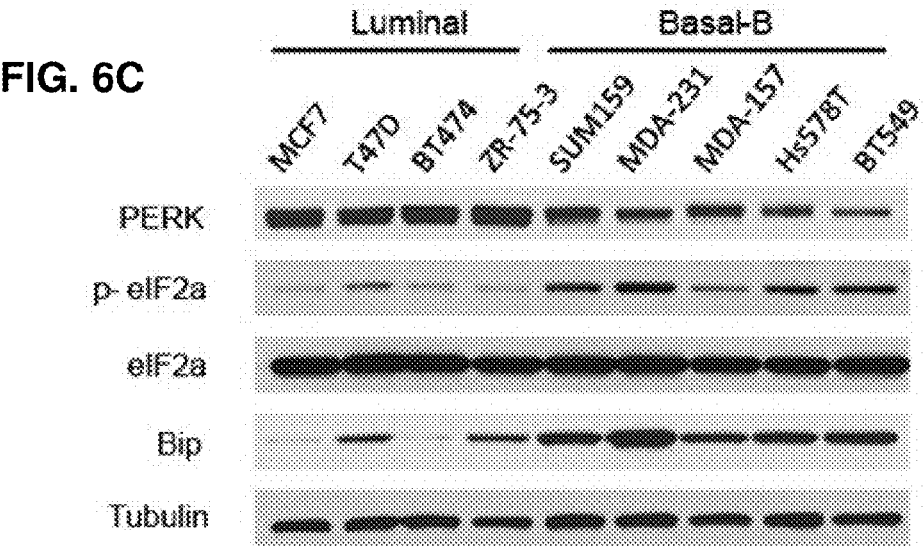

To extend these findings, whether basal UPR signaling was increased in IDMS cells within human breast cancers was also evaluated. Relative to Luminal-subtype breast cancer cells, Basal B cells exhibited increased eIF2α phosphorylation, reduced electrophoretic mobility (phosphorylation) of PERK and increased Bip expression (FIG. 6C). These alterations were observed in all of the Basal B breast cancer cells examined, indicating that constitutive activation of PERK-eIF2α signaling is a common feature of breast cancers harboring high proportions of IDMS cells.

Figure 6D:
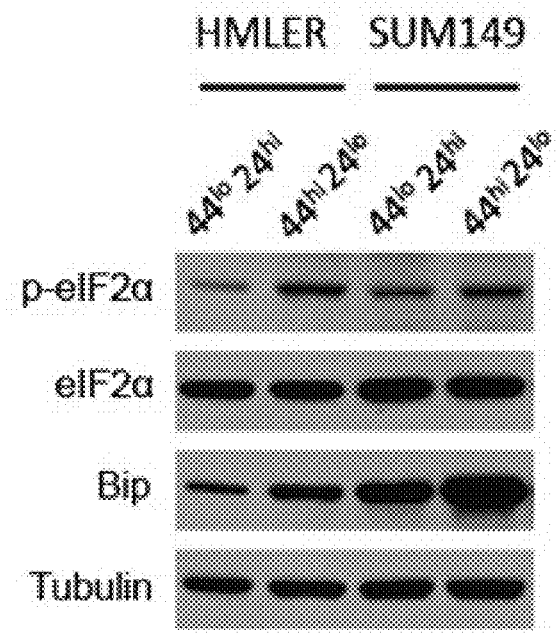
Figure 6E:
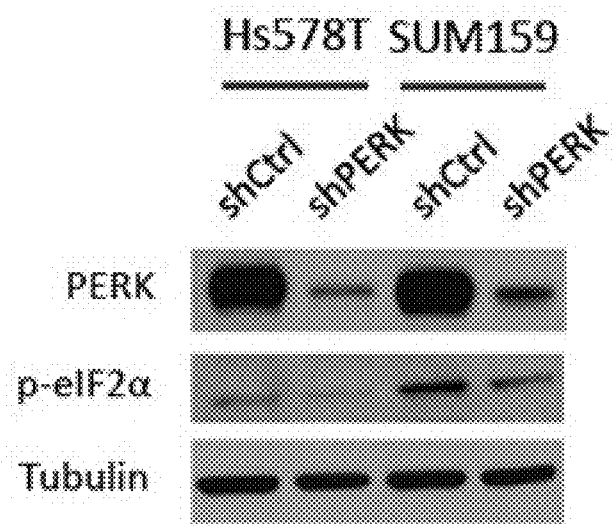

Next, IDMS and non-IDMS subpopulations were separated from heterogeneous breast cancer lines (HMLER, SUM149) and eIF2α phosphorylation was assessed in each fraction. For both lines, the IDMS ($CD44^{hi}CD24^{lo}$) subpopulation exhibited increased eIF2α phosphorylation and Bip expression relative to the non-IDMS ($CD44^{lo}CD24^{hi}$) subpopulation within the same culture (FIG. 6D).

Figure 6F:
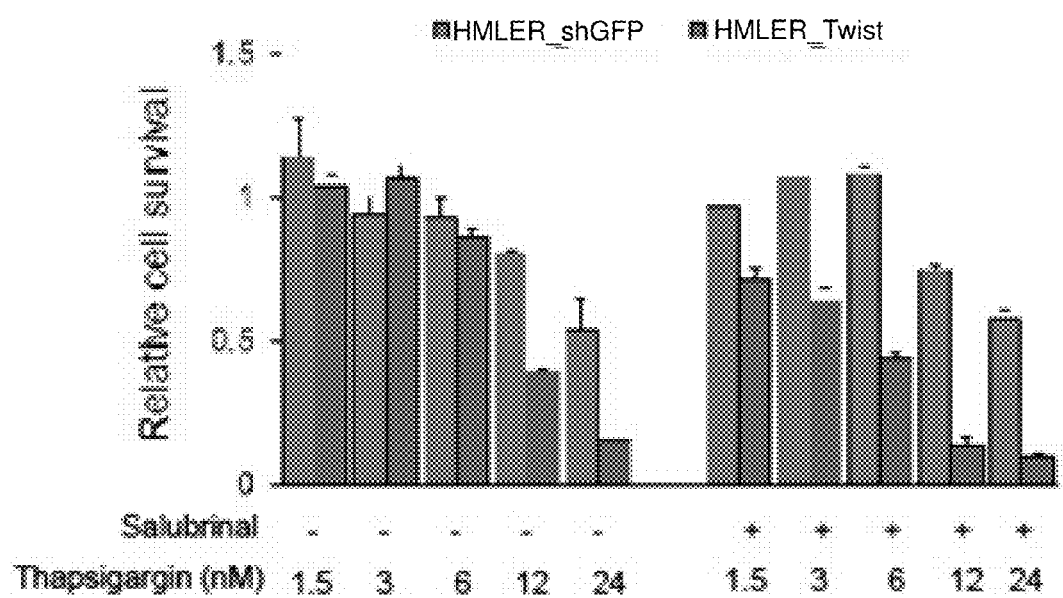
Figure 6G:
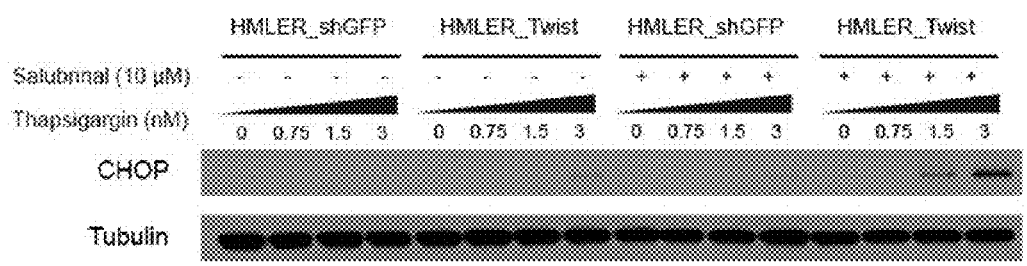

Additionally, PERK inhibition by shRNA-mediated knockdown significantly reduced eIF2α phosphorylation in Hs578t and SUM159 cells (FIG. 6E), indicating that PERK is upstream of eIF2α in IDMS cells. Salubrinal, a chemical inhibitor of eIF2α dephosphorylation, further sensitized HMLER-Twist IDMS, but not control cells, to thapsigargin treatment (FIG. 6F). The increased sensitivity of HMLER-Twist cells to thapsigargin-induced death in the presence of salubrinal correlated with CHOP protein induction (FIG. 6G).

Example 7

Induction of ER Stress Strongly Inhibits the Malignancy of IDMS Cancer Cells

To determine whether chemical ER perturbants could abrogate the malignancy of IDMS cells, SUM159 cancer cells (derived from a primary anaplastic Basal-B breast carcinoma) were treated with tunicamycin, thapsigargin or paclitaxel at their respective $IC_{75}$ doses. Cells were then allowed to recover in the absence of treatment prior to subjecting them to functional assays for IDMS-related phenotypes.

Figure 7A:
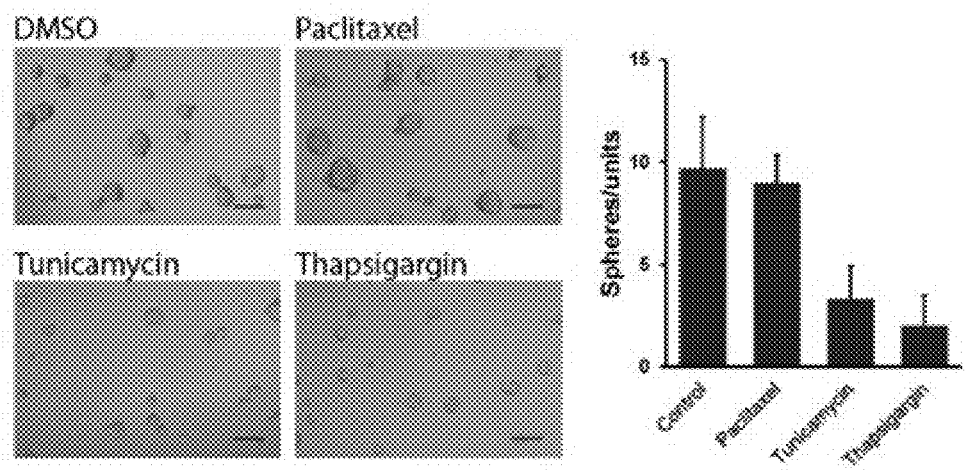
Figure 7B:
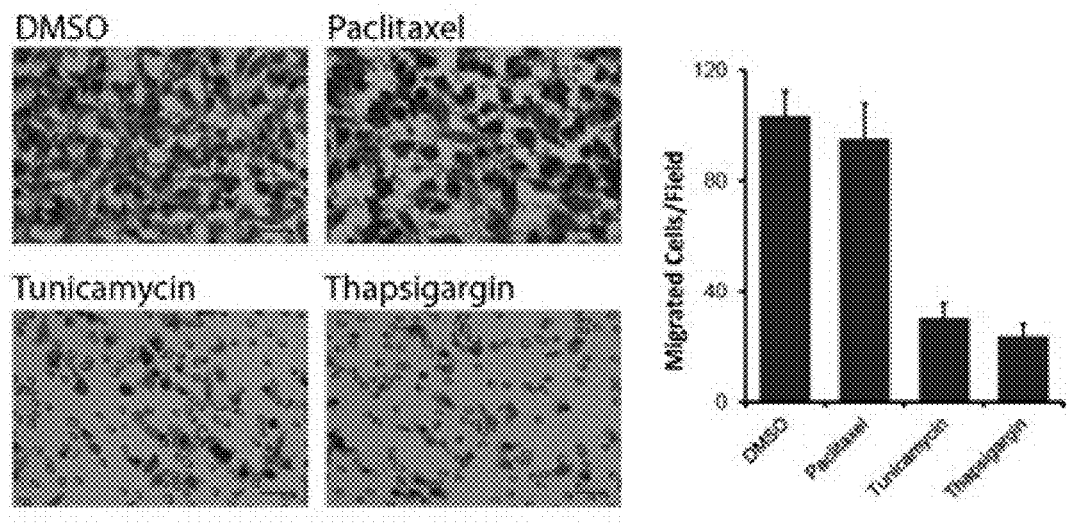
Figure 7C:
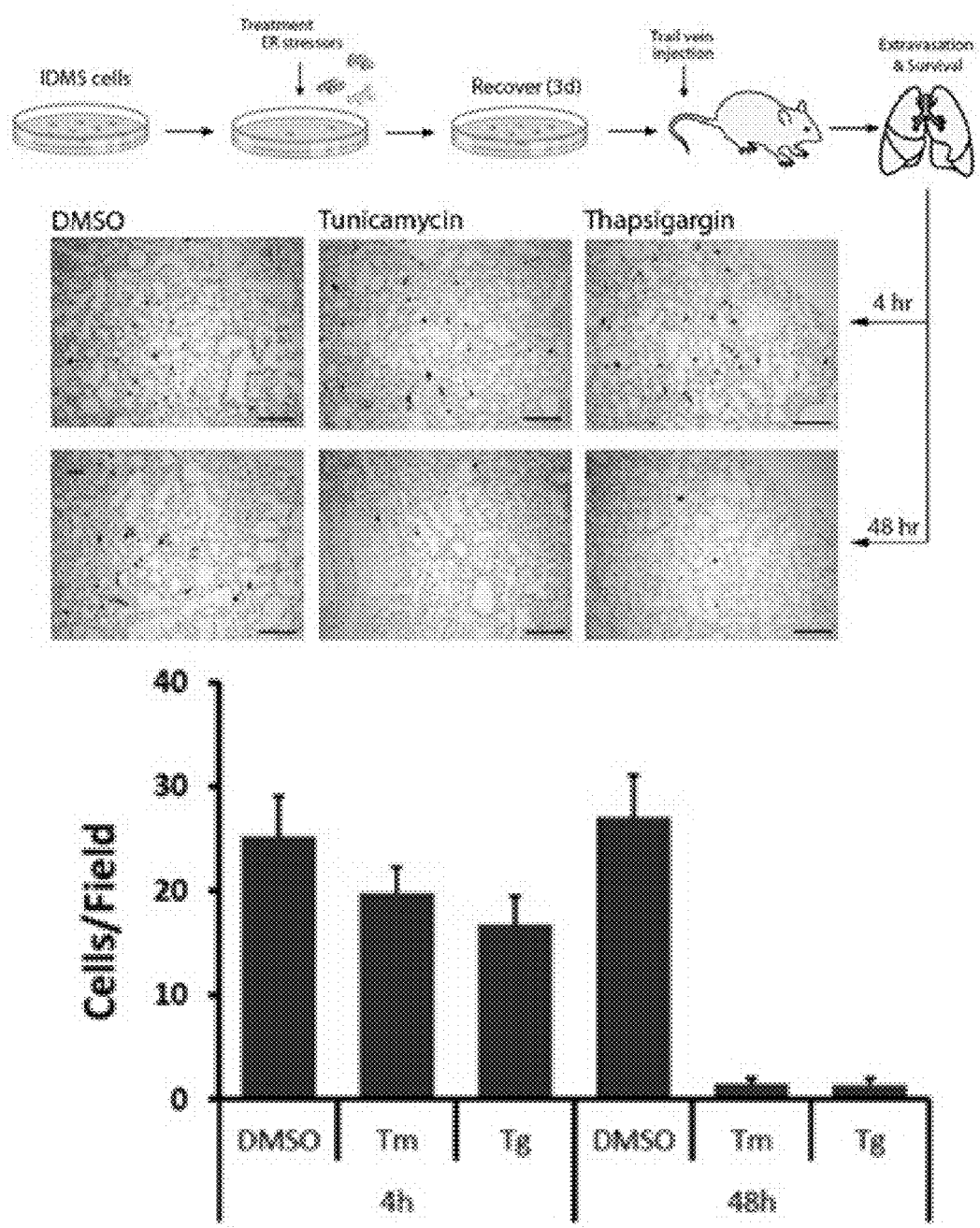

Although the growth rates of the cells pretreated with ER stressors or paclitaxel were comparable (FIG. 11A), SUM159 cells pretreated with thapsigargin or tunicamycin had significantly reduced tumorsphere-forming ability relative to paclitaxel- or DMSO-treated cells (FIG. 7A). The migratory ability of thapsigargin- and tunicamycin-pretreated cells was also strongly impaired relative to paclitaxel-pretreated cells (FIG. 7B).

Next, the effects of pretreatment with ER stressors on in vivo metastasis-seeding ability were assessed. In order to seed metastases, cancer cells must extravasate and survive in a foreign tissue milieu To assay for the effects of ER stressors on this process, chemically pretreated SUM159 cells were injected into the tail veins of immunocompromised mice, and the lungs were subsequently stained for the injected cancer cells. Although SUM159 cells pretreated with ER stressors had comparable rates of early extravasation (FIG. 7C, 4 h), they were strongly compromised in their ability to survive in the lung parenchyma (FIG. 7C, 48 h) relative to control cells.

Figure 7D:
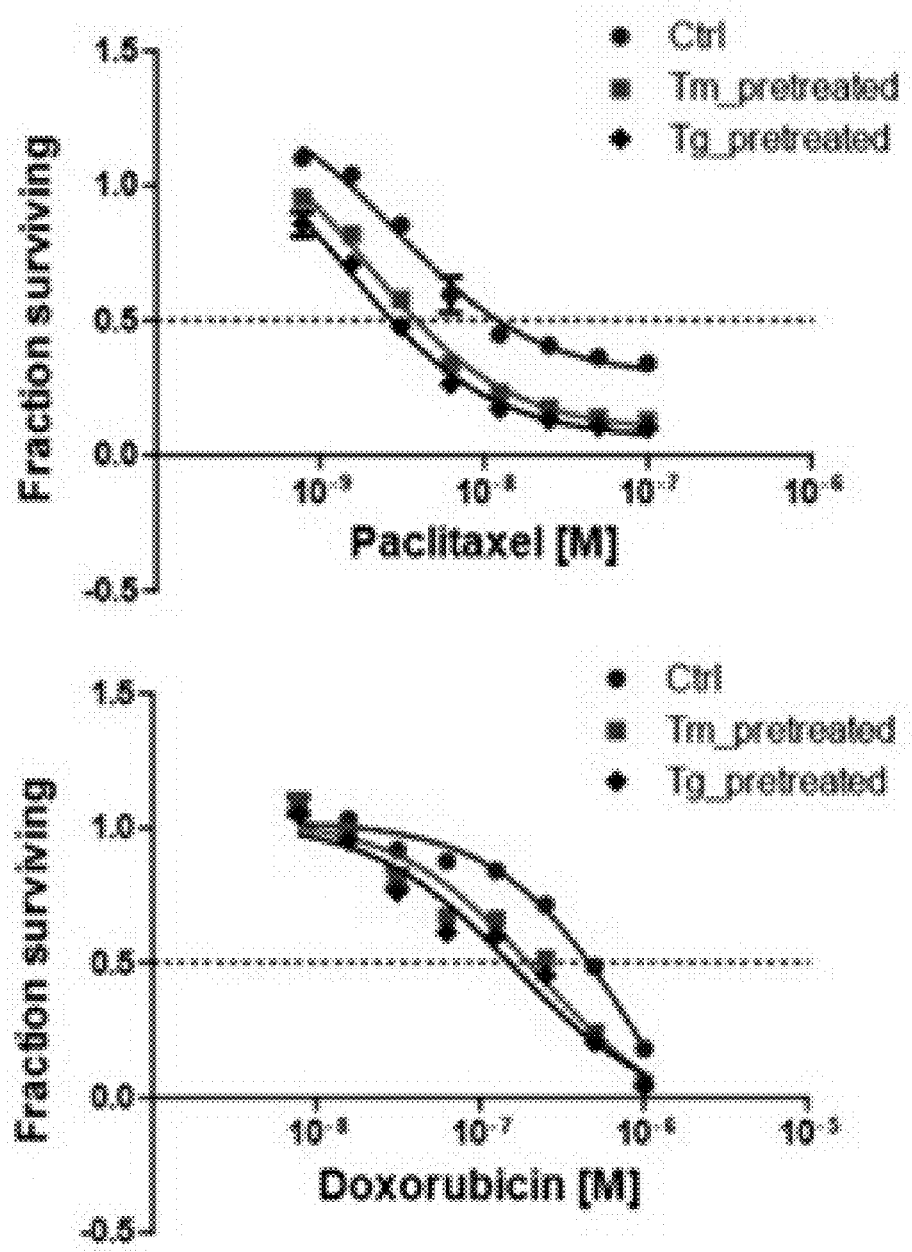

If these ER stressors specifically target IDMS cells, it would be expected that the remaining IDMS-depleted population of cells would exhibit properties of non-IDMS cells, including decreased secretion and sensitivity to traditional chemotherapeutics. Indeed, protein secretion was strongly inhibited in SUM159 populations pretreated with either thapsigargin or tunicamycin, relative to paclitaxel- and DMSO-treated cells (FIG. 11B). Pretreatment with thapsigargin or tunicamycin also sensitized SUM159 cells to paclitaxel and doxorubicin (FIG. 7D).

Thus, treatment with ER stressors strongly inhibits the tumorsphere- and metastasis-forming ability of IDMS cells, as well as their ability to migrate and resist chemotherapies.

Example 8

Figure 7E:
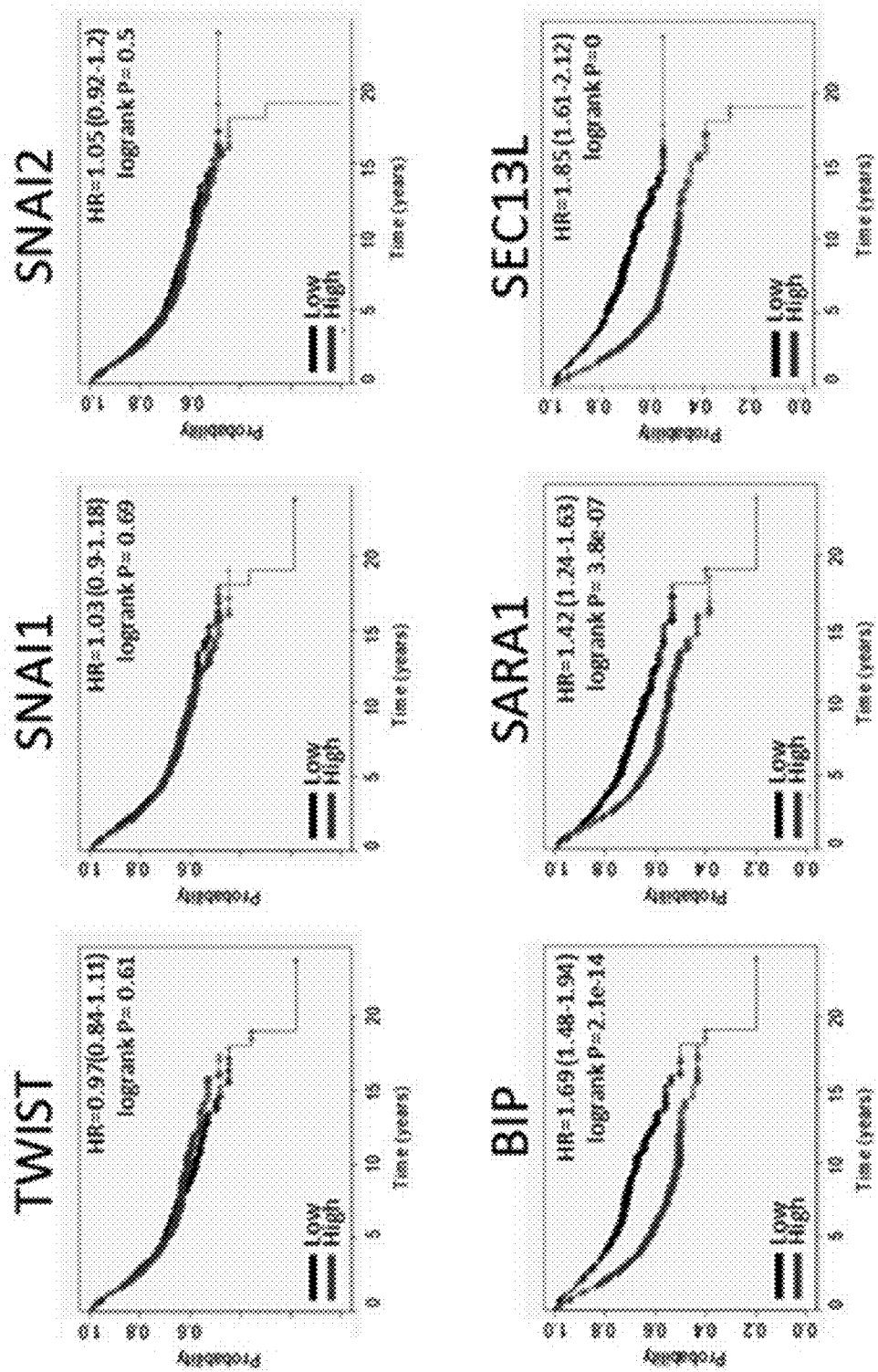

Expression of UPR and Secretory Pathway Genes Correlates with Poor Patient Prognosis Next the prognostic significance of genes involved in EMT, UPR, and protein transport were examined in a well-described large cohort of breast cancer patients (N=2,324) with relapse-free survival information (Gyorffy et al., 2010). Although the co-expression of several EMT factors together correlates with poor prognosis in estrogen receptor-positive breast cancers (van Nes et al., 2011), expression of Twist, Snail, or Slug alone did not correlated with relapse-free survival (TWIST: HR=0.97, logrank p=0.61; SNAI1: HR=1.03, logrank p=0.69; SNAI2: HR=0.92, logrank p=0.5) (FIG. 7E). However, high expression of BIP, SARA1 or SEC13L were each independently correlated with shorter relapse-free survival (BIP: HR=1.69, logrank p=2.1e-10; SARA1: HR=1.42, logrank p=3.8e-07; SEC13L: HR=1.85, logrank p=0) (FIG. 7E). This indicates that UPR activation and high expression of secretory apparatus genes negatively correlate with prognosis.

REFERENCES

Abrams, E. W., and Andrew, D. J. (2005). CrebA regulates secretory activity in the *Drosophila* salivary gland and epidermis. Development 132, 2743-2758.

Aridor, M., Weissman, J., Bannykh, S., Nuoffer, C., and Balch, W. E. (1998). Cargo selection by the COPII budding machinery during export from the ER. J Cell Biol 141, 61-70.

Bao, S., Wu, Q., McLendon, R. E., Hao, Y., Shi, Q., Hjelmeland, A. B., Dewhirst, M. W., Bigner, D. D., and Rich, J. N. (2006). Glioma stem cells promote radioresistance by preferential activation of the DNA damage response. Nature 444, 756-760.

Bartkowiak, K., Effenberger, K. E., Harder, S., Andreas, A., Buck, F., Peter-Katalinic, J., Pantel, K., and Brandt, B. H. (2010). Discovery of a novel unfolded protein response phenotype of cancer stem/progenitor cells from the bone marrow of breast cancer patients. J Proteome Res 9, 3158-3168.

Bergmeier, W., and Hynes, R. O. (2012). Extracellular matrix proteins in hemostasis and thrombosis. Cold Spring Harb Perspect Biol 4.

Bhattacharyya, D., and Glick, B. S. (2007). Two mammalian Sec16 homologues have nonredundant functions in endoplasmic reticulum (ER) export and transitional ER organization. Mol Biol Cell 18, 839-849.

Bi, M., Naczki, C., Koritzinsky, M., Fels, D., Blais, J., Hu, N., Harding, H., Novoa, I., Varia, M., Raleigh, J., et al. (2005). ER stress-regulated translation increases tolerance to extreme hypoxia and promotes tumor growth. EMBO J 24, 3470-3481.

Chen, J. J. (2007). Regulation of protein synthesis by the heme-regulated eIF2alpha kinase: relevance to anemias. Blood 109, 2693-2699.

Clemens, M. J., and Elia, A. (1997). The double-stranded RNA-dependent protein kinase PKR: structure and function. J Interferon Cytokine Res 17, 503-524.

Del Castillo, G., Murillo, M. M., Alvarez-Barrientos, A., Bertran, E., Fernandez, M., Sanchez, A., and Fabregat, I. (2006). Autocrine production of TGF-beta confers resistance to apoptosis after an epithelial-mesenchymal transition process in hepatocytes: Role of EGF receptor ligands. Exp Cell Res 312, 2860-2871.

Diehn, M., and Clarke, M. F. (2006). Cancer stem cells and radiotherapy: new insights into tumor radioresistance. J Natl Cancer Inst 98, 1755-1757.

Dontu, G., Abdallah, W. M., Foley, J. M., Jackson, K. W., Clarke, M. F., Kawamura, M. J., and Wicha, M. S. (2003). In vitro propagation and transcriptional profiling of human mammary stem/progenitor cells. Genes Dev 17, 1253-1270.

Fox, R. M., Hanlon, C. D., and Andrew, D. J. (2010). The CrebA/Creb3-like transcription factors are major and direct regulators of secretory capacity. J Cell Biol 191, 479-492.

Franco, D. L., Mainez, J., Vega, S., Sancho, P., Murillo, M. M., de Frutos, C. A., Del Castillo, G., Lopez-Blau, C., Fabregat, I., and Nieto, M. A. (2010). Snail1 suppresses TGF-beta-induced apoptosis and is sufficient to trigger EMT in hepatocytes. J Cell Sci 123, 3467-3477.

Germain, A. R., Carmody, L. C., Morgan, B., Fernandez, C., Forbeck, E., Lewis, T. A., Nag, P. P., Ting, A., VerPlank, L., Feng, Y., et al. (2012) Identification of a selective small molecule inhibitor of breast cancer stem cells. Bioorg Med Chem Lett. 22, 3571-3574.

Gimeno, R. E., Espenshade, P., and Kaiser, C. A. (1996). COPII coat subunit interactions: Sec24p and Sec23p bind to adjacent regions of Sec16p. Mol Biol Cell 7, 1815-1823.

Gomez, B. P., Riggins, R. B., Shajahan, A. N., Klimach, U., Wang, A., Crawford, A. C., Zhu, Y., Zwart, A., Wang, M., and Clarke, R. (2007). Human X-box binding protein-1 confers both estrogen independence and antiestrogen resistance in breast cancer cell lines. FASEB J 21, 4013-4027.

Guo, W., Keckesova, Z., Donaher, J. L., Shibue, T., Tischler, V., Reinhardt, F., Itzkovitz, S., Noske, A., Zurrer-Hardi, U., Bell, G., et al. (2012). Slug and Sox9 cooperatively determine the mammary stem cell state. Cell 148, 1015-1028.

Gupta, P. B., Kuperwasser, C., Brunet, J. P., Ramaswamy, S., Kuo, W. L., Gray, J. W., Naber, S. P., and Weinberg, R. A. (2005). The melanocyte differentiation program predisposes to metastasis after neoplastic transformation. Nat Genet 37, 1047-1054.

Gupta, P. B., Onder, T. T., Jiang, G., Tao, K., Kuperwasser, C., Weinberg, R. A., and Lander, E. S. (2009). Identification of selective inhibitors of cancer stem cells by high-throughput screening. Cell 138, 645-659.

Gyorffy, B., Lanczky, A., Eklund, A. C., Denkert, C., Budczies, J., Li, Q., and Szallasi, Z. (2010). An online survival analysis tool to rapidly assess the effect of 22,277 genes on breast cancer prognosis using microarray data of 1,809 patients. Breast Cancer Res Treat 123, 725-731.

Harding, H. P., Zhang, Y., and Ron, D. (1999). Protein translation and folding are coupled by an endoplasmic-reticulum-resident kinase. Nature 397, 271-274.

Harding, H. P., Zhang, Y., Zeng, H., Novoa, I., Lu, P. D., Calfon, M., Sadri, N., Yun, C., Popko, B., Paules, R., et al. (2003). An integrated stress response regulates amino acid metabolism and resistance to oxidative stress. Mol Cell 11, 619-633.

Hetz, C. (2012). The unfolded protein response: controlling cell fate decisions under ER stress and beyond. Nat Rev Mol Cell Biol 13, 89-102.

Hollestelle, A., Nagel, J. H., Smid, M., Lam, S., Elstrodt, F., Wasielewski, M., Ng, S. S., French, P. J., Peeters, J. K., Rozendaal, M. J., et al. (2010). Distinct gene mutation profiles among luminal-type and basal-type breast cancer cell lines. Breast Cancer Res Treat 121, 53-64.

Ince, T. A., Richardson, A. L., Bell, G. W., Saitoh, M., Godar, S., Karnoub, A. E., Iglehart, J. D., and Weinberg, R. A. (2007). Transformation of different human breast epithelial cell types leads to distinct tumor phenotypes. Cancer Cell 12, 160-170.

Iwakoshi, N. N., Lee, A. H., Vallabhajosyula, P., Otipoby, K. L., Rajewsky, K., and Glimcher, L. H. (2003). Plasma cell differentiation and the unfolded protein response intersect at the transcription factor XBP-1. Nat Immunol 4, 321-329.

Kaufman, R. J. (2002). Orchestrating the unfolded protein response in health and disease. J Clin Invest 110, 1389-1398.

Keller, P. J., Arendt, L. M., Skibinski, A., Logvinenko, T., Klebba, I., Dong, S., Smith, A. E., Prat, A., Perou, C. M., Gilmore, H., et al. (2012). Defining the cellular precursors to human breast cancer. Proc Natl Acad Sci USA 109, 2772-2777.

Keller, P. J., Lin, A. F., Arendt, L. M., Klebba, I., Jones, A. D., Rudnick, J. A., Dimeo, T. A., Gilmore, H., Jefferson, D. M., Graham, R. A., et al. (2010). Mapping the cellular and molecular heterogeneity of normal and malignant breast tissues and cultured cell lines. Breast Cancer Res 12, R87.

Korpal, M., Ell, B. J., Buffa, F. M., Ibrahim, T., Blanco, M. A., Celia-Terrassa, T., Mercatali, L., Khan, Z., Goodarzi, H., Hua, Y., et al. (2011). Direct targeting of Sec23a by miR-200s influences cancer cell secretome and promotes metastatic colonization. Nat Med 17, 1101-1108.

Lee, E., Nichols, P., Groshen, S., Spicer, D., and Lee, A. S. (2011). GRP78 as potential predictor for breast cancer response to adjuvant taxane therapy. Int J Cancer 128, 726-731.

Liu, L., Wise, D. R., Diehl, J. A., and Simon, M. C. (2008). Hypoxic reactive oxygen species regulate the integrated stress response and cell survival. J Biol Chem 283, 31153-31162.

Luo, B., Cheung, H. W., Subramanian, A., Sharifnia, T., Okamoto, M., Yang, X., Hinkle, G., Boehm, J. S., Beroukhim, R., Weir, B. A., et al. (2008). Highly parallel identification of essential genes in cancer cells. Proc Natl Acad Sci USA 105, 20380-20385.

Mani, S. A., Guo, W., Liao, M. J., Eaton, E. N., Ayyanan, A., Zhou, A. Y., Brooks, M., Reinhard, F., Zhang, C. C., Shipitsin, M., et al. (2008). The epithelial-mesenchymal transition generates cells with properties of stem cells. Cell 133, 704-715.

McMillan, D. R., Gething, M. J., and Sambrook, J. (1994). The cellular response to unfolded proteins: intercompartmental signaling. Curr Opin Biotechnol 5, 540-545.

Mozos, A., Roue, G., Lopez-Guillermo, A., Jares, P., Campo, E., Colomer, D., and Martinez, A. (2011). The expression of the endoplasmic reticulum stress sensor BiP/GRP78 predicts response to chemotherapy and determines the efficacy of proteasome inhibitors in diffuse large b-cell lymphoma. Am J Pathol 179, 2601-2610.

Neven, P., Van Gorp, T., and Deraedt, K. (2008). A gene signature of loss of oestrogen receptor (ER) function and oxidative stress links ER-positive breast tumours with an absent progesterone receptor and a poor prognosis. Breast Cancer Res 10, 109.

Prat, A., Parker, J. S., Karginova, O., Fan, C., Livasy, C., Herschkowitz, J. I., He, X., and Perou, C. M. (2010). Phenotypic and molecular characterization of the claudin-low intrinsic subtype of breast cancer. Breast Cancer Res 12, R68.

Ranganathan, A. C., Zhang, L., Adam, A. P., and Aguirre-Ghiso, J. A. (2006). Functional coupling of p38-induced up-regulation of BiP and activation of RNA-dependent protein kinase-like endoplasmic reticulum kinase to drug resistance of dormant carcinoma cells. Cancer Res 66, 1702-1711.

Reimold, A. M., Iwakoshi, N. N., Manis, J., Vallabhajosyula, P., Szomolanyi-Tsuda, E., Gravallese, E. M., Friend, D., Grusby, M. J., Alt, F., and Glimcher, L. H. (2001). Plasma cell differentiation requires the transcription factor XBP-1. Nature 412, 300-307.

Ron, D. (2002). Translational control in the endoplasmic reticulum stress response. J Clin Invest 110, 1383-1388.

Ron, D., and Walter, P. (2007). Signal integration in the endoplasmic reticulum unfolded protein response. Nat Rev Mol Cell Biol 8, 519-529.

Rzymski, T., Milani, M., Singleton, D. C., and Harris, A. L. (2009). Role of ATF4 in regulation of autophagy and resistance to drugs and hypoxia. Cell Cycle 8, 3838-3847.

Sanai, N., Alvarez-Buylla, A., and Berger, M. S. (2005). Neural stem cells and the origin of gliomas. N Engl J Med 353, 811-822.

Schedin, P., and Keely, P. J. (2011). Mammary gland ECM remodeling, stiffness, and mechanosignaling in normal development and tumor progression. Cold Spring Harb Perspect Biol 3, a003228.

Schroder, M., and Kaufman, R. J. (2005). The mammalian unfolded protein response. Annu Rev Biochem 74, 739-789.

Shi, Y., Vattem, K. M., Sood, R., An, J., Liang, J., Stramm, L., and Wek, R. C. (1998). Identification and characterization of pancreatic eukaryotic initiation factor 2 alpha-subunit kinase, PEK, involved in translational control. Mol Cell Biol 18, 7499-7509.

Sidrauski, C., Chapman, R., and Walter, P. (1998). The unfolded protein response: an intracellular signalling pathway with many surprising features. Trends Cell Biol 8, 245-249.

Subramanian, A., Tamayo, P., Mootha, V. K., Mukherjee, S., Ebert, B. L., Gillette, M. A., Paulovich, A., Pomeroy, S. L., Golub, T. R., Lander, E. S., et al. (2005). Gene set enrichment analysis: a knowledge-based approach for interpreting genome-wide expression profiles. Proc Natl Acad Sci USA 102, 15545-15550.

Taube, J. H., Herschkowitz, J. I., Komurov, K., Zhou, A. Y., Gupta, S., Yang, J., Hartwell, K., Onder, T. T., Gupta, P. B., Evans, K. W., et al. (2010). Core epithelial-to-mesenchymal transition interactome gene-expression signature is associated with claudin-low and metaplastic breast cancer subtypes. Proc Natl Acad Sci USA 107, 15449-15454.

Tsai, Y. C., and Weissman, A. M. (2010). The Unfolded Protein Response, Degradation from Endoplasmic Reticulum and Cancer. Genes Cancer 1, 764-778.

Valdes, F., Alvarez, A. M., Locascio, A., Vega, S., Herrera, B., Fernandez, M., Benito, M., Nieto, M. A., and Fabregat, I. (2002). The epithelial mesenchymal transition confers resistance to the apoptotic effects of transforming growth factor Beta in fetal rat hepatocytes. Mol Cancer Res 1, 68-78.

van Nes, J. G., de Kruijf, E. M., Putter, H., Faratian, D., Munro, A., Campbell, F., Smit, V. T., Liefers, G. J., Kuppen, P. J., van de Velde, C. J., et al. (2011). Co-expression of SNAIL and TWIST determines prognosis in estrogen receptor-positive early breast cancer patients. Breast Cancer Res Treat.

Walter, P., and Ron, D. (2011). The unfolded protein response: from stress pathway to homeostatic regulation. Science 334, 1081-1086.

Woodward, W. A., Chen, M. S., Behbod, F., Alfaro, M. P., Buchholz, T. A., and Rosen, J. M. (2007). WNT/beta-catenin mediates radiation resistance of mouse mammary progenitor cells. Proc Natl Acad Sci USA 104, 618-623.

Wouters, B. G., and Koritzinsky, M. (2008). Hypoxia signalling through mTOR and the unfolded protein response in cancer. Nat Rev Cancer 8, 851-864.

Zhang, P., McGrath, B., Li, S., Frank, A., Zambito, F., Reinert, J., Gannon, M., Ma, K., McNaughton, K., and Cavener, D. R. (2002). The PERK eukaryotic initiation factor 2 alpha kinase is required for the development of the skeletal system, postnatal growth, and the function and viability of the pancreas. Mol Cell Biol 22, 3864-3874.

Zinszner, H., Kuroda, M., Wang, X., Batchvarova, N., Lightfoot, R. T., Remotti, H., Stevens, J. L., and Ron, D. (1998). CHOP is implicated in programmed cell death in response to impaired function of the endoplasmic reticulum. Genes Dev 12, 982-995.

What is claimed is:

1. A method of selecting a treatment for a subject having a carcinoma, the method comprising:

conducting an assay to determine the extent of UPR signaling in cells of the carcinoma, wherein, if the extent of UPR signaling in the cells of the carcinoma is higher than the extent of UPR signaling in cells from normal epithelium, then an ER-stress inducing compound is suitable for treating the subject, and if the extent of UPR signaling in the cells of the carcinoma is equal to or less than the extent of UPR signaling in cells from normal epithelium, then an ER-stress inducing compound is not suitable for treating the subject; and selecting a treatment for the subject based at least in part on the results of the assay.

2. The method of claim 1, wherein the extent of UPR signaling in the cells of the carcinoma is higher than the extent of UPR signaling in cells from normal epithelium, and the method further comprises treating the subject with an ER-stress inducing compound based on the results of the assay.

3. The method of claim 1, wherein the cells of the carcinoma are cancer stem cells.

4. The method of claim 1, wherein the extent of UPR signaling is directly related to the secretory load on the cells.

5. The method of claim 1, wherein conducting an assay to determine the extent of UPR signaling comprises measuring activity of the PERK signaling pathway.

6. The method of claim 1, wherein conducting an assay to determine the extent of UPR signaling comprises measuring activity of the IRE1a signaling pathway.

7. The method of claim 1, wherein conducting an assay to determine the extent of UPR signaling comprises measuring activity of the ATF6 signaling pathway.

8. The method of claim 1, wherein conducting an assay to determine the extent of UPR signaling comprises measuring phosphorylation of eIF2α as an indicator of activity of the PERK signaling pathway, measuring splicing of XBP1 mRNA as an indicator of activity of the IRE1a signaling pathway, or measuring nuclear translocation of ATF6 as a marker of the ATF6 signaling pathway, or a combination thereof.

9. The method of claim 1, wherein conducting an assay to determine the extent of UPR signaling comprises measuring expression of CHOP, Bip, calnexin or GRP94.

10. The method of claim 1, wherein conducting an assay to determine the extent of UPR signaling comprises measuring activity of one or more UPR signaling pathways in cells of the carcinoma and determining that the activity of at least one of the UPR signaling pathways in cells of the carcinoma is higher than the activity of such UPR signaling pathway(s) in normal epithelium; and selecting a method of treatment comprises selecting an ER-stress inducing compound as a treatment for the subject.

11. The method of claim 10, wherein conducting an assay to determine the extent of UPR signaling comprises measuring activity of two or more UPR signaling pathways in cells of the carcinoma and determining that only a subset of UPR signaling pathways are active in the cells, and the method further comprises utilizing one or more of the other UPR signaling pathways as a biomarker of the responsiveness of the carcinoma to the treatment.

12. The method of claim 11, wherein utilizing a UPR signaling pathway as a biomarker of the responsiveness of the carcinoma to the treatment comprises measuring the activity of the UPR signaling pathway in cells of the carcinoma after treatment with the compound and comparing the level of activity with the level of activity prior to treatment, wherein an increase in activity of the pathway as compared to the level of activity before treatment is indicative of responsiveness of the carcinoma to the compound.

13. The method of claim 11, wherein the method comprises determining that PERK signaling is active prior to the treatment, and the method further comprises measuring the activity of of IRE1a, IRE1b and/or ATF6 signaling pathways as biomarkers of responsiveness.

14. The method of claim 11, wherein the method comprises determining that IRE1a signaling is active prior to the treatment, and the method further comprises measuring the activity of PERK, IRE1b and/or ATF6 signaling pathways as biomarkers of responsiveness.

15. The method of claim 11, wherein the method comprises determining that IRE1b signaling is active prior to the treatment, and the method further comprises measuring the activity of PERK, IRE1a and/or ATF6 signaling pathways as biomarkers of responsiveness.

16. The method of claim 11, wherein the method comprises determining that ATF6 signaling is active prior to the treatment, and the method further comprises measuring the activity of PERK, IRE1a and/or IRE1b signaling pathways as biomarkers of responsiveness.

* * * * *